US010040850B2

(12) United States Patent
Rau et al.

(10) Patent No.: US 10,040,850 B2
(45) Date of Patent: Aug. 7, 2018

(54) PROTECTING GROUP COMPRISING A PURIFICATION TAG

(71) Applicant: Ascendis Pharma A/S, Hellerup (DK)

(72) Inventors: Harald Rau, Dossenheim (DE); Nicola Bisek, Heidelberg (DE); Thomas Knappe, Heidelberg (DE); Romy Reimann, Heidelberg (DE); Sebastian Stark, Mannheim (DE); Samuel Weisbrod, Heidelberg (DE)

(73) Assignee: Ascendis Pharma A/S, Hellerup (DK)

( * ) Notice: Subject to any disclaimer, the term of this patent is extended or adjusted under 35 U.S.C. 154(b) by 0 days.

(21) Appl. No.: 15/027,976

(22) PCT Filed: Oct. 7, 2014

(86) PCT No.: PCT/EP2014/071386
§ 371 (c)(1),
(2) Date: Apr. 7, 2016

(87) PCT Pub. No.: WO2015/052155
PCT Pub. Date: Apr. 16, 2015

(65) Prior Publication Data
US 2016/0257739 A1 Sep. 8, 2016

(30) Foreign Application Priority Data
Oct. 8, 2013 (EP) .................................... 13187768

(51) Int. Cl.
C07K 16/22 (2006.01)
C07K 1/107 (2006.01)
C07K 1/18 (2006.01)
A61K 47/54 (2017.01)
A61K 47/64 (2017.01)

(52) U.S. Cl.
CPC ............ C07K 16/22 (2013.01); A61K 47/543 (2017.08); A61K 47/641 (2017.08); A61K 47/645 (2017.08); C07K 1/1075 (2013.01); C07K 1/18 (2013.01); C07K 2317/24 (2013.01); C07K 2317/55 (2013.01); Y02P 20/55 (2015.11)

(58) Field of Classification Search
CPC .................................................... C07K 16/22
USPC ....................................................... 546/323
See application file for complete search history.

(56) References Cited

U.S. PATENT DOCUMENTS

| 2002/0012639 | A1 | 1/2002 | Glenn, Jr. et al. |
| 2009/0124667 | A1 | 5/2009 | Ansorge et al. |
| 2011/0190486 | A1 | 8/2011 | Zilles et al. |
| 2012/0277273 | A1 | 11/2012 | Neubig et al. |

FOREIGN PATENT DOCUMENTS

| WO | WO 00/75162 | 12/2000 |
| WO | WO 02/43663 | 6/2002 |
| WO | WO 2005/099768 | 10/2005 |
| WO | WO 2006/081035 | 8/2006 |
| WO | WO 2006/136586 | 12/2006 |
| WO | WO 2007/057128 | 5/2007 |
| WO | WO 2009/095479 | 8/2009 |
| WO | WO 2011/012722 | 2/2011 |
| WO | WO 2011/089214 | 7/2011 |
| WO | WO 2011/089215 | 7/2011 |
| WO | WO 2011/089216 | 7/2011 |
| WO | WO 2013/024053 | 2/2013 |

OTHER PUBLICATIONS

International Search Report issued in corresponding International Application No. PCT/2014/071386, dated Feb. 24, 2015.
International Preliminary Report on Patentability issued in corresponding International Application No. PCT/2014/071386, dated Apr. 12, 2016.
Mark D. Ericson et al., *Synthesis of Homogenous Disulfide Cross-linked Polypeptides by Iterative Reducible Ligation*, 98(6) Biopolymers 510-517 (2012).
Sung-Gun Kim et al., *Electrostatic Interaction-Induced Inclusion Body Formation of Glucagon-Like Peptide-1 Fued with Ubiquitin and Cationic Tag*, 84(1) Protein Expression and Purification 38-46 (2012).
Barrie Kellam et al., *Transient Affinity Tags Based on the Dde Protection/Deprotection Strategy: Synthesis and Application of 2-Biotinyl- and 2-Hexanoyldimedone*, 38 Tetrahedron Letters 5391-5394 (1997).
Charles D. Conover et al, *Utility of Poly(ethylene glycol) Conjugation To Create Prodrugs of Amphotericin B.*, 14 Bioconjugate Chem. 661-666 (2003).
Peter C. De Visser et al., *A Novel, Base-Labile Fluorous Amine Protecting Group: Synthesis and Use As a Tag in the Purification of Synthetic Peptide*, 44 Tetrahedron Letters 9013-9016 (Dec. 8, 2003).
Marina Shamis al., *Z Bioactivation of self-immolative dendritic prodrugs by catalytic antibody 38C2*, 126(6) J. The Am. Chem. Soc'y 1726-1731 (Feb. 8, 2004).
Christoph Rader et al., *A Humanized Aldolase Antibody for Selective Chemotherapy and Adaptor Immunotherapy*, 322(4) J. Molecuar Biology 889-899 (Sep. 26, 2003).
Zhongping Tan et al., *Insights Into the Finer Issues of Native Chemical Ligation: An Approach to Cascade Ligations*, 49(49) Angewandte Chemie Int'l Edition 9500-9503 (Nov. 4, 2010).
Lamar Field et al., *Organic Disulfides and Related Substances. IV. Thiolsulfonates and Disulfides Containing 2-Aminoethyl Moieties*, 83(21) J. Am. Chemical Soc'y 4414-4417 (Nov. 1, 1961).
J. Kollonitsch et al., *Fluorodesulfurization. A New Reaction for the Formation of Carbon-Fluorine Bonds*, 41(19) J. Organic Chemistry 3107-3111 (Sep. 1, 1976).
Teodozyj Kolasa et al., *Symmetrical Bis(heteroarylmethoxypheny)alkylcarboxylic Acids as Inhibitors of Leukotriene Biosynthesisi*, 43(17) J. Medicinal Chemistry 3322-3334 (Aug. 9, 2000).
Lin-Hun Jiang et al., *Amino Acid Residues Involved in Gating Identified in the First Membrane-spanning Domain of the Rat P2X$_2$ Receptor*, 276(18) J. Biological Chemistry 14902-14908 (May 4, 2001).

(Continued)

Primary Examiner — Taofiq A Solola
(74) Attorney, Agent, or Firm — Haug Partners LLP

(57) ABSTRACT

The present invention relates to compounds comprising a protecting group moiety-tag moiety conjugate, a method of purification and monoconjugates obtained from such method of purification.

14 Claims, 2 Drawing Sheets

(56) References Cited

OTHER PUBLICATIONS

Figure 1:
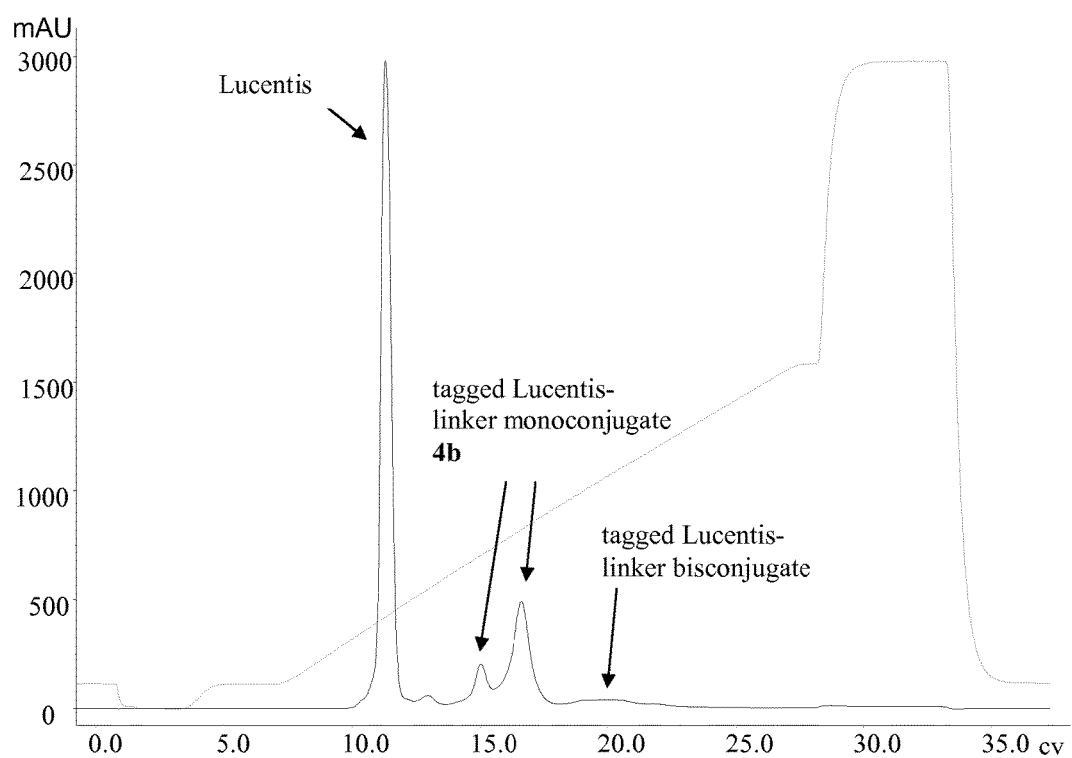

Fang Wang et al., *Triphenylbutanamines: Kinesin Spindle Protein Inhibitors with in Vivo Antitumor Activity*, 55(4) J. Medicinal Chemistry 1511-1525 (Feb. 23, 2012).
José M. Quintela et al., *A Ready One-pot Preparation for 7-Oxa(or thia)-3,4,6-triazabenz[d,e]anthracene and 7-Oxa-3,4,6,9-tetrazabenz[d,e]anthracene Derivatives)*, 52(31) Tetrahedron 10497-10506 (Jul. 29, 1996).
Goncalo J L Bernardes et al., *Site-Specific Chemical Modification of Antibody Fragments Using Traceless Cleavable Linkers*, 8(11) Nature Protocols 2079-2089 (Oct. 3, 2013).

PROTECTING GROUP COMPRISING A PURIFICATION TAG

The present application claims priority from PCT Patent Application No. PCT/EP2014/071386 filed on Oct. 7, 2014, which claims priority from European Patent Application No. EP 13187768.0 filed on Oct. 8, 2013, the disclosures of which are incorporated herein by reference their entirety.

Coupling reactions using two reagents, in which at least one is multi-functional, i.e. has more than one functional group for reaction with the other reagent, usually leads to a distribution of mono-, di-, tri- and higher conjugates, depending on the number of functional groups available. The isolation of conjugates of a specific type, for example the monomer, can be difficult or impossible, especially when the relative molecular weight difference between the different types of conjugates is small.

Accordingly, there is a need for reagents and methods that at least partially overcome the above described shortcomings.

It is therefore an object of the present invention to at least partially overcome the above-described shortcomings by providing compounds comprising protecting groups with a tag moiety that can be conjugated to high molecular weight entities, such as proteins, which allow the isolation of mono-, di- and higher conjugates.

In one aspect the present invention relates to a compound comprising a moiety of formula (I)

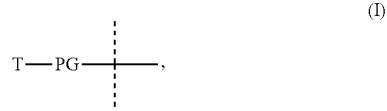

wherein
the dashed line indicates attachment to the rest of the compound;
T is a tag moiety; and
PG is a protecting group moiety.

It was now surprisingly found that the use of this protecting group comprising a tag moiety allows the isolation of, for example, monoconjugates from a mixture of mono-, di-, tri- and higher conjugates. As the tag moiety is conjugated to a protecting group, it is removed upon removal of the protecting group and is thus not present in the compound in which such tag moiety-protecting group conjugate was used.

Within the present invention the terms are used with the meaning as follows.

As used herein, the term "functional group" means a group of atoms which can react with other functional groups. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

If a functional group reacts with another functional group, the resulting chemical structure is referred to as "linkage". For example, the reaction of an amine functional with a carboxyl functional group results in an amide linkage.

As used herein, the term "reagent" means a chemical compound which comprises at least one functional group for reaction with the functional group of another reagent or moiety.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "-" indicates attachment to another moiety.

Accordingly, the phrase "in bound form" is used to refer to the corresponding moiety of a reagent, i.e. "lysine in bound form" refers to a lysine moiety which lacks one or more atom(s) of the lysine reagent and is part of a molecule.

As used herein, the term "reversible prodrug linker moiety" means a moiety which on its one end is attached to another moiety, preferably a biologically active moiety, through a reversible linkage and on another end is attached through a permanent or reversible linkage to another moiety. A "reversible linkage" is a linkage that is non-enzymatically hydrolytically degradable, i.e. cleavable, under physiological conditions (aqueous buffer at pH 7.4, 37° C.) with a half-life ranging from one hour to twelve months. In contrast, a "permanent linkage" is non-enzymatically hydrolytically degradable under physiological conditions (aqueous buffer at pH 7.4, 37° C.) with half-lives of more than twelve months.

Such reversible prodrug linker moieties are used in prodrugs. Prodrugs are compounds that undergo biotransformation before exhibiting their pharmacological effects. Prodrugs can thus be viewed as biologically active moieties connected to specialized non-toxic protective groups used in a transient manner to alter or to eliminate undesirable properties in the parent molecule. This also includes the enhancement of desirable properties in the drug and the suppression of undesirable properties. The biologically active moiety is connected to the protective group through a reversible prodrug linker.

As used herein, the term "polymer" means a molecule comprising repeating structural units, i.e. monomers, connected by chemical bonds in a linear, circular, branched, crosslinked or dendrimeric way or a combination thereof, which may be of synthetic or biological origin or a combination of both. It is understood that a polymer may for example also comprise functional groups. A polymer is referred to as a "homopolymer" if the polymer is composed of the same monomers and is referred to as a "copolymer" if the polymer is composed of different monomers.

As used herein, the term "polymeric" means a reagent or a moiety comprising one or more polymer(s).

As used herein, the term "PEG-based" refers to a moiety comprising at least 10% poly(ethylene glycol) (PEG), e.g. at least 15% PEG, at least 20% PEG, at least 25% PEG, at least 30% PEG.

As used herein, the term "tag moiety" refers to a moiety which when conjugated to a second moiety confers (a) physical and/or chemical property/properties not present in said second moiety without the tag moiety and which different physical and/or chemical property/properties allow the purification of such a conjugate.

As used herein, the term "protecting group moiety" refers to a moiety that is used for the reversible protection of functional groups during chemical reaction processes to render these functional groups unreactive in said chemical reaction processes.

As used herein, the term "spacer moiety" refers to any moiety suitable for connecting two moieties. Preferably, the term "spacer moiety" refers to a chemical bond, $C_{1-50}$ alkyl, $C_{2-50}$ alkenyl or $C_{2-50}$ alkynyl, which $C_{1-50}$ alkyl, $C_{2-50}$ alkenyl or $C_{2-50}$ alkynyl is optionally interrupted by one or more groups selected from Q, —C(O)O—; —O—; —C(O)—; —C(O)N($R^{11}$)—; —S(O)$_2$N($R^{11}$)—; —S(O)N ($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$)— and which $C_{1-50}$ alkyl, $C_{2-50}$ alkenyl or $C_{2-50}$ alkynyl is optionally substituted by one or more substituents as defined below;

wherein

Q is selected from the group consisting of phenyl; naphthyl; indenyl; indanyl; tetralinyl; $C_{3-10}$ cycloalkyl; 4- to 7-membered heterocyclyl; or 8- to 11-membered heterobicyclyl, wherein Q is optionally substituted with one or more $R^{10}$, which are the same or different; and $R^{10}$, $R^{11}$ and $R^{11a}$ are independently selected from the group consisting of H; and $C_{1-6}$ alkyl, wherein $C_{1-6}$ alkyl is optionally substituted with one or more halogen, which are the same or different.

As used herein, the term "$C_{1-4}$alkyl" alone or in combination means a straight-chain or branched alkyl group having 1 to 4 carbon atoms. If present at the end of a molecule, examples of straight-chain and branched $C_{1-4}$ alkyl groups are methyl, ethyl, n-propyl, isopropyl, n-butyl, isobutyl, sec-butyl and tert-butyl. When two moieties of a molecule are linked by the $C_{1-4}$ alkyl group, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, —CH$_2$—CH$_2$—CH$_2$—CH$_2$—, and —CH$_2$—CH$_2$—CH$_2$(CH$_3$)—. Each hydrogen atom of a $C_{1-4}$ alkyl group may be replaced by a substituent as defined below.

As used herein, the term "$C_{1-6}$ alkyl" alone or in combination means a straight-chain or branched alkyl group having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a $C_{1-6}$ alkyl group may optionally be replaced by a substituent as defined below.

As used herein, the term "$C_{1-50}$ alkyl" alone or in combination means a straight-chain or branched alkyl group having 1 to 50 carbon atoms. Each hydrogen atom of a $C_{1-50}$ alkyl group may optionally be replaced by a substituent. In each case the alkyl group may be present at the end of a molecule or two moieties of a molecule may be linked by the alkyl group.

The term "$C_{2-50}$ alkenyl" alone or in combination means a straight-chain or branched hydrocarbon residue comprising at least one carbon-carbon double bond having 2 to 50 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the alkenyl group, then an example is e.g. —CH=CH—. Each hydrogen atom of a $C_{2-50}$ alkenyl group may optionally be replaced by a substituent as defined below.

As used herein, the term "$C_{2-50}$ alkynyl" alone or in combination means a straight-chain or branched hydrocarbon residue comprising at least one carbon-carbon triple bond having 2 to 50 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a $C_{2-50}$ alkynyl group may optionally be replaced by a substituent as defined below. Optionally, one or more double bond(s) may occur.

As used herein, the term "$C_{3-10}$ cycloalkyl" means a carbocyclic ring system having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles. Each hydrogen atom of a $C_{3-10}$ cycloalkyl may optionally be replaced by a substituent as defined below.

As used herein, the term "4- to 7-membered heterocyclyl" or "4- to 7-membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 4- to 7-membered heterocycles include but are not limited to azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 4- to 7-membered heterocyclyl or 4- to 7-membered heterocycle may optionally be replaced by a substituent as defined below.

As used herein, the term "8- to 11-membered heterobicyclyl" or "8- to 11-membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

As used herein, the term "aromatic" refers to a cyclic or polycyclic moiety wherein the number of pi electrons must satisfy the Hückel rule (4n+2) and the cycle or polycycle is planar.

As used herein, the term "water-soluble" refers to a compound of which at least 1 g of said compound can be dissolved in one liter of water at 20° C. to form a homogeneous solution. The term "water-insoluble" refers to a compound of which less than 1 g of said compound can be dissolved in one liter of water at 20° C. to form a homogeneous solution.

As used herein, the term "halogen" means fluoro, chloro, bromo or iodo. Particularly preferred is fluoro or chloro.

As used herein, the term "substituted" means that one or more —H atom(s) of a moiety, compound or conjugate are replaced by a different atom or a group of atoms, which are referred to as "substituent". Suitable substituents are selected from the group consisting of halogen; —CN; —COOR$^9$; —OR$^9$; —C(O)R$^9$; —C(O)N(R$^9$R$^{9a}$); —S(O)$_2$N(R$^9$R$^{9a}$); —S(O)N(R$^9$R$^{9a}$); —S(O)$_2$R$^9$; —S(O)R$^9$; —N(R$^9$)S(O)$_2$N(R$^{9a}$R$^{9b}$); —SR$^9$; —N(R$^9$R$^{9a}$); —NO$_2$; —OC(O)R$^9$; —N(R$^9$)C(O)R$^{9a}$; —N(R$^9$)S(O)$_2$R$^{9a}$; —N(R$^9$)S(O)R$^{9a}$; —N(R$^9$)C(O)OR$^{9a}$; —N(R$^9$)C(O)N(R$^{9a}$R$^{9b}$); —OC(O)N(R$^9$R$^{9a}$); Q; C$_{1-50}$ alkyl; C$_{2-50}$ alkenyl; and C$_{2-50}$ alkynyl, wherein Q; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more group(s) selected from the group consisting of Q, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

wherein
R$^9$, R$^{9a}$, R$^{9b}$ are independently selected from the group consisting of H; Q; C$_{1-50}$ alkyl; C$_{2-50}$ alkenyl; and C$_{2-50}$ alkynyl, wherein Q; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more group(s) selected from the group consisting of Q, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

Q is selected from the group consisting of phenyl; naphthyl; indenyl; indanyl; tetralinyl; C$_{3-10}$ cycloalkyl; 4- to 7-membered heterocyclyl; or 8- to 11-membered heterobicyclyl, wherein Q is optionally substituted with one or more R$^{10}$, which are the same or different;

R$^{10}$ is halogen; —CN; oxo (=O); —COOR$^{12}$; —OR$^{12}$; —C(O)R$^{12}$; —C(O)N(R$^{12}$R$^{12a}$); —S(O)$_2$N(R$^{12}$R$^{12a}$); —S(O)N(R$^{12}$R$^{12a}$); —S(O)$_2$R$^{12}$; —S(O)R$^{12}$; —N(R$^{12}$)S(O)$_2$N(R$^{12a}$R$^{12b}$); —SR$^{12}$; —N(R$^{12}$R$^{12a}$); —NO$_2$; —OC(O)R$^{12}$; —N(R$^{12}$)C(O)R$^{12a}$; —N(R$^{12}$)S(O)$_2$R$^{12a}$; —N(R$^{12}$)S(O)R$^{12a}$; —N(R$^{12}$)C(O)OR$^{12a}$; —N(R$^{12}$)C(O)N(R$^{12a}$R$^{12b}$); —OC(O)N(R$^{12}$R$^{12a}$); or C$_{1-6}$ alkyl, wherein C$_{1-6}$ alkyl is optionally substituted with one or more halogen, which are the same or different;

R$^{11}$, R$^{11a}$, R$^{12}$, R$^{12a}$, R$^{12b}$ are independently selected from the group consisting of H; or C$_{1-6}$ alkyl, wherein C$_{1-6}$ alkyl is optionally substituted with one or more halogen, which are the same or different.

In one embodiment R$^9$, R$^{9a}$, R$^{9b}$ may be independently of each other H.

In one embodiment R$^{10}$ is C$_{1-6}$ alkyl.

In one embodiment T is phenyl.

Preferably, a maximum of 6 —H atoms of a moiety are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

As used herein, the term "peptide" refers to a chain of two to fifty amino acid monomers linked by peptide bonds. As used herein, the term "protein" refers to a chain of more than fifty amino acid monomers linked by peptide bonds. Preferably, a protein comprises less than 10000 amino acids monomers, such as no more than 5000 amino acid monomers or no more than 2000 amino acid monomers.

As used herein, the term "polyamine" refers to a moiety having at least 3 amine functional groups and preferably at most 20 amine functional groups. Even more preferably, such polyamine has 3, 4, 5, 6, 7, 8, 9 or 10 amine functional groups.

In general the term "comprise" or "comprising" also encompasses "consist of" or "consisting of".

In the following paragraphs the invention is described in further detail.

In one embodiment, T of formula (I) comprises a polymeric moiety. Preferably, T of formula (I) comprises a polymer selected from the group consisting of 2-methacryloyl-oxyethyl phosphoyl cholins, poly(acrylic acids), poly (acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(alkylene glycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropyl-methacrylamides), poly(hydroxypropyl methacrylates), poly(hydroxypropyloxazolines), poly(imino carbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

If T of formula (I) is a polymeric moiety it is preferred that T has a molecular weight of at least 1 kDa, preferably of at least 3 kDa and most preferably of at least 5 kDa. If T of formula (I) is a polymeric moiety it is preferred that it has a molecular weight of at most 1000 kDa, e.g. at most 800 kDa, at most 500 kDa, at most 250 kDa, at most 200 kDa, or at most 100 kDa.

In another embodiment, T of formula (I) comprises an affinity ligand. Preferably, T of formula (I) comprises, more preferably T is an affinity ligand moiety selected from the group consisting of 4-aminobenzamidine, 3-(2'-aminobenzhydryloxy)tropane, ε-aminocaproyl-p-chlorobenzylamide, 1-amino-4-[3-(4,6-dichlorotriazin-2-ylamino)-4-sulfophenylamino]anthraquinone-2-sulfonic acid, 2-(2'-amino-4'-methylphenylthio)-N,N-dimethylbenzylamine dihydrochloride, angiopoietin-1, aptamers, arotinoid acid, avidin, biotin, calmodulin, cocaethylene, cytosporone B, N,N-dihexyl-2-(4-fluorophenyl)indole-3-acetamide, N,N-dipropyl-2-(4-chlorophenyl)-6,8-dichloro-imidazo[1,2-a]pyridine-3-acetamide, 5-fluoro-2'-deoxyuridine 5'-(p-aminophenyl) monophosphate, S-hexyl-L-glutathione, (S,S)-4-phenyl-α-(4-phenyloxazolidin-2-ylidene)-2-oxazoline-2-acetonitrile, Pro-Leu-Gly hydroxamate, 2-(4-(2-(trifluoromethyl)phenyl) piperidine-1-carboxamido)benzoic acid, trimethyl(m-aminophenyl)ammonium chloride, urocortin III, cofactors like adenosin triphosphate, s-adenosyl methionine, ascorbic acid, cobalamine, coenzyme A, coenzyme B, coenzyme M, coenzyme Q, coenzyme F420, cytidine triphosphate, flavin mononucleotide, flavin adenine dinucleotide, glutathion, heme, lipoamide, menaquinone, methanofuran, methylcobalamine, molybdopterin, NAD+, NADP+, nucleotide sugars, 3'-phosphoadenosine-5'-phosphosulfate, pyridoxal phosphate, polyhistidines, pyrroloquinoline quinone, riboflavin, streptavidin, tetrahydrobiopterin, tetrahydromethanopterin, tetrahydrofolic acid, biotin carboxyl carrier protein (BCCP), chitin binding protein, FK506 binding proteins, FLAG tag, green fluorescent protein, glutathion-S-transferase, hemagglutinin, maltose binding protein, myc tag, NusA, protein C epitope, S-tag, strep-tag, thioredoxins, triazines and antibody fragments.

If T of formula (I) comprises an affinity ligand, it is preferred that the affinity ligand is a polyhistidine.

In another embodiment, T of formula (I) comprises a charged moiety. Preferably, T of formula (I) comprises at least one positive and/or negative charge in aqueous conditions. It is understood that the number of positive and negative charges of T is unequal to ensure that T is a charged molecule.

Preferably, T of formula (I) comprises at least one positive or negative charge in aqueous conditions, e.g. at least two positive or negative charges, at least three positive or negative charges, at least four positive or negative charges, at least five positive or negative charges, at least six positive or negative charges, at least seven positive or negative charges, at least eight positive or negative charges, at least nine positive or negative charges, at least ten positive or negative charges, at least eleven positive or negative charges, at least twelve positive or negative charges, at least thirteen positive or negative charges, at least fourteen positive or negative charges or at least fifteen positive or negative charges in aqueous conditions.

In one embodiment, T of formula (I) comprises at least one negative charge under aqueous conditions at pH 4 to 10, preferably at pH 6 to 10, such as one negative charge, two negative charges, three negative charges, four negative charges, five negative charges, six negative charges, seven negative charges, eight negative charges, nine negative charges, ten negative charges, eleven negative charges, twelve negative charges, thirteen negative charges, fourteen negative charges or fifteen negative charges under aqueous conditions at pH 4 to 10, preferably at pH 6 to 10. More preferably, T of formula (I) comprises one negative charge, two negative charges, three negative charges, four negative charges, five negative charges, six negative charges, seven negative charges or eight negative charges under aqueous conditions at pH 4 to 10, preferably at pH 6 to 10. More preferably, T of formula (I) comprises two negative charges, three negative charges, four negative charges, five negative charges or six negative charges under aqueous conditions at pH 4 to 10, preferably at pH 6 to 10.

More preferably, T of formula (I) comprises at least one positive charge under aqueous conditions at pH 3 to 9, preferably at pH 3 to 7, such as one positive charge, two positive charges, three positive charges, four positive charges, five positive charges, six positive charges, seven positive charges, eight positive charges, nine positive charges, ten positive charges, eleven positive charges, twelve positive charges, thirteen positive charges, fourteen positive charges or fifteen positive charges under aqueous conditions at pH 3 to 9, preferably at pH 3 to 7. More preferably, T of formula (I) comprises one positive charge, two positive charges, three positive charges, four positive charges, five positive charges, six positive charges, seven positive charges or eight positive charges under aqueous conditions at pH 3 to 9, preferably at pH 3 to 7. More preferably, T of formula (I) comprises two positive charges, three positive charges, four positive charges, five positive charges or six positive charges under aqueous conditions at pH 3 to 9, preferably at pH 3 to 7.

Preferably, the at least one positive charge of T of formula (I) is provided by an ammonium, phosphonium or tertiary amine. Preferably, the at least one positive charge of T of formula (I) is provided by an ammonium or phosphonium. In a specific embodiment, the at least one positive charge of T of formula (I) is provided by a tertiary amine.

Preferably, T of formula (I) comprises a polyamide comprising at least one tertiary amine, quaternary ammonium residue and/or at least one protonated ammonium residue, optionally comprising further functional groups. Preferably, such optional further functional groups are amine functional groups. Preferably, T of formula (I) comprises at least one tertiary amine or quaternary ammonium residue and/or at least one protonated ammonium residue. Even more preferably, T of formula (I) comprises four quaternary ammonium residues and/or four protonated ammonium residues.

In another preferred embodiment, T of formula (I) comprises at least one tertiary amine, such as 1, 2, 3, 4, 5 or 6 tertiary amines, and optionally comprises further functional groups. More preferably, T of formula (I) comprises 3, 4 or 5 tertiary amines and most preferably, T of formula (I) comprises 4 tertiary amines.

Preferably, T of formula (I) comprises in bound form a polyamine. More preferably, T of formula (I) comprises in bound form a polyamine selected from the group consisting of ethylene diamine, 1,3-diaminopropane, hexamethylene diamine, cadaverin, putrescin, spermine, spermidine, norspermidine and tetraethylmethylenediamine.

Even more preferably, T of formula (I) comprises a moiety of formula (a):

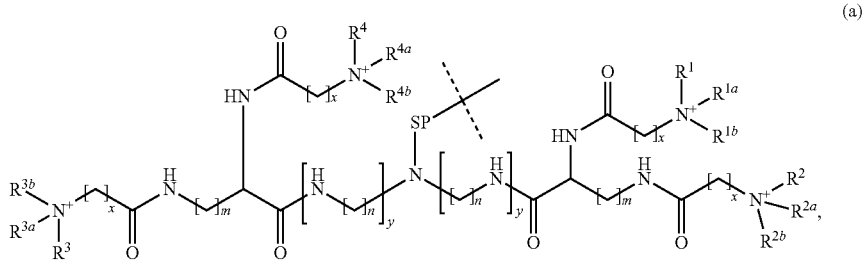

(a)

wherein
the dashed line indicates attachment to the rest of the compound, i.e. to PG of formula (I);
$R^1$, $R^{1a}$, $R^{1b}$, $R^2$, $R^{2a}$, $R^{2b}$, $R^3$, $R^{3a}$, $R^{3b}$, $R^4$, $R^{4a}$, $R^{4b}$ are independently of each other H or methyl;
each m is independently of each other 1, 2, 3, 4, 5, 6, 7, or 8;
each n is independently of each other 1, 2, 3, 4, 5, 6, 7, or 8;
each x is independently of each other 1, 2, 3, 4, 5, 6, 7 or 8:
each y is independently of each other 0, 1, 2, 3, 4, 5, 6, 7 or 8; and
SP is a spacer moiety.

Preferably, the moiety of formula (a) is symmetric, i.e. the moiety

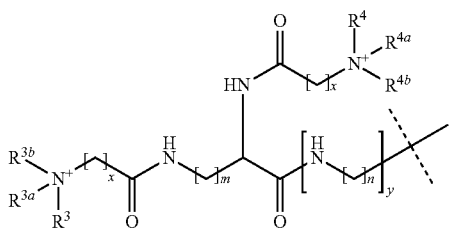

is the same as the moiety

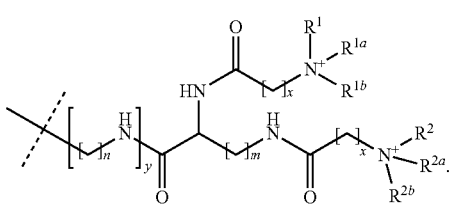

In one embodiment $R^1$, $R^{1a}$, $R^{1b}$ of formula (a) are all methyl.

In another embodiment $R^1$ of formula (a) is H and $R^{1a}$ and $R^{1b}$ of formula (a) are both methyl.

In one embodiment $R^2$, $R^{2a}$, $R^{2b}$ of formula (a) are all methyl.

In another embodiment $R^2$ of formula (a) is H and $R^{2a}$ and $R^{2b}$ of formula (a) are both methyl.

In one embodiment $R^3$, $R^{3a}$, $R^{3b}$ of formula (a) are all methyl.

In another embodiment $R^3$ of formula (a) is H and $R^{3a}$ and $R^{3b}$ of formula (a) are both methyl.

In one embodiment $R^4$, $R^{4a}$, $R^{4b}$ of formula (a) are all methyl.

In another embodiment $R^4$ of formula (a) is H and $R^{4a}$ and $R^{4b}$ of formula (a) are both methyl.

Preferably, m of formula (a) is 1, 2, 3, 4, 5 or 6. More preferably, m of formula (a) is 2, 3, 4, or 5, even more preferably, m of formula (a) is 3, 4 or 5 and most preferably, m of formula (a) is 4.

Preferably, n of formula (a) is 1, 2, 3, 4, 5 or 6. More preferably, n of formula (a) is 2, 3, 4, or 5, even more preferably, n of formula (a) is 2, 3 or 4 and most preferably, n of formula (a) is 3.

Preferably, x of formula (a) is 1, 2, 3, 4, 5 or 6. More preferably, n of formula (a) is 1, 2, 3, or 4, even more preferably, x of formula (a) is 1, 2, or 3 and most preferably, x of formula (a) is 1.

Preferably, y of formula (a) is 1, 2, 3, 4, 5 or 6. More preferably, y of formula (a) is 1, 2, 3, or 4, even more preferably, y of formula (a) is 1, 2, or 3 and most preferably, y of formula (a) is 1.

In one preferred embodiment, $R^1$, $R^{1a}$, $R^{1b}$, $R^2$, $R^{2a}$, $R^{2b}$, $R^3$, $R^{3a}$, $R^{3b}$, $R^4$, $R^{4a}$, $R^{4b}$ are methyl; m is 4; n is 3; y is 1 and x is 1.

In another preferred embodiment, $R^1$, $R^2$, $R^3$, $R^4$ are H; $R^{1a}$, $R^{1b}$, $R^{2a}$, $R^{2b}$, $R^{3a}$, $R^{3b}$, $R^{4a}$, $R^{4b}$ are methyl, m is 4; n is 3; y is 1 and x is 1.

Preferred counter ions for T of formula (I) are Cl$^-$, TFA$^-$ and SO4$^-$.

In another preferred embodiment T of formula (I) comprises a moiety of formula (b):

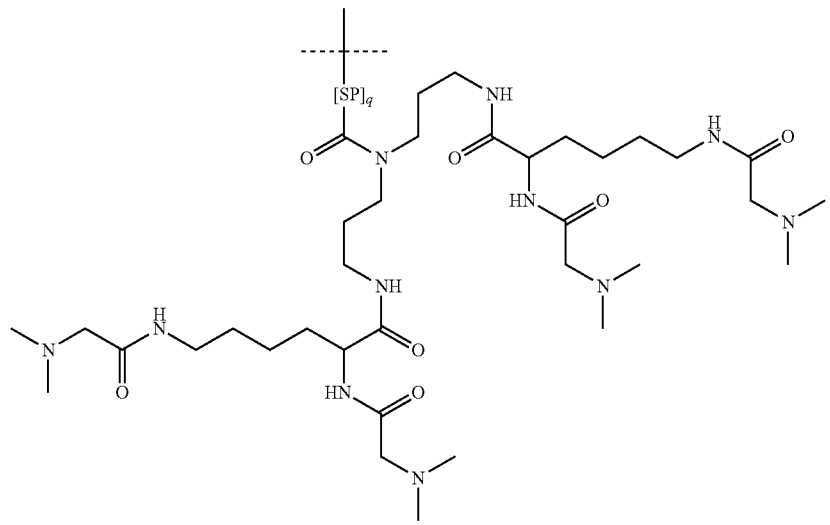

wherein the dashed line indicates attachment to PG of formula (I);

q is 0 or 1; and

SP is a spacer moiety.

PG of formula (I) is a protecting group moiety. Suitable protecting group moieties are known in the art.

If PG of formula (I) is used for the reversible protection of a thiol functional group PG is preferably selected from the group consisting of

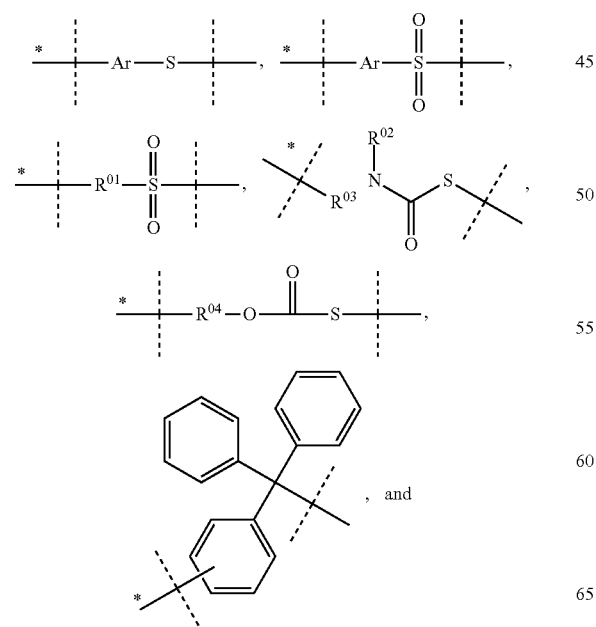

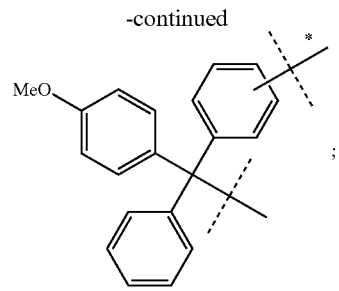

wherein the dashed line marked with an asterisk indicates attachment to T of formula (I) and the unmarked dashed line indicates attachment to the rest of the compound comprising the moiety of formula (I);

Ar is an aromatic moiety which is optionally further substituted; and $R^{01}$, $R^{03}$, $R^{04}$ are independently of each other a chemical bond or is $C_1$-$C_{50}$ alkyl; $C_{2-50}$ alkenyl; or $C_{2-50}$ alkynyl, wherein $C_1$-$C_{50}$ alkyl; $C_{2-50}$ alkenyl; and $C_{2-50}$ alkynyl are optionally substituted with one or more $R^3$, which are the same or different and wherein $C_1$-$C_{50}$ alkyl; $C_{2-50}$ alkenyl; and $C_{2-50}$ alkynyl are optionally interrupted by one or more groups selected from the group consisting of —Q—, —C(O)O—; —O—; —C(O)—; —C(O)N($R^4$)—; —S(O)$_2$N($R^4$)—; —S(O)N($R^4$)—; —S(O)$_2$—; —S(O)—; —N($R^4$)S(O)$_2$N($R^{4a}$)—; —S—; —N($R^4$)—; —OC(O)$R^4$; —N($R^4$)C(O)—; —N($R^4$)S(O)$_2$—; —N($R^4$)S(O)—; —N($R^4$)C(O)O—; —N($R^4$)C(O)N($R^{4a}$)—; and —OC(O)N($R^4R^{4a}$);

$R^{02}$ is —H; $C_1$-$C_{50}$ alkyl; $C_{2-50}$ alkenyl; or $C_{2-50}$ alkynyl, wherein $C_1$-$C_{50}$ alkyl; $C_{2-50}$ alkenyl; and $C_{2-50}$ alkynyl are optionally substituted with one or more $R^3$, which are the same or different and wherein $C_{1-50}$ alkyl; $C_{2-50}$ alkenyl; and $C_{2-50}$ alkynyl are optionally interrupted by one or more groups selected from the group consisting of —Q—, —C(O)O—; —O—; —C(O)—; —C(O)N (R⁴)—; —S(O)₂N(R⁴)—; —S(O)N(R⁴)—; —S(O)₂—; —S(O)—; —N(R⁴)S(O)₂N(R⁴ᵃ)—; —S—; —N(R⁴)—; —OC(O)R⁴; —N(R⁴)C(O)—; —N(R⁴)S(O)₂—; —N(R⁴)S(O)—; —N(R⁴)C(O)O—; —N(R⁴)C(O)N(R⁴ᵃ)—; and —OC(O)N(R⁴R⁴ᵃ)—;

Q is selected from the group consisting of phenyl; naphthyl; indenyl; indanyl; tetralinyl; C₃₋₁₀ cycloalkyl; 4- to 7-membered heterocyclyl; and 8- to 11-membered heterobicyclyl, wherein T is optionally substituted with one or more R³, which are the same or different;

R³ is halogen; —CN; oxo (=O); —COOR⁵; —OR⁵; —C(O)R⁵; —C(O)N(R⁵R⁵ᵃ); —S(O)₂N(R⁵R⁵ᵃ); —S(O)N(R⁵R⁵ᵃ); —S(O)₂R⁵; —S(O)R⁵; —N(R⁵)S(O)₂N(R⁵ᵃR⁵ᵇ); —SR⁵; —N(R⁵R⁵ᵃ); —NO₂; —OC(O)R⁵; —N(R⁵)C(O)R⁵ᵃ; —N(R⁵)S(O)₂R⁵ᵃ; —N(R⁵)S(O)R⁵ᵃ; —N(R⁵)C(O)OR⁵ᵃ; —N(R⁵)C(O)N(R⁵ᵃR⁵ᵇ); —OC(O)N(R⁵R⁵ᵃ); or C₁₋₆ alkyl, wherein C₁₋₆ alkyl is optionally substituted with one or more halogen, which are the same or different; and R⁴, R⁴ᵃ, R⁵, R⁵ᵃ, R⁵ᵇ are independently selected from the group consisting of —H; or C₁₋₆ alkyl, wherein C₁₋₆ alkyl is optionally substituted with one or more halogen, which are the same or different.

Preferably, R⁰¹ is C₁₋₆ alkyl. Even more preferably, R⁰¹ is selected from —CH₂—, —CH₂—CH₂— and —CH₂—CH₂—CH₂—.

Preferably, R⁰² is selected from H and C₁₋₆ alkyl.
Preferably, R⁰³ is C₁₋₆ alkyl.
Preferably, R⁰⁴ is C₁₋₆ alkyl.
Preferably, Ar is selected from the group consisting of

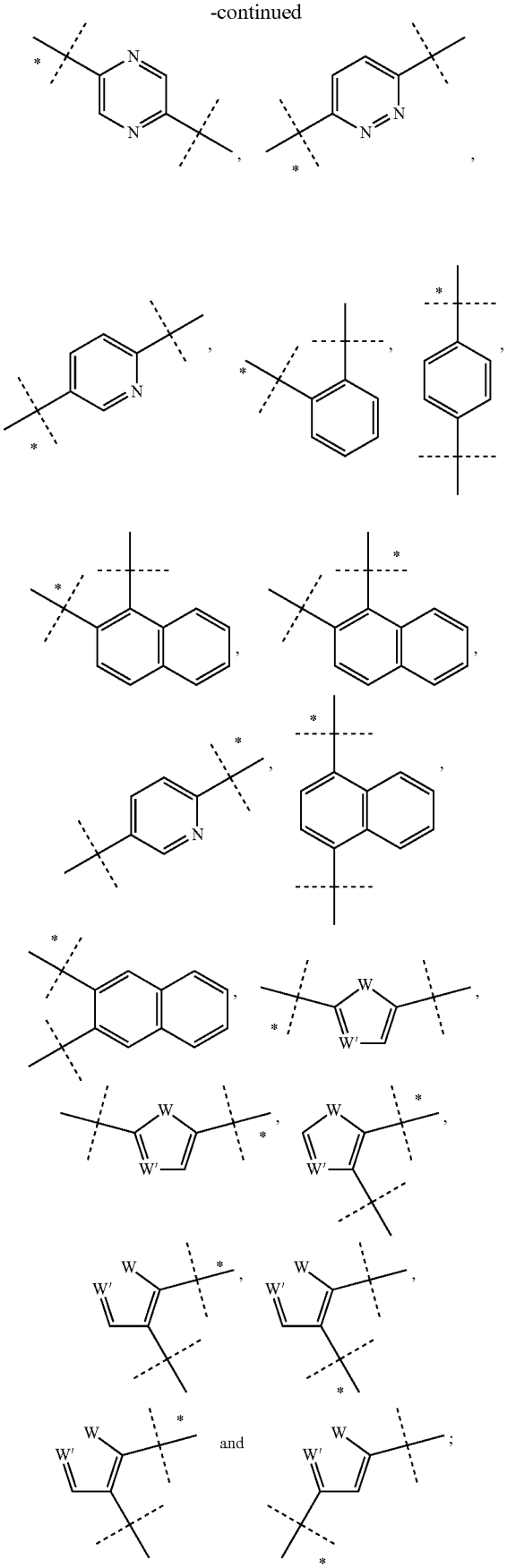

wherein
dashed lines marked with an asterisk indicate attachment to T of formula (I) and the unmarked dashed lines indicate attachment to the rest of PG of formula (I);
W is independently of each other O, S, or NR;
W' is N;
R is H, $C_{1-4}$ alkyl; and
wherein Ar is optionally substituted with one or more substituent(s) independently selected from the group consisting of $NO_2$, Cl and F.

More preferably, PG of formula (I) is selected from the group consisting of

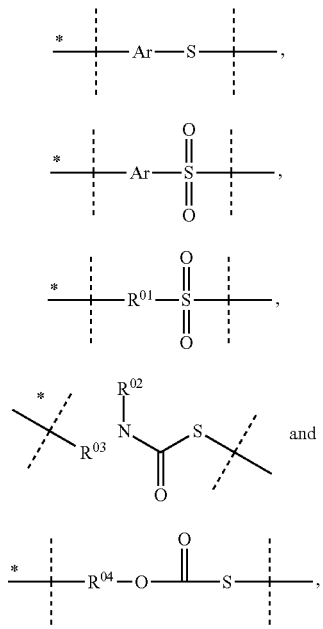

wherein
the dashed line marked with an asterisk indicates attachment to T of formula (I) and the unmarked dashed line indicates attachment to the rest of the compound of formula (I); and
Ar, $R^{01}$, $R^{02}$, $R^{03}$ and $R^{04}$ are used as above;
if PG of formula (I) is used for the reversible protection of a thiol functional group.

Preferred embodiments of Ar, $R^{01}$, $R^{02}$, $R^{03}$ and $R^{04}$ are as described above.

If PG of formula (I) is used for the reversible protection of a thiol functional group, PG is most preferably

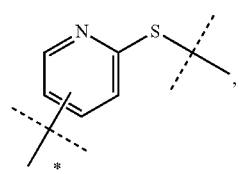

wherein
the dashed line marked with an asterisk indicates attachment to T of formula (I) and the unmarked dashed line indicates attachment to the rest of the compound comprising the moiety of formula (I).

If PG of formula (I) is used for the reversible protection of an amine functional group, PG of formula (I) preferably comprises a moiety selected from the group consisting of

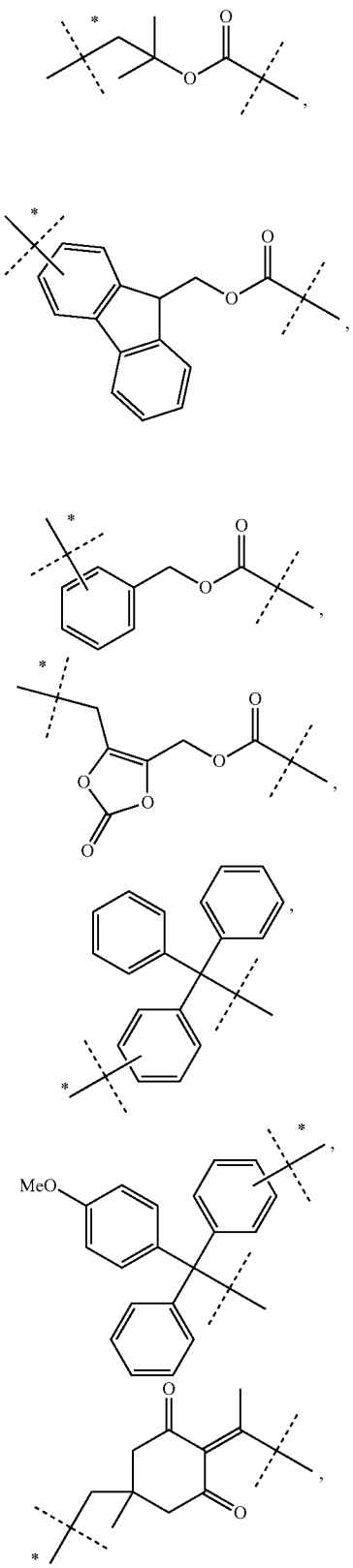

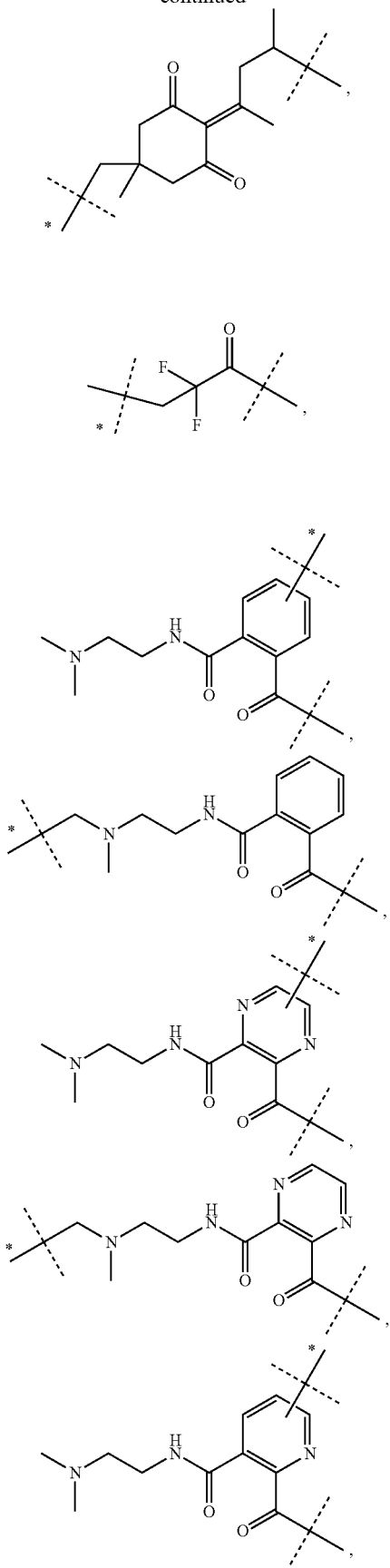
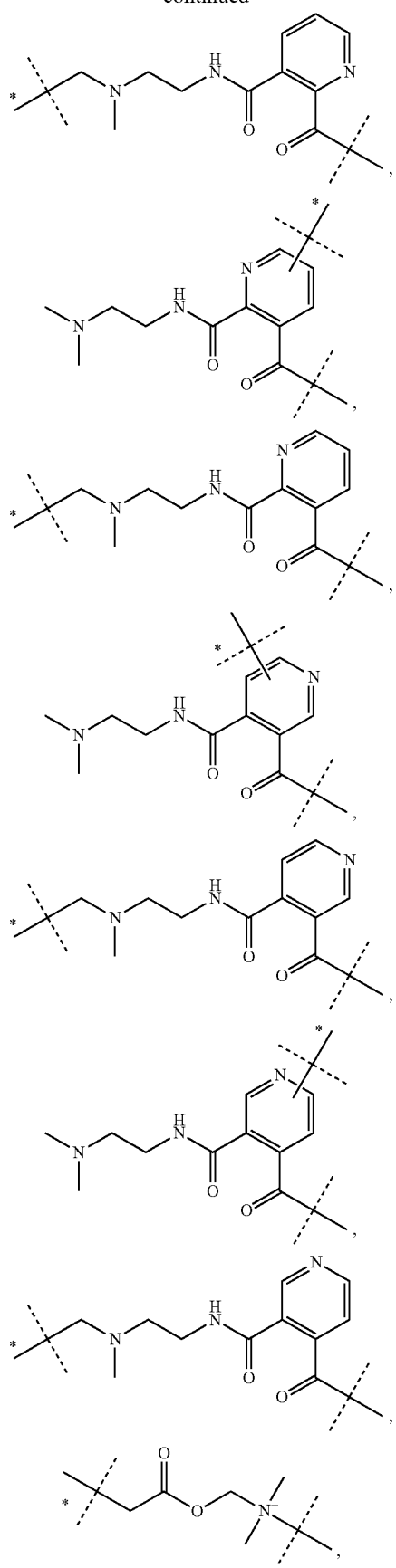

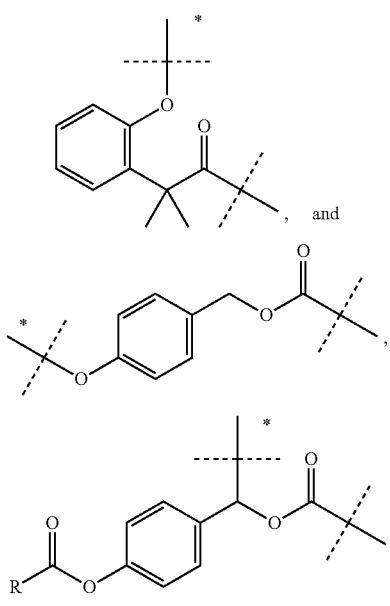

wherein
the dashed line marked with the asterisk indicates attachment to T of formula (I) and the unmarked dashed line indicates attachment to the rest of the compound comprising the moiety of formula (I); and R is $C_{1-6}$ alkyl.

More preferably, if PG of formula (I) is used for the reversible protection of an amine functional group, PG of formula (I) preferably comprises a moiety selected from the group consisting of

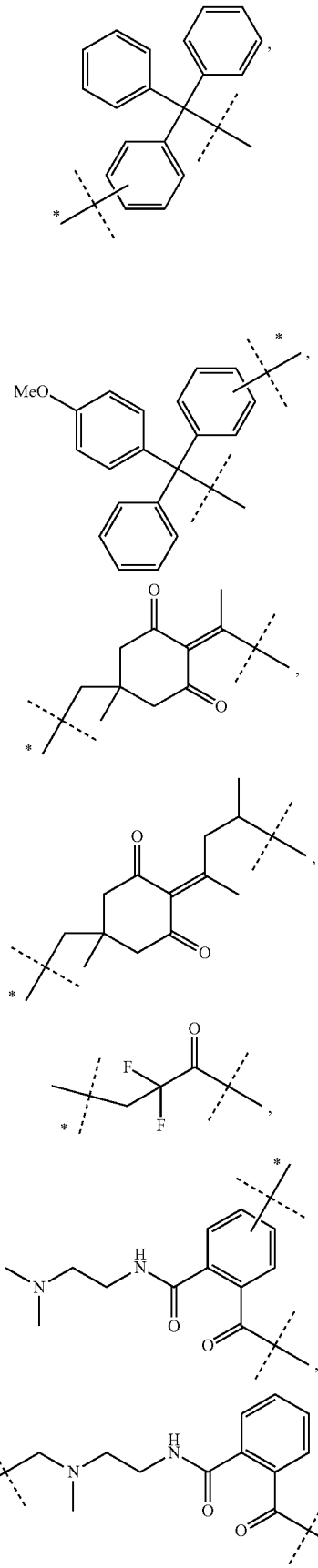

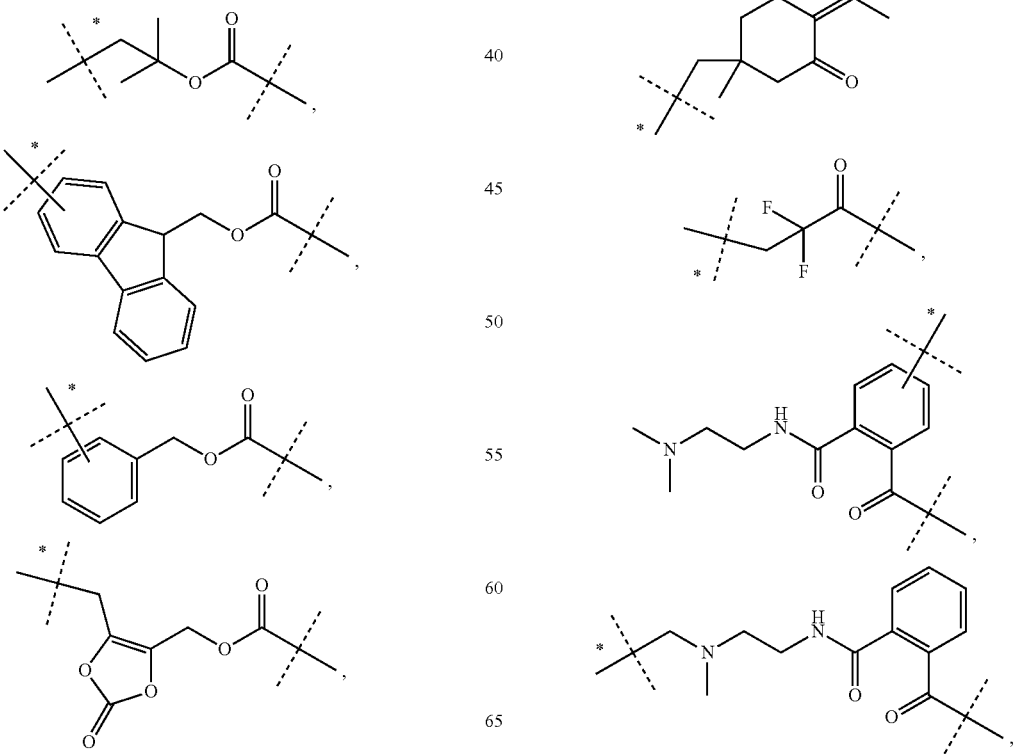

-continued

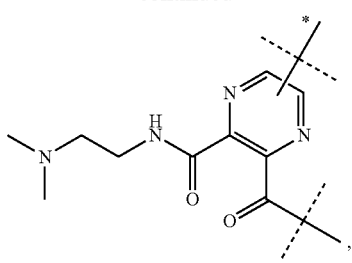

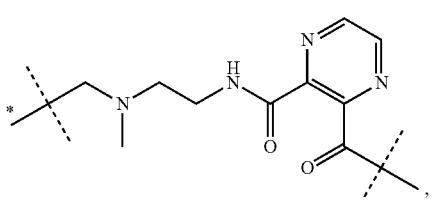

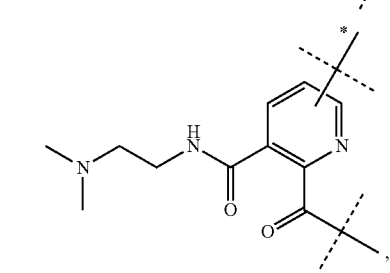

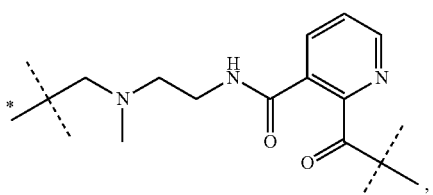

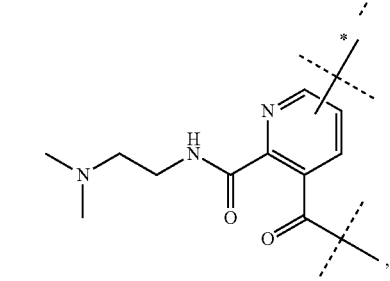

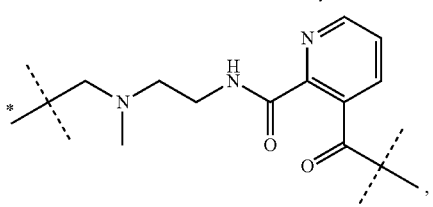

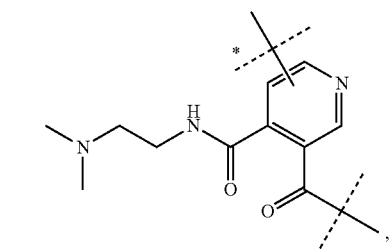

-continued

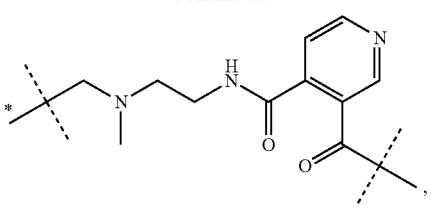

wherein
the dashed line marked with the asterisk indicates attachment to T of formula (I) and the unmarked dashed line indicates attachment to the rest of the compound comprising the moiety of formula (I).

In another preferred embodiment, if PG of formula (I) is used for the reversible protection of an amine functional group, PG of formula (I) preferably comprises a moiety of formula (Aa), (Ab) or (Ac):

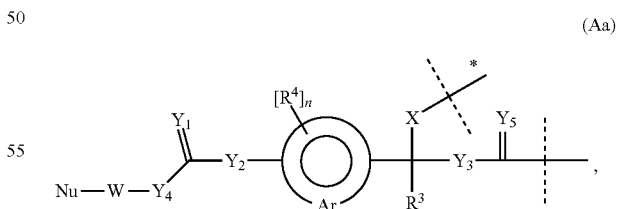

(Aa)

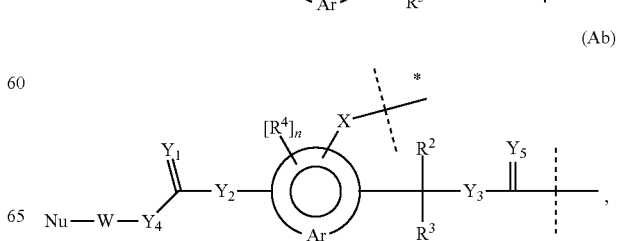

(Ab)

-continued

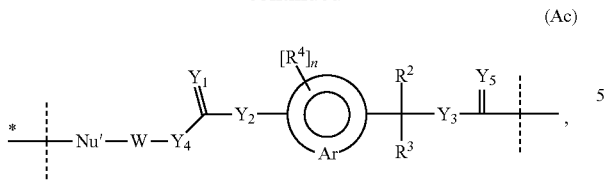

(Ac)

wherein
the dashed line marked with the asterisk indicates attachment to T of formula (I) and the unmarked dashed line indicates attachment to the nitrogen of an amine functional group;

n is 0, 1, 2, 3, or 4;

—X— is a chemical bond or a spacer;

=$Y_1$ is selected from the group consisting of =O and =S;

—$Y_2$— is selected from the group consisting of —O— and —S—;

—$Y_3$—, —$Y_5$— are independently of each other selected from the group consisting of —O— and —S—;

—$Y_4$— is selected from the group consisting of —O—, —$NR^5$— and —$C(R^6R^{6a})$—;

—$R^2$, —$R^3$, —$R^4$, —$R^5$, —$R^6$, —$R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

—W— is selected from the group consisting of $C_{1-20}$ alkyl optionally interrupted by one or more groups selected from the group consisting of —O—, —S— and —$N(R^7)$—;

—Nu is a nucleophile selected from the group consisting of —$N(R^7R^{7a})$, —$N(R^7OH)$, —$N(R^7)$—$N(R^{7a}R^{7b})$, —$S(R^7)$, —COOH,

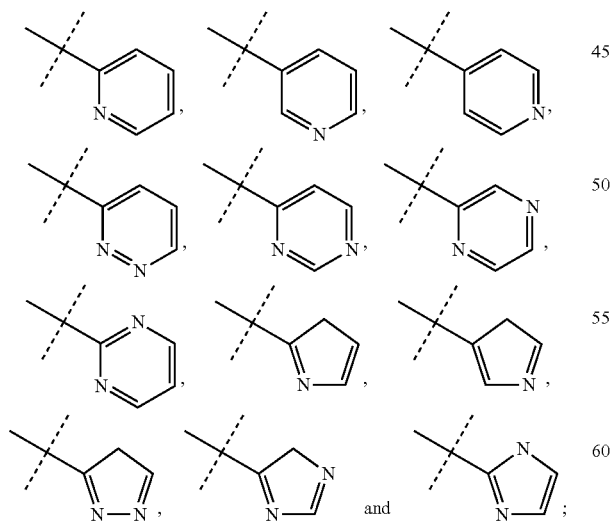

—Nu' is a nucleophile selected from the group consisting of —$N(R^7)$—, —N(OH)—, —$N(R^7)$—$N(R^{7a})$—, —S—, —C(O)O—,

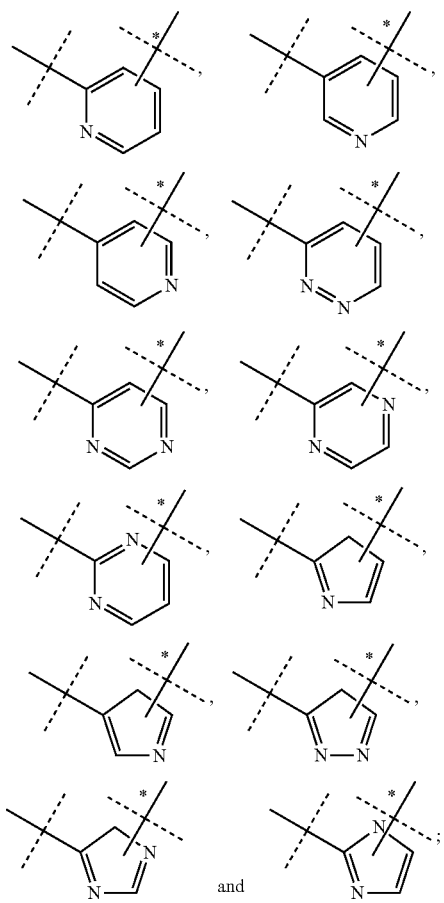

wherein
the unmarked dashed line indicates attachment to the rest of the moiety of formula (Ac) and the dashed line marked with the asterisk indicates attachment to T of formula (I);

—Ar— is selected from the group consisting of

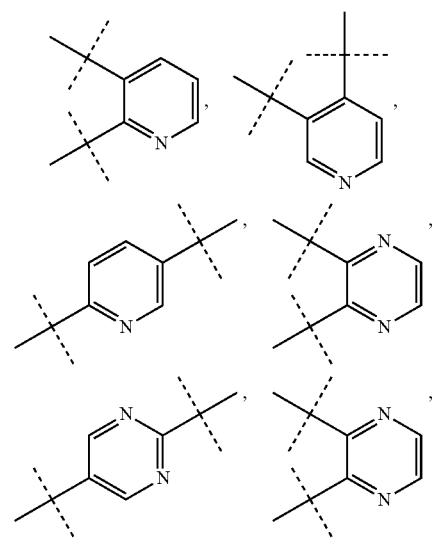

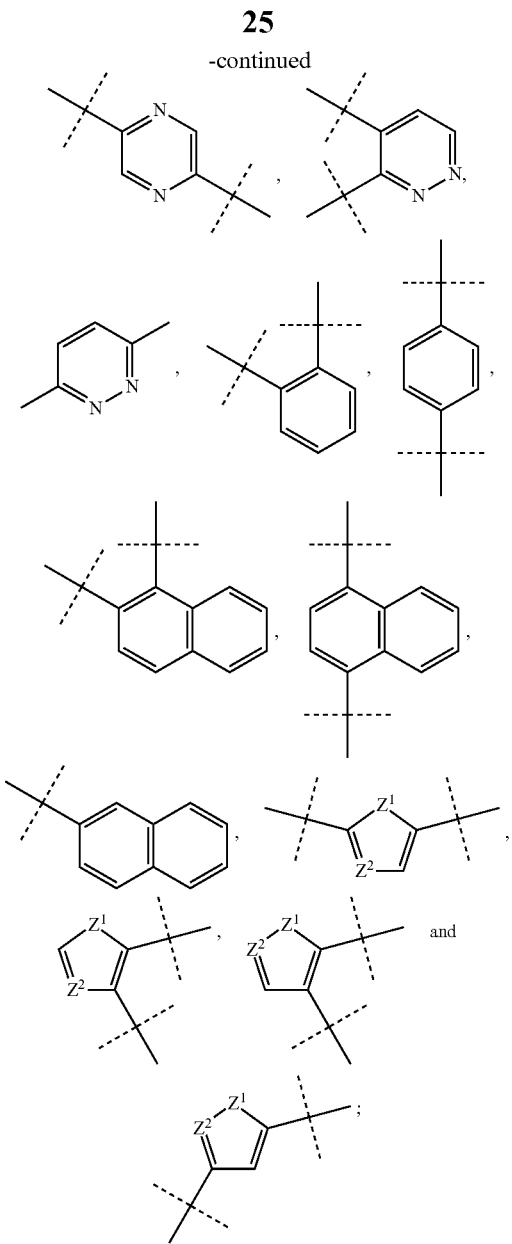

wherein
dashed lines indicate attachment to the rest of the prodrug,
—$Z^1$— is selected from the group consisting of —O—, —S— and —N($R^7$)—, and
—$Z^2$— is —N($R^7$)—; and
—$R^7$, —$R^{7a}$, —$R^{7b}$ are independently of each other selected from the group consisting of —H, $C_{1-6}$ alkyl, $C_{2-6}$ alkenyl and $C_{2-6}$ alkynyl;
wherein the moiety of formula (Aa), (Ab) and (Ac) is optionally further substituted.

It is understood that "the nitrogen of an amine functional group" refers to the amine functional group protected by the protecting group PG.

In another preferred embodiment, if PG of formula (I) is used for the reversible protection of an amine functional group, PG of formula (I) preferably comprises a moiety of formula (Ba), (Bb) and (Bc):

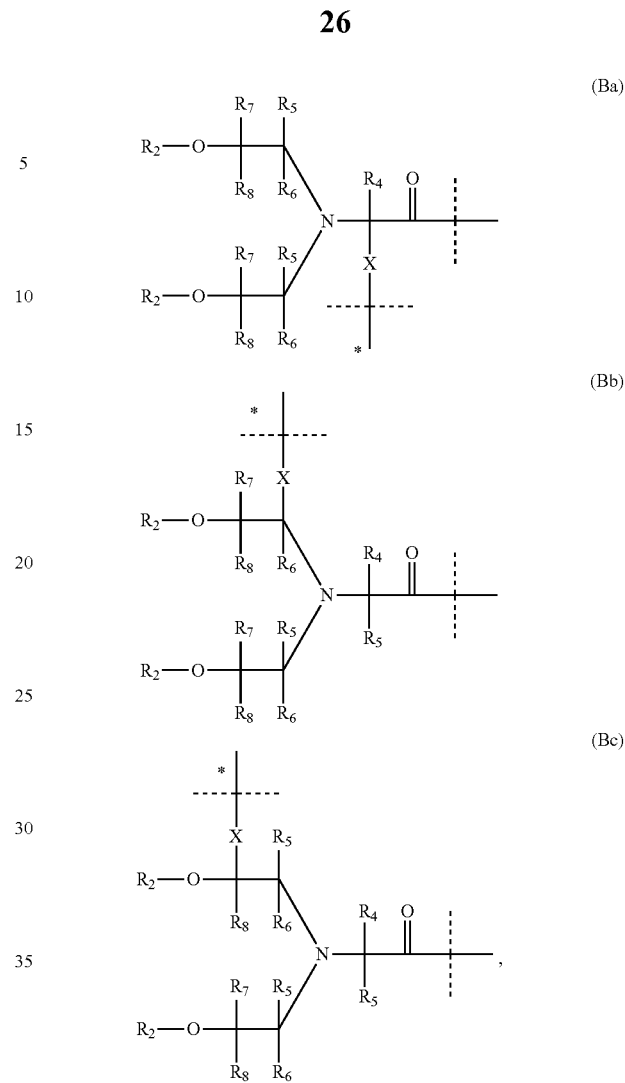

wherein
the dashed line marked with the asterisk indicates attachment to T of formula (I) and the unmarked dashed line indicates attachment to the nitrogen of an amine functional group;

X is a spacer moiety such as R13-Y1;

Y1 is O, S, NR6, succinimide, maleimide, unsaturated carbon-carbon bonds or any heteroatom-containing a free electron pair or is absent;

$R_{13}$ is selected from substituted or non-substituted linear, branched or cyclical alkyl or heteroalkyl, aryls, substituted aryls, substituted or non-substituted heteroaryls;

$R_2$ and $R_3$ are selected independently from hydrogen, acyl groups, or protecting groups for hydroxyl groups;

$R_4$ to $R_{12}$ are selected independently from hydrogen, substituted or non-substituted linear, branched or cyclical alkyl or heteroalkyl, aryls, substituted aryls, substituted or non-substituted heteroaryls, cyano, nitro, halogen, carboxy, carboxamide; and wherein the moiety of formula (Ba), (Bb) and (Bc) is optionally further substituted.

It is understood that "the nitrogen of an amine functional group" refers to the amine functional group protected by the protecting group PG.

In another preferred embodiment, if PG of formula (I) is used for the reversible protection of an amine functional group, PG of formula (I) preferably comprises a moiety of formula (C):

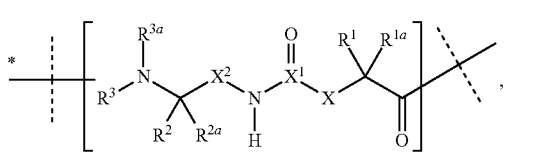

wherein
the dashed line marked with the asterisk indicates attachment to T of formula (I) and the unmarked dashed line indicates attachment to the nitrogen of an amine functional group;
X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;
$X^1$ is C; or S(O);
$X^2$ is $C(R^7, R^{7a})$; or $C(R^7, R^{7a})$—$C(R^8, R^{8a})$;
$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl;
optionally, one or more of the pair(s) $R^{1a}/R^{4a}$, $R^{1a}/R^{5a}$, $R^{4a}/R^{5a}$, $R^{4a}/R^{5a}$, $R^{7a}/R^{8a}$ form a chemical bond;
optionally, one or more of the pair(s) $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-8}$ cycloalkyl; or 4- to 7-membered heterocyclyl;
optionally, one or more of the pair(s) $R^1/R^4$, $R^1/R^5$, $R^1/R^6$, $R^4/R^5$, $R^7/R^8$, $R^2/R^3$ are joined together with the atoms to which they are attached to form a ring A;
optionally, $R^3/R^{3a}$ are joined together with the nitrogen atom to which they are attached to form a 4- to 7-membered heterocycle;
A is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl;
provided that one hydrogen of $R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$ or $R^{8a}$ is replaced by —T of formula (I); and
wherein the moiety of formula (C) is optionally further substituted.

It is understood that "the nitrogen of an amine functional group" refers to the amine functional group protected by the protecting group PG.

In another preferred embodiment, if PG of formula (I) is used for the reversible protection of an amine functional group, PG of formula (I) preferably comprises a moiety of formula (D):

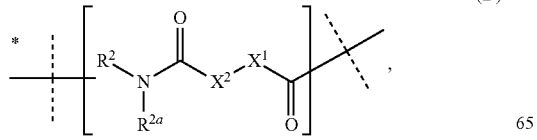

wherein
the dashed line marked with the asterisk indicates attachment to T of formula (I) and the unmarked dashed line indicates attachment to the nitrogen of an amine functional group;
$X^1$ is $C(R^1R^{1a})$ or a cyclic fragment selected from $C_{3-8}$ cycloalkyl, 4- to 7-membered heterocyclyl, phenyl, naphthyl, indenyl, indanyl, tetralinyl, or 8- to 11-membered heterobicyclyl,
wherein
in case $X^1$ is a cyclic fragment, said cyclic fragment is incorporated into $L^1$ via two adjacent ring atoms and the ring atom of $X^1$, which is adjacent to the carbon atom of the amide bond, is also a carbon atom;
$X^2$ is a chemical bond or selected from $C(R^3R^{3a})$, $N(R^3)$, O, $C(R^3R^{3a})$—$C(R^4R^{4a})$, $C(R^3R^{3a})$—$N(R^4)$, $N(R^3)$—$C(R^4R^{4a})$, $C(R^3R^{3a})$—O, or O—$C(R^3R^{3a})$,
wherein
in case $X^1$ is a cyclic fragment, $X^2$ is a chemical bond, $C(R^3R^{3a})$, $N(R^3)$ or O;
optionally, in case $X^1$ is a cyclic fragment and $X^2$ is $C(R^3R^{3a})$, the order of the $X^1$ fragment and the $X^2$ fragment within $L^1$ may be changed and the cyclic fragment is incorporated into $L^1$ via two adjacent ring atoms;
$R^1$, $R^3$ and $R^4$ are independently selected from the group consisting of H, $C_{1-4}$ alkyl and —$N(R^5R^{5a})$;
$R^{1a}$, $R^2$, $R^{3a}$, $R^{4a}$ and $R^{5a}$ are independently selected from the group consisting of H, and $C_{1-4}$ alkyl;
$R^5$ is $C(O)R^6$;
$R^6$ is $C_{1-4}$ alkyl;
optionally, one of the pairs $R^{1a}/R^{4a}$, $R^{3a}/R^{4a}$ or $R^{1a}/R^{3a}$ form a chemical bond;
provided that one hydrogen of $R^1$, $R^{1a}$, $R^2$, $R^{2a}$, $R^3$, $R^{3a}$, $R^4$, $R^{4a}$, $R^5$, $R^{5a}$ or $R^6$ is replaced by —T; and
wherein the moiety of formula (D) is optionally further substituted.

It is understood that "the nitrogen of an amine functional group" refers to the amine functional group protected by the protecting group PG.

In another preferred embodiment, if PG of formula (I) is used for the reversible protection of an amine functional group, PG of formula (I) preferably comprises a moiety of formula (E):

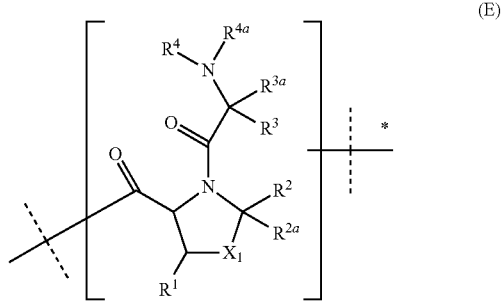

wherein
the dashed line marked with the asterisk indicates attachment to T of formula (I) and the unmarked dashed line indicates attachment to the nitrogen of an amine functional group;

$X_1$ is selected from O, S or CH—$R^{1a}$;

$R^1$ and $R^{1a}$ are independently selected from H, OH, $CH_3$;

$R^2$, $R^{2a}$, $R^4$ and $R^{4a}$ are independently selected from H and $C_{1-4}$ alkyl, $R^3$ and $R^{3a}$ are independently selected from H, $C_{1-4}$ alkyl, and $R^5$;

$R^5$ is selected from

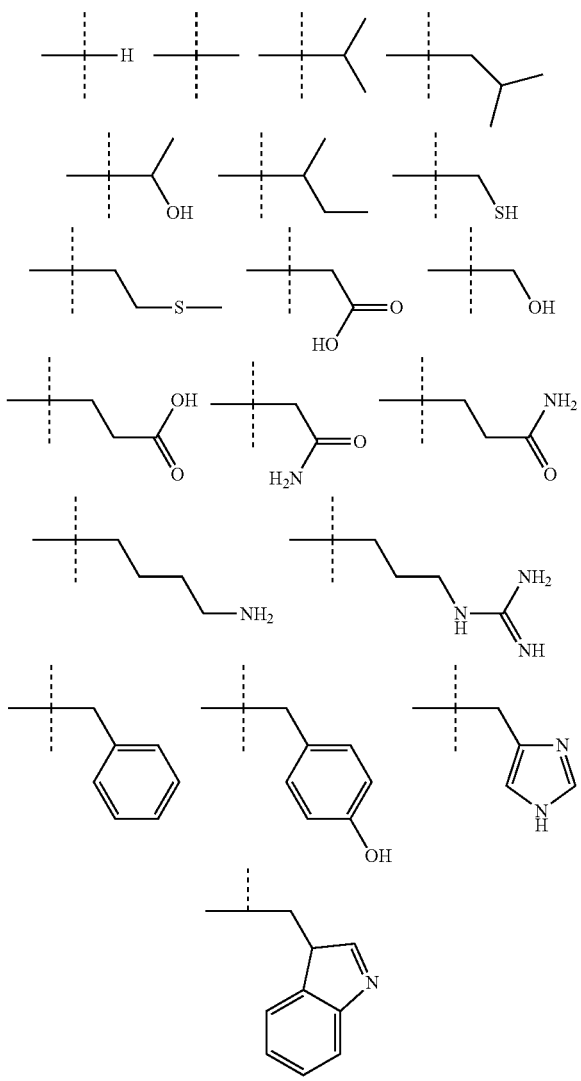

wherein
dashed lines indicate attachment to the rest of the moiety.

provided that one hydrogen of $R^1$, $R^{1a}$, $R^2$, $R^{2a}$, $R^3$, $R^{3a}$, $R^4$, $R^{4a}$ and $R^5$ is replaced by —T; and wherein the moiety of formula (E) is optionally further substituted.

It is understood that "the nitrogen of an amine functional group" refers to the amine functional group protected by the protecting group PG.

If PG of formula (I) is used for the reversible protection of a carboxyl functional group, PG is preferably selected from the group consisting of

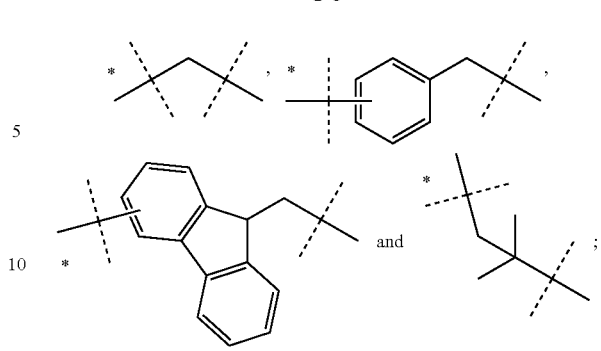

wherein
the dashed line marked with the asterisk indicates attachment to T of formula (I) and the unmarked dashed line indicates attachment to the rest of the compound comprising the moiety of formula (I).

Another aspect of the present invention is a compound comprising a moiety of formula (II)

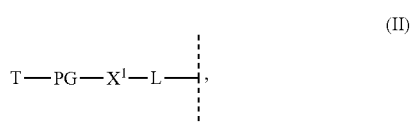

wherein
the dashed line indicates attachment to the rest of the compound;

T and PG are used as defined in formula (I);

$X^1$ is a linkage;

L is a bond or a spacer moiety.

Preferred embodiments of T and PG of formula (II) are as described for formula (I).

Preferably, $X^1$ of formula (II) is a linkage selected from the group consisting of

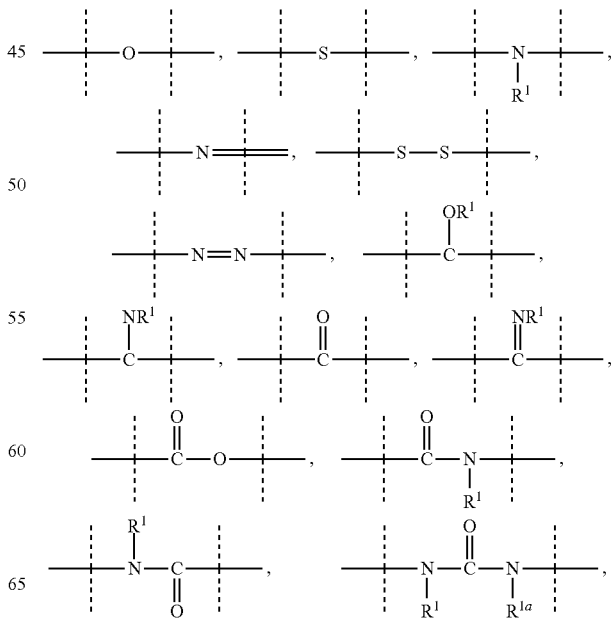

-continued

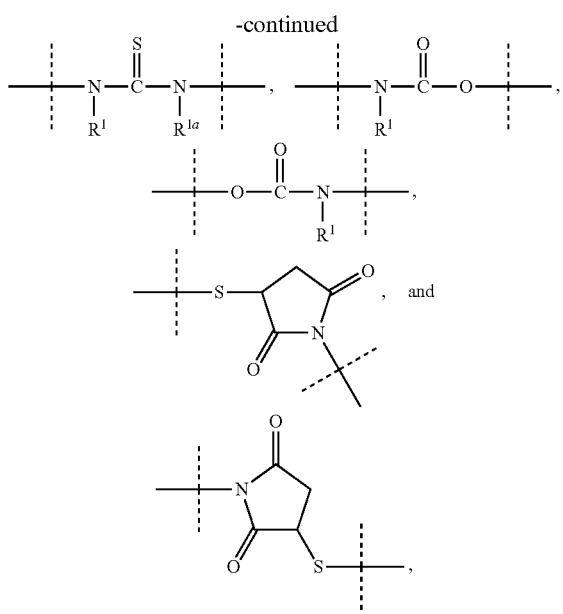

wherein
dashed lines indicate attachment to the remainder of the moiety of formula (II), and
$R^1$ and $R^{1a}$ are independently of each other selected from H and $C_{1-6}$ alkyl.

More preferably, $X^1$ of formula (II) is selected from the group consisting of

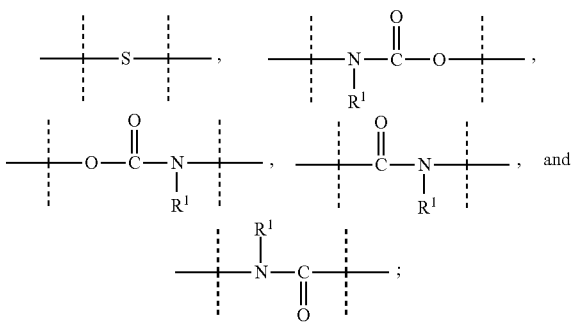

wherein
dashed lines indicate attachment to the remainder of the moiety of formula (II), and
$R^1$ and $R^{1a}$ are independently of each other selected from H and $C_{1-6}$ alkyl.

Most preferably $X^1$ of formula (II) is

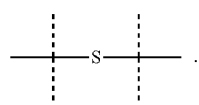

In a preferred embodiment PG of formula (II) is selected from formulas (i), (ii), (iii), (iv) or (v) and $X^1$ of formula (II) is

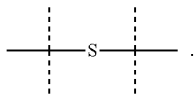

In a particularly preferred embodiment PG of formula (II) is of formula (i) and $X^1$ of formula (II) is

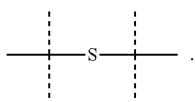

In an even more preferred embodiment PG of formula (II) is

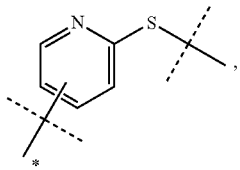

wherein
the dashed line marked with an asterisk indicates attachment to T of formula (II) and the unmarked dashed line indicates attachment to $X^1$ of formula (II);
and $X^1$ of formula (II) is

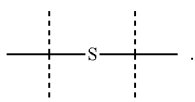

Even more preferably, PG of formula (II) is

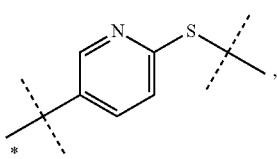

wherein
the dashed line marked with an asterisk indicates attachment to T of formula (II) and the unmarked dashed line indicates attachment to $X^1$ of formula (II);
and $X^1$ of formula (II) is

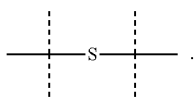

In one embodiment, L of formula (II) is a chemical bond. In another embodiment L of formula (II) is a spacer moiety. Any spacer moiety known in the art is a suitable spacer moiety, provided that no heteroatom of L is directly attached to a heteroatom of $X^1$.

In a preferred embodiment L of formula (II) is a reversible prodrug linker moiety. Suitable reversible prodrug linker moieties are known in the art. Preferred reversible prodrug linker moieties are those disclosed in WO2005/099768 A, WO2006/136586 A, WO2009/095479 A, WO2011/012722 A, WO2011/089214 A, WO2011/089216 A, WO2011/089215 A, and WO2013/024053A which are hereby incorporated by reference.

Particularly preferred is a reversible prodrug linker moiety as disclosed in WO2005/099768A. Accordingly, a preferred moiety L of formula (II) is of formula (b-i) or (b-ii)

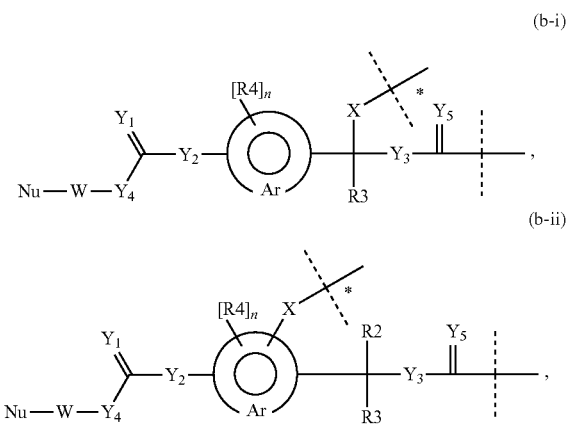

wherein the dashed line marked with the asterisk indicates attachment to $X^1$ of formula (II) and the unmarked dashed line indicates attachment to the rest of the compound comprising the moiety of formula (II), which moiety of formula (b-i) or (b-ii) is attached to the rest of the compound through an amine functional group of said rest of the compound by forming a linkage —$Y_3$—(C=$Y_5$)—NH— between L and the rest of the compound comprising the moiety of formula (II);

X of formula (b-i) or (b-ii) is a spacer moiety such as R5-$Y_6$;

$Y_1$, $Y_2$ of formula (b-i) or (b-ii) are independent of each O, S, or NR6;

$Y_3$, $Y_5$ of formula (b-i) or (b-ii) are independent of each other O or S;

$Y_4$ of formula (b-i) or (b-ii) is O, NR6 or —C(R7)(R8)-;

$Y_6$ of formula (b-i) or (b-ii) is O, S, NR6, succinimide, maleimide, unsaturated carbon-carbon bonds or any heteroatom containing a free electron pair or is absent;

R2 and R3 of formula (b-i) or (b-ii) are selected independently of each other from hydrogen, substituted or non-substituted linear, branched or cyclical alkyl or heteroalkyl, aryls, substituted aryls, substituted or non-substituted heteroaryls, cyano, nitro, halogen, carboxy, carboxyalkyl, alkylcarbonyl, or carboxamidoalkyl;

R4 of formula (b-i) or (b-ii) is selected independently from hydrogen, substituted or non-substituted linear, branched or cyclical alkyl or heteroalkyl, aryl, substituted aryl, substituted or non-substituted heteroaryl, substituted or non-substituted linear, branched, or cyclical alkoxy, substituted or non-substituted linear, branched, or cyclical heteroalkyloxy, aryloxy, or heteroaryloxy, cyano, halogen;

R5 of formula (b-i) or (b-ii) is selected from substituted or non-substituted linear, branched or cyclical alkyl or heteroalkyl, aryls, substituted aryls, substituted or non-substituted heteroaryls;

R6 of formula (b-i) or (b-ii) is selected from hydrogen, substituted or non-substituted linear, branched or cyclical alkyl or heteroalkyl, aryls, substituted or non-substituted heteroaryls;

R7 and R8 of formula (b-i) or (b-ii) are independently of each other selected from hydrogen, substituted or non-substituted linear, branched or cyclical alkyl or heteroalkyl, aryls, substituted aryls, substituted or non-substituted heteroaryls, carboxyalkyl, alkylcarbonyl, carboxamidoalkyl, cyano, or halogen;

W of formula (b-i) or (b-ii) is selected from substituted or non-substituted linear, branched or cyclical alkyls, aryls, substituted aryls, substituted or non-substituted linear, branched or cyclical heteroalkyl, substituted or nonsubstituted heteroaryls;

Nu of formula (b-i) or (b-ii) is a nucleophile;

n of formula (b-i) or (b-ii) is zero or a positive integer; and

Ar of formula (b-i) or (b-ii) is a multi-substituted aromatic hydrocarbon or a multi-substituted aromatic heterocycle.

Optionally, L of formula (b-i) or (b-ii) is further substituted.

Preferably, $Y_5$ of formula (b-i) or (b-ii) is O.

Preferably, $Y_3$ of formula (b-i) or (b-ii) is O.

Preferably, R2, R3 and R4 of formula (b-i) or (b-ii) are independently of each other selected from H, $C_{1-6}$ alkyl, $C_{2-6}$ alkenyl or $C_{2-6}$ alkynyl, which $C_{1-6}$ alkyl, $C_{2-6}$ alkenyl or $C_{2-6}$ alkynyl are optionally further substituted.

Preferably, $Y_1$ of formula (b-i) or (b-ii) is O.

Preferably, $Y_2$ of formula (b-i) or (b-ii) is O.

Preferably, $Y_4$ of formula (b-i) or (b-ii) is NR6. Preferably, R6 is H or $C_{1-6}$ alkyl.

Preferably, Ar of formula (b-i) or (b-ii) is selected from the group consisting of

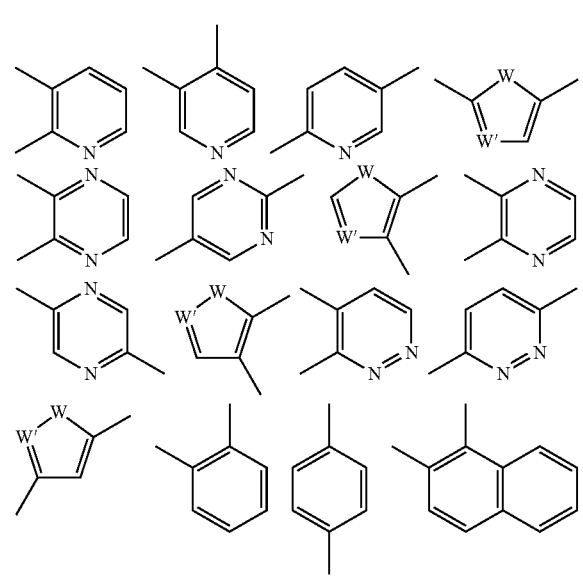

-continued

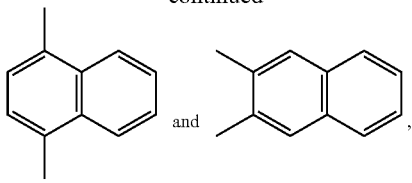

wherein
W is selected from O, S or N; and
W' is N.
Preferably, the moiety

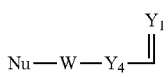

of formula (b-i) or (b-ii) is selected from the group consisting of

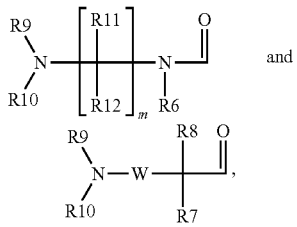

wherein
W is used as defined above;
m is 2, 3, 4, 5, 6, 7 8, 9, or 10;
R9, R10, R11 and R12 are independently of each other selected from H, $C_{1-6}$ alkyl, $C_{2-6}$ alkenyl and $C_{2-6}$ alkynyl, and which $C_{1-6}$ alkyl, $C_{2-6}$ alkenyl and $C_{2-6}$ alkynyl are optionally further substituted.

Particularly preferred is a reversible prodrug linker moiety as disclosed in WO2009/095479A. Accordingly, a preferred moiety L of formula (II) is of formula (b-iii)

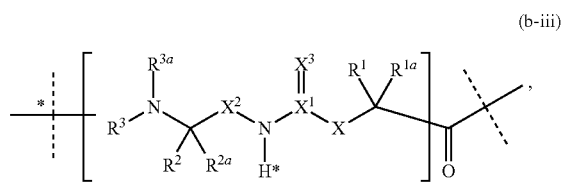

(b-iii)

wherein
the dashed line with marked with the asterisk indicates attachment to $X^1$ of formula (II) and the unmarked dashed line indicates attachment to the rest of the compound comprising the moiety of formula (II), which moiety of formula (b-iii) is attached to the rest of the compound through an amine functional group provided by said rest of the compound by forming an amide linkage between L and the rest of the compound comprising the moiety of formula (II);
X of formula (b-iii) is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;
$X^1$ of formula (b-iii) is C; or S(O);
$X^2$ of formula (b-iii) is $C(R^7, R^{7a})$; or $C(R^7, R^{7a})$—$C(R^5, R^{5a})$;
$X^3$ of formula (b-iii) is O; S; or N—CN;
$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ of formula (b-iii) are independent of each other selected from the group consisting of H; and $C_{1-4}$ alkyl;
optionally, one or more of the pairs $R^{1a}/R^{4a}$, $R^{1a}/R^{5a}$, $R^{4a}/R^{5a}$, $R^{7a}/R^{8a}$ of formula (b-iii) form a chemical bond;
optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ of formula (b-iii) are joined together with the atom to which they are attached to form a $C_{3-10}$ cycloalkyl; or 4-to 7-membered heterocyclyl;
optionally, one or more of the pairs $R^1/R^4$, $R^1/R^5$, $R^1/R^6$, $R^4/R^5$, $R^4/R^6$, $R^7/R^8$, $R^2/R^3$ of formula (b-iii) are joined together with the atoms to which they are attached to form a ring A;
optionally, $R^3/R^{3a}$ of formula (b-iii) are joined together with the nitrogen atom to which they are attached to form a 4- to 7-membered heterocycle;
A of formula (b-iii) is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl; and
wherein
the moiety of formula (b-iii) is substituted with $X^1$ of formula (II) and optionally further substituted, provided that the hydrogen marked with the asterisk in formula (b-iii) is not replaced and that $R^3$ and $R^{3a}$ of formula (b-iii) are independently of each other H or are connected to N through an $SP^3$-hybridized carbon atom.

Preferably, $X^3$ of formula (b-iii) is O.
Preferably, X of formula (b-iii) is $N(R^4)$, $X^1$ of formula (b-iii) is C and $X^3$ of formula (b-iii) is O.
Preferably, $X^2$ of formula (b-iii) is $C(R^7R^{7a})$.
It is understood that the moieties of formula (b-i), (b-ii) and (b-iii) may optionally comprise functional groups for the conjugation of further groups, such as for example polymer carriers.

Another aspect of the present invention is a compound comprising a moiety of formula (IIa)

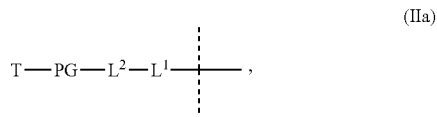

(IIa)

wherein
the dashed line indicates attachment to the rest of the compound;
T and PG are used as defined in formula (I);
$L^2$ is a chemical bond or a spacer moiety;
$L^1$ reversible prodrug linker moiety.
Preferred embodiments of T and PG of formula (IIa) are as described for formula (I).
In one embodiment $L^2$ of formula (IIa) $L^2$ is a chemical bond.
In a preferred embodiment $L^2$ of formula (IIa) is selected from —T—, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1}$)—, —N($R^{y1}$)C(O)N($R^{y1a}$)—, —OC(O)N ($R^{y1}$)—, $C_{1-50}$ alkyl, $C_{2-50}$ alkenyl, and $C_{2-50}$ alkynyl; wherein —T—, $C_{1-20}$ alkyl, $C_{2-20}$ alkenyl, and $C_{2-20}$ alkynyl are optionally substituted with one or more $R^{y2}$, which are the same or different and wherein $C_{1-20}$ alkyl, $C_{2-20}$ alkenyl, and $C_{2-20}$ alkynyl are optionally interrupted by one or more groups selected from the group consisting of —T—, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^3$)—;

$R^{y1}$ and $R^{y1a}$ are independently of each other selected from the group consisting of —H, —T, $C_{1-10}$ alkyl, $C_{2-10}$ alkenyl, and $C_{2-10}$ alkynyl; wherein —T, $C_{1-10}$ alkyl, $C_{2-10}$ alkenyl, and $C_{2-10}$ alkynyl are optionally substituted with one or more $R^{y2}$, which are the same or different, and wherein $C_{1-10}$ alkyl, $C_{2-10}$ alkenyl, and $C_{2-10}$ alkynyl are optionally interrupted by one or more groups selected from the group consisting of —T—, —C(O)O—, —O—, —C(O)—, —C(O)N($R^{y4}$)—, —S(O)$_2$N($R^4$)—, —S(O)N($R^4$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{y2}$, which are the same or different;

$R^{y2}$ is selected from the group consisting of halogen, —CN, oxo (=O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2$$R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each $R^{y3}$, $R^{y3a}$, $R^{y4}$, $R^{y4a}$, $R^{y5}$, $R^{y5a}$ and $R^{y5b}$ is independently of each other selected from the group consisting of —H, and $C_{1-6}$ alkyl; wherein $C_{1-6}$ alkyl is optionally substituted with one or more halogen, which are the same or different.

Even more preferably, $L^2$ of formula (IIa) is selected from the group consisting of —T—, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein —T—, $C_{1-20}$ alkyl, $C_{2-20}$ alkenyl, and $C_{2-20}$ alkynyl are optionally substituted with one or more $R^{y2}$, which are the same or different and wherein $C_{1-20}$ alkyl, $C_{2-20}$ alkenyl, and $C_{2-20}$ alkynyl are optionally interrupted by one or more groups selected from the group consisting of —T—, —C(O)O—, —O—, —C(O)—, —C(O)N($R^3$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

$R^{y1}$ and $R^{y1a}$ are independently selected from the group consisting of —H, —T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each $R^{y2}$ is independently selected from the group consisting of halogen, and $C_{1-6}$ alkyl; and each $R^{y3}$, $R^{y3a}$, $R^{y4}$, $R^{y4a}$, $R^{y5}$, $R^{y5a}$ and $R^{y5b}$ is independently of each other selected from the group consisting of —H, and $C_{1-6}$ alkyl; wherein $C_{1-6}$ alkyl is optionally substituted with one or more halogen, which are the same or different.

Even more preferably, $L^2$ of formula (IIa) is a $C_{1-20}$ alkyl chain, which is optionally interrupted by one or more groups independently selected from —O—, —T— and —C(O)N($R^{1aa}$)—; and which $C_{1-20}$ alkyl chain is optionally substituted with one or more groups independently selected from —OH, —T and —C(O)N($R^{y6}R^{y6a}$); wherein $R^{y6}$, $R^{y6a}$ are independently selected from the group consisting of H and $C_{1-4}$ alkyl and wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

Preferably, $L^2$ of formula (IIa) has a molecular weight in the range of from 14 g/mol to 750 g/mol.

In a preferred embodiment $L^1$ of formula (IIa) is a reversible prodrug linker moiety. Suitable reversible prodrug linker moieties are known in the art. Preferred reversible prodrug linker moieties are those disclosed in WO2005/099768 A, WO2006/136586 A, WO2009/095479 A, WO2011/012722 A, WO2011/089214 A, WO2011/089216 A, WO2011/089215 A, and WO2013/024053A which are hereby incorporated by reference.

Particularly preferred is a reversible prodrug linker moiety as disclosed in WO2005/099768A. Accordingly, a preferred moiety $L^1$ of formula (IIa) comprises a moiety of formula (b-i) or (b-ii)

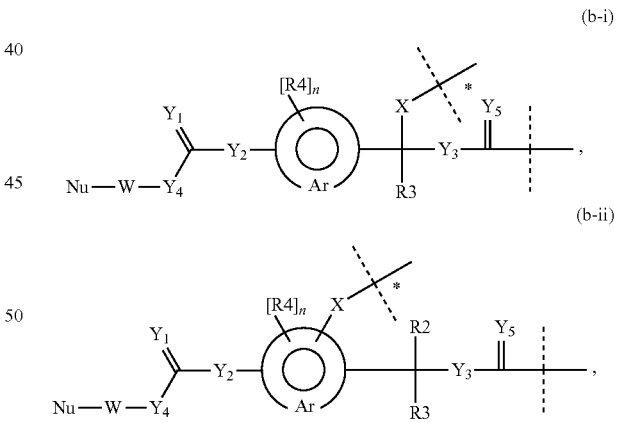

wherein the dashed line marked with the asterisk indicates attachment to $L^2$ of formula (IIa) and the unmarked dashed line indicates attachment to the rest of the compound comprising the moiety of formula (IIa), which moiety of formula (b-i) or (b-ii) is attached to the rest of the compound through an amine functional group of said rest of the compound by forming a linkage —$Y_3$—(C=$Y_5$)—NH— between L and the rest of the compound comprising the moiety of formula (IIa);

X of formula (b-i) or (b-ii) is a spacer moiety such as R5-$Y_6$;

$Y_1$, $Y_2$ of formula (b-i) or (b-ii) are independent of each O, S, or NR6;

$Y_3$, $Y_5$ of formula (b-i) or (b-ii) are independent of each other O or S;

$Y_4$ of formula (b-i) or (b-ii) is O, NR6 or —C(R7)(R8)—;

$Y_6$ of formula (b-i) or (b-ii) is O, S, NR6, succinimide, maleimide, unsaturated carbon-carbon bonds or any heteroatom containing a free electron pair or is absent;

R2 and R3 of formula (b-i) or (b-ii) are selected independently of each other from hydrogen, substituted or non-substituted linear, branched or cyclical alkyl or heteroalkyl, aryls, substituted aryls, substituted or non-substituted heteroaryls, cyano, nitro, halogen, carboxy, carboxyalkyl, alkylcarbonyl, or carboxamidoalkyl;

R4 of formula (b-i) or (b-ii) is selected independently from hydrogen, substituted or non-substituted linear, branched or cyclical alkyl or heteroalkyl, aryl, substituted aryl, substituted or non-substituted heteroaryl, substituted or non-substituted linear, branched, or cyclical alkoxy, substituted or non-substituted linear, branched, or cyclical heteroalkyloxy, aryloxy, or heteroaryloxy, cyano, halogen;

R5 of formula (b-i) or (b-ii) is selected from substituted or non-substituted linear, branched or cyclical alkyl or heteroalkyl, aryls, substituted aryls, substituted or non-substituted heteroaryls;

R6 of formula (b-i) or (b-ii) is selected from hydrogen, substituted or non-substituted linear, branched or cyclical alkyl or heteroalkyl, aryls, substituted or non-substituted heteroaryls;

R7 and R8 of formula (b-i) or (b-ii) are independently of each other selected from hydrogen, substituted or non-substituted linear, branched or cyclical alkyl or heteroalkyl, aryls, substituted aryls, substituted or non-substituted heteroaryls, carboxyalkyl, alkylcarbonyl, carboxamidoalkyl, cyano, or halogen;

W of formula (b-i) or (b-ii) is selected from substituted or non-substituted linear, branched or cyclical alkyls, aryls, substituted aryls, substituted or non-substituted linear, branched or cyclical heteroalkyl, substituted or nonsubstituted heteroaryls;

Nu of formula (b-i) or (b-ii) is a nucleophile;

n of formula (b-i) or (b-ii) is zero or a positive integer; and

Ar of formula (b-i) or (b-ii) is a multi-substituted aromatic hydrocarbon or a multi-substituted aromatic heterocycle.

Optionally, $L^1$ of formula (b-i) or (b-ii) is further substituted.

Preferably, $Y_5$ of formula (b-i) or (b-ii) is O.

Preferably, $Y_3$ of formula (b-i) or (b-ii) is O.

Preferably, R2, R3 and R4 of formula (b-i) or (b-ii) are independently of each other selected from H, $C_{1-6}$ alkyl, $C_{2-6}$ alkenyl or $C_{2-6}$ alkynyl, which $C_{1-6}$ alkyl, $C_{2-6}$ alkenyl or $C_{2-6}$ alkynyl are optionally further substituted.

Preferably, $Y_1$ of formula (b-i) or (b-ii) is O.

Preferably, $Y_2$ of formula (b-i) or (b-ii) is O.

Preferably, $Y_4$ of formula (b-i) or (b-ii) is NR6. Preferably, R6 is H or $C_{1-6}$ alkyl.

Preferably, Ar of formula (b-i) or (b-ii) is selected from the group consisting of wherein W is selected from O, S or N; and W' is N.

Preferably, the moiety $$Nu-W-Y_4 \overset{Y_1}{\underset{}{=}}$$

of formula (b-i) or (b-ii) is selected from the group consisting of wherein

W is used as defined above;

m is 2, 3, 4, 5, 6, 7 8, 9, or 10;

R9, R10, R11 and R12 are independently of each other selected from H, $C_{1-6}$ alkyl, $C_{2-6}$ alkenyl and $C_{2-6}$ alkynyl, and which $C_{1-6}$ alkyl, $C_{2-6}$ alkenyl and $C_{2-6}$ alkynyl are optionally further substituted.

Particularly preferred is a reversible prodrug linker moiety as disclosed in WO2009/095479A. Accordingly, a preferred moiety $L^1$ of formula (IIa) comprises a moiety of formula (b-iii)

(b-iii)

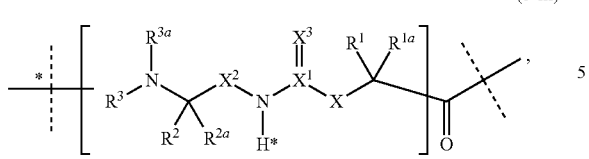

wherein
the dashed line with marked with the asterisk indicates attachment to $L^2$ of formula (IIa) and the unmarked dashed line indicates attachment to the rest of the compound comprising the moiety of formula (IIa), which moiety of formula (b-iii) is attached to the rest of the compound through an amine functional group provided by said rest of the compound by forming an amide linkage between $L^1$ and the rest of the compound comprising the moiety of formula (IIa);

X of formula (b-iii) is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ of formula (b-iii) is C; or S(O);

$X^2$ of formula (b-iii) is $C(R^7, R^{7a})$; or $C(R^7, R^{7a})$—$C(R^8, R^{8a})$;

$X^3$ of formula (b-iii) is O; S; or N—CN;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ of formula (b-iii) are independent of each other selected from the group consisting of H; and $C_{1-4}$ alkyl;

optionally, one or more of the pairs $R^{1a}/R^{4a}$, $R^{1a}/R^{5a}$, $R^{4a}/R^{5a}$, $R^{7a}/R^{8a}$ of formula (b-iii) form a chemical bond;

optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ of formula (b-iii) are joined together with the atom to which they are attached to form a $C_{3-10}$ cycloalkyl; or 4- to 7-membered heterocyclyl;

optionally, one or more of the pairs $R^1/R^4$, $R^1/R^5$, $R^1/R^6$, $R^4/R^5$, $R^4/R^6$, $R^7/R^8$, $R^2/R^3$ of formula (b-iii) are joined together with the atoms to which they are attached to form a ring A;

optionally, $R^3/R^{3a}$ of formula (b-iii) are joined together with the nitrogen atom to which they are attached to form a 4- to 7-membered heterocycle;

A of formula (b-iii) is selected from the group consisting of phenyl; naphthyl; indenyl; indanyl; tetralinyl; $C_{3-10}$ cycloalkyl; 4- to 7-membered heterocyclyl; and 8- to 11-membered heterobicyclyl; and wherein
the moiety of formula (b-iii) is substituted with $L^2$ of formula (IIa) and optionally further substituted, provided that the hydrogen marked with the asterisk in formula (b-iii) is not replaced and that $R^3$ and $R^{3a}$ of formula (b-iii) are independently of each other H or are connected to N through an $SP^3$-hybridized carbon atom.

Preferably, $X^3$ of formula (b-iii) is O.

Preferably, X of formula (b-iii) is $N(R^4)$, $X^1$ of formula (b-iii) is C and $X^3$ of formula (b-iii) is O.

Preferably, $X^2$ of formula (b-iii) is $C(R^7R^{7a})$.

It is understood that the moieties of formula (b-i), (b-ii) and (b-iii) may optionally comprise functional groups for the conjugation of further groups, such as for example polymer carriers.

Another aspect of the present invention is a conjugate of formula (III)

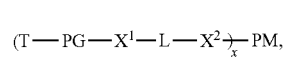

wherein
T and PG are used as defined in formula (I);
$X^1$ and L are used as defined in formula (II);
$X^2$ is a linkage;
x is 1, 2, 3, 4, 5, 6, 7, 8, 9, 10, 11, 12, 13, 14, 15, 16, 17, 18, 19 or 20; and
PM is a moiety having a molecular weight of at least 1 kDa.

Preferred embodiments of T and PG are as described for formula (I) and preferred embodiments of $X^1$ and L are as described for formula (II).

Preferably, $X^2$ of formula (III) is a linkage selected from the group consisting of

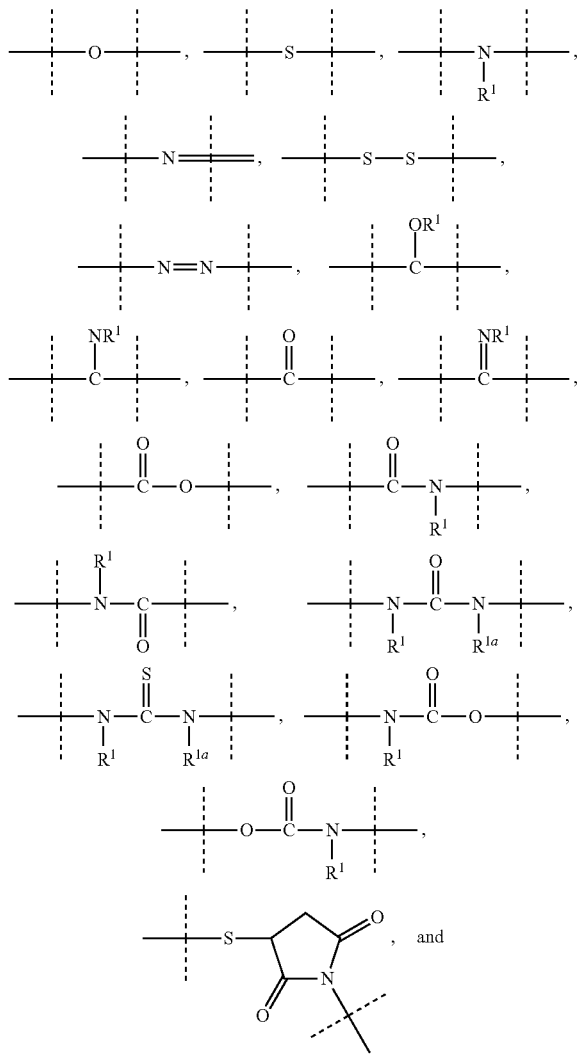

-continued

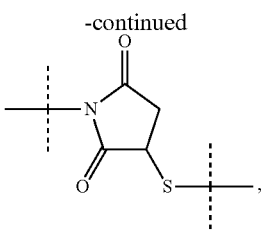

wherein
dashed lines indicate attachment to the remainder of the conjugate of formula (III), and
$R^1$ and $R^{1a}$ are independently of each other selected from H and $C_{1-6}$ alkyl.
More preferably, $X^2$ of formula (III) is selected from the group consisting of

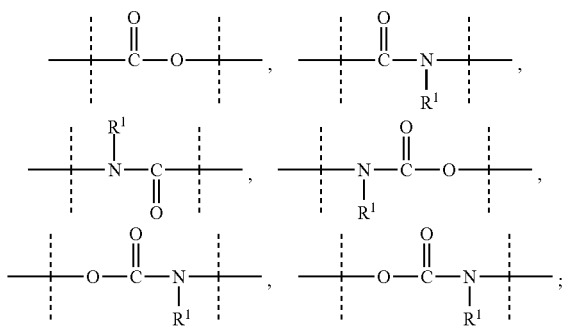

wherein
dashed lines indicate attachment to the remainder of the conjugate of formula (III), and
$R^1$ and $R^{1a}$ are independently of each other selected from H and $C_{1-6}$ alkyl.
x of formula (III) is 1, 2, 3, 4, 5, 6, 7, 8, 9, 10, 11, 12, 13, 14, 15, 16, 17, 18, 19 or 20. Preferably, x of formula (III) is 1, 2, 3, 4, 5, 6, 7, 8, 9, or 10. More preferably, x of formula (III) is 1, 2, 3, 4, 5 or 6. Even more preferably, x of formula (III) is 1, 2, 3, 4 or 5. Even more preferably, x of formula (III) is 1, 2 or 3. Most preferably, x of formula (III) is 1. If x of formula (III) is 1, the conjugate of formula (III) is referred to as a "monoconjugate".

Another aspect of the present invention is a conjugate of formula (IIIa), i.e. the compound of the present invention is of formula (IIa)

wherein
T and PG are used as defined in formula (I);
$L^1$ and $L^2$ are used as defined in formula (IIa);
x is 1, 2, 3, 4, 5, 6, 7, 8, 9, 10, 11, 12, 13, 14, 15, 16, 17, 18, 19 or 20; and
PM is a moiety having a molecular weight of at least 1 kDa.

PM of formula (III) or (IIIa) is a moiety having a molecular weight of at least 1 kDa, e.g. of at least 2 kDa, of at least 3 kDa, of at least 4 kDa, of at least 5 kDa, of at least 6 kDa, of at least 7 kDa, of at least 8 kDa, of at least 9 kDa, of at least 10 kDa, of at least 12 kDa, of at least 15 kDa, or of at least 20 kDa. Preferably, PM of formula (III) or (IIIa) has a molecular weight of at most 1000 kDa, e.g. of at most 900 kDa, of at most 800 kDa, of at most 700 kDa, of at most 600 kDa, of at most 500 kDa, of at most 400 kDa, of at most 300 kDa, of at most 200 kDa or of at most 100 kDa.

Preferably, PM of formula (III) or (IIIa) comprises a peptide or protein. More preferably, PM of formula (III) is a protein. Even more preferably, PM of formula (III) or (IIIa) is a protein selected from the group consisting of adrenocorticotropic hormone (ACTH), adenosine deaminase, agalsidase, albumin, alfa-1 antitrypsin (AAT), alfa-1 proteinase inhibitor (API), alglucosidase, alteplase, anistreplase, ancrod serine protease, antibodies (monoclonal or polyclonal and fragments or fusions), antithrombin III, antitrypsins, aprotinin, asparaginases, biphalin, bone-morphogenic proteins, calcitonin (preferably from salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides like GLP-1, glucocerebrosidase, granulocyte macrophage colony stimulating factor (GM-CSF), chorionic gonadotropin (hCG), hemoglobins, hepatitis B vaccines, hirudin, hyaluronidases, idumonidase, immune globulins, influenza vaccines, interleukines (1 alfa, 1 beta, 2, 3, 4, 6, 10, 11, 12), IL-1 receptor antagonist (IL-1ra), insulins, interferons (alfa 2a, alfa 2b, alfa 2c, beta 1a, beta 1b, gamma 1a, gamma 1b), keratinocyte growth factor (KGF), lactase, leuprolide, levothyroxine, luteinizing hormone, lyme vaccine, natriuretic peptide, pancrelipase, papain, parathyroid hormone, PDGF, pepsin, phospholipase-activating protein (PLAP), platelet activating factor alcetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrothropin, transforming growth factors, tumor necrosis factor (TNF), TNF receptor-IgG Fc, tissue plasminogen activator (tPA), transferrin, TSH, urate oxidase and urokinase.

In a preferred embodiment PM of formula (III) or (IIIa) comprises and antibody or antibody fragment.

Another aspect of the present invention is a method of purification, comprising the steps of
(i) Providing a mixture comprising a multitude of conjugates of formula (III) or (IIIa) which differ by their value for x;
(ii) Subjecting the mixture of step (i) to a purification method suitable for the tag moiety T; and
(iii) Isolating a fraction that comprises compounds of formula (III) or (IIIa) in which at least 80% of all compounds of formula (III) or (IIIa) have the same value for x.

The fraction of step (iii) comprises compounds of formula (III) or (IIIa) in which at least 80% of all compounds have the same value for x. Preferably, at least 85% of all compounds have the same value for x, more preferably, at least 90% of all compounds have the same value for x and most preferably at least 92% of all compounds have the same value for x.

In the fraction of step (iii) x is preferably 1 or 2, most preferably x is 1, i.e. the compound of formula (III) or (IIIa) is a monoconjugate.

The purification method in step (ii) depends on the tag moiety T of formula (III) or (IIIa).

If T of formula (III) or (IIIa) is a polymeric moiety with a molecular weight of at least 10% (w/w) of PM of formula (III) or (IIIa), the purification method of step (ii) is preferably size-exclusion chromatography.

If T of formula (III) or (IIIa) comprises an affinity ligand, the purification method of step (ii) is preferably affinity chromatography.

If T of formula (III) or (IIIa) comprises a charged moiety, the purification method of step (ii) is preferably ion exchange chromatography.

In a preferred embodiment T of formula (III) or (IIIa) is a charged moiety and the purification method of step (ii) is ion exchange chromatography.

Another aspect of the present invention is a monoconjugate obtainable from the method of the present invention in which x in step (iii) is 1.

FIG. 1: Chromatogram (based on absorption at 280 nm) of CIEC purification of tagged Lucentis-linker monoconjugate 4b. 4b could be separated from Lucentis as well as Lucentis-linker bisconjugate. The observed two peaks at 15 cv and 18 cv were identified as 4b by mass spectrometry. Conductivity is shown as grey curve.

Figure 2:
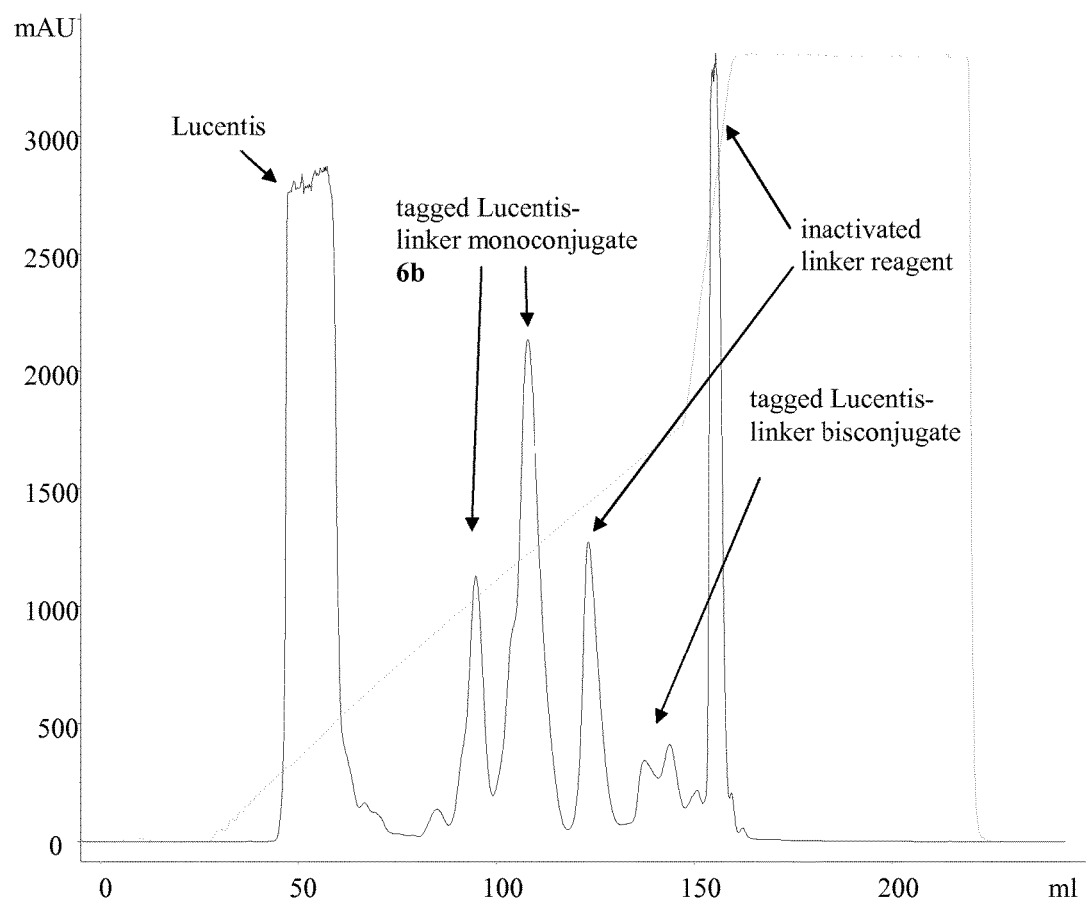

FIG. 2: Chromatogram (based on absorption at 280 nm) of CIEC purification of tagged Lucentis-linker monoconjugate 6b. 6b could be separated from Lucentis as well as tagged Lucentis-linker bisconjugate. The observed two peaks at 95 mL and 110 mL were identified as 6b by mass spectrometry. Conductivity is shown in grey.

MATERIALS AND METHODS

Lucentis and Ranibizumab are used synonymously throughout the following examples.
Materials:
TBTU, HATU, PyBOP, and Fmoc-L-Asp(OtBu)-OH were purchased from Merck Biosciences GmbH, Schwalbach/Ts, Germany.

Boc-Lys(Boc)-OSu was purchased from Senn chemicals AG, Dielsdorf, Switzerland. Fmoc-N-Me-L-Asp(OtBu)-OH was purchased from Bachem, Bubendorf, Switzerland. 1,9-bis-Boc-1,5,9-triazanonan was purchased from PolyPeptide Laboratories A/S, Hillerød, Denmark. (5-methyl-2-oxo-1,3-dioxol-4-yl)-methyl 4-nitrophenyl carbonate was purchased from Chemzon Scientific Inc., Lachine, QC, Canada.

All other chemicals were from Sigma-ALDRICH Chemie GmbH, Taufkirchen, Germany.
Methods:
Reactions were performed with dry solvents (DCM, THF, ACN, DMF, dioxane, MeOH, toluene) stored over molecular sieve purchased from Sigma-ALDRICH Chemie GmbH, Taufkirchen, Germany. Generally, reactions were stirred at room temperature and monitored by HPLC/MS or TLC.

RP-HPLC was done on a 100×20 mm or 100×40 mm C18 ReproSil-Pur 300 ODS-3 5µ column (Dr. Maisch, Ammerbuch, Germany) or XBridge BEH300 C18 OBD Prep 10 µm 30×150 mm or 5 µm 10×150 mm (Waters, Eschborn, Germany) connected to a Waters 600 or 2535 HPLC System and Waters 2487 or 2489 Absorbance detector, respectively. Linear gradients of solution A (0.1% TFA in H$_2$O) and solution B (0.1% TFA in acetonitrile) were used. HPLC fractions containing product were combined and lyophilized.

Flash chromatography purifications were performed on an Isolera One system from Biotage AB, Sweden, using Biotage KP-Sil silica cartridges and n-heptane, ethyl acetate, and methanol as eluents. Products were detected at 254 nm. For products showing no absorbance above 240 nm fractions were screened by LC/MS.

Analytical ultra-performance LC (UPLC) was performed on a Waters Acquity system equipped with a Waters BEH300 C18 column (2.1×50 mm, 1.7 µm particle size) coupled to a LTQ Orbitrap Discovery mass spectrometer from Thermo Scientific.

HPLC-Electrospray ionization mass spectrometry (HPLC-ESI-MS) was performed on a Waters Acquity UPLC with an Acquity PDA detector coupled to a Thermo LTQ Orbitrap Discovery high resolution/high accuracy mass spectrometer or Waters Micromass ZQ both equipped with a Waters ACQUITY UPLC BEH300 C18 RP column (2.1× 50 mm, 300 Å, 1.7 µm, flow: 0.25 mL/min; solvent A: UP-H$_2$0+0.04% TFA, solvent B: UP-Acetonitrile+0.05% TFA.

Buffer exchange was performed on a HiTrap or HiPrep column (GE Healthcare) connected to an Aekta Purifier system.

Cationic ion exchange chromatography was performed either on a Source 15S 4.6/100 column or on a Source 15 S 6 mL column connected to an Aekta Purifier system using 20 mM MES, pH 5.7 and 20 mM MES, 500 mM NaCl, pH 5.7 as mobile phase A and B, respectively.

Example 1

Synthesis of Linker Reagent 1k

Linker reagent 1k was synthesized according to the following scheme:

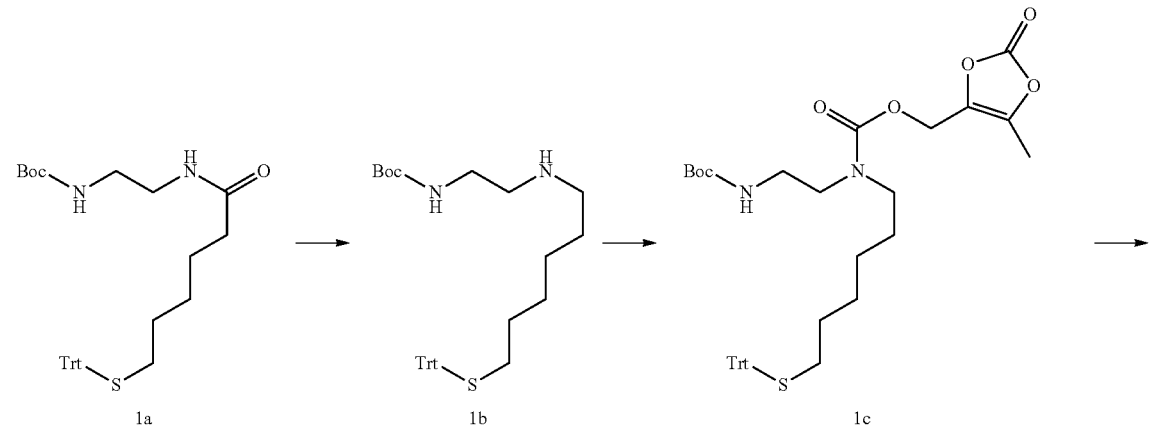

47
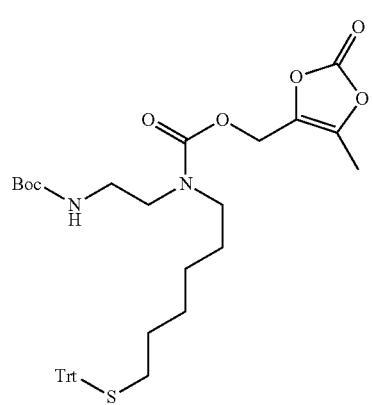
-continued
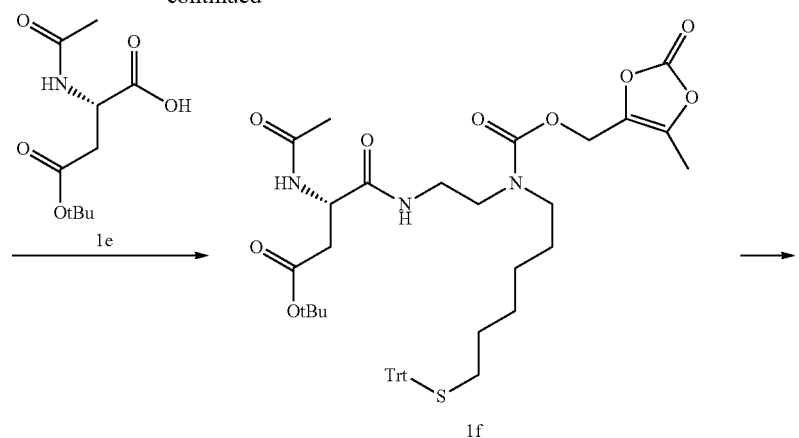
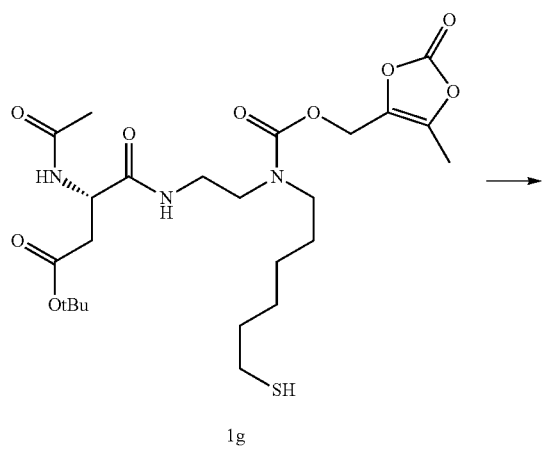
48
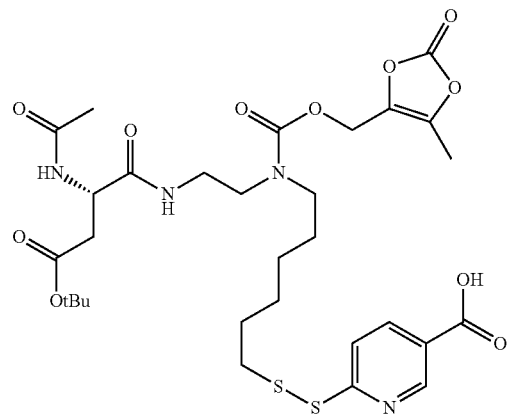
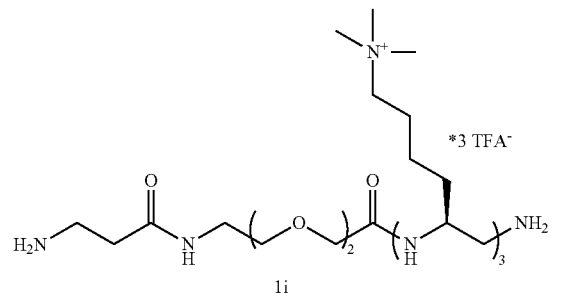

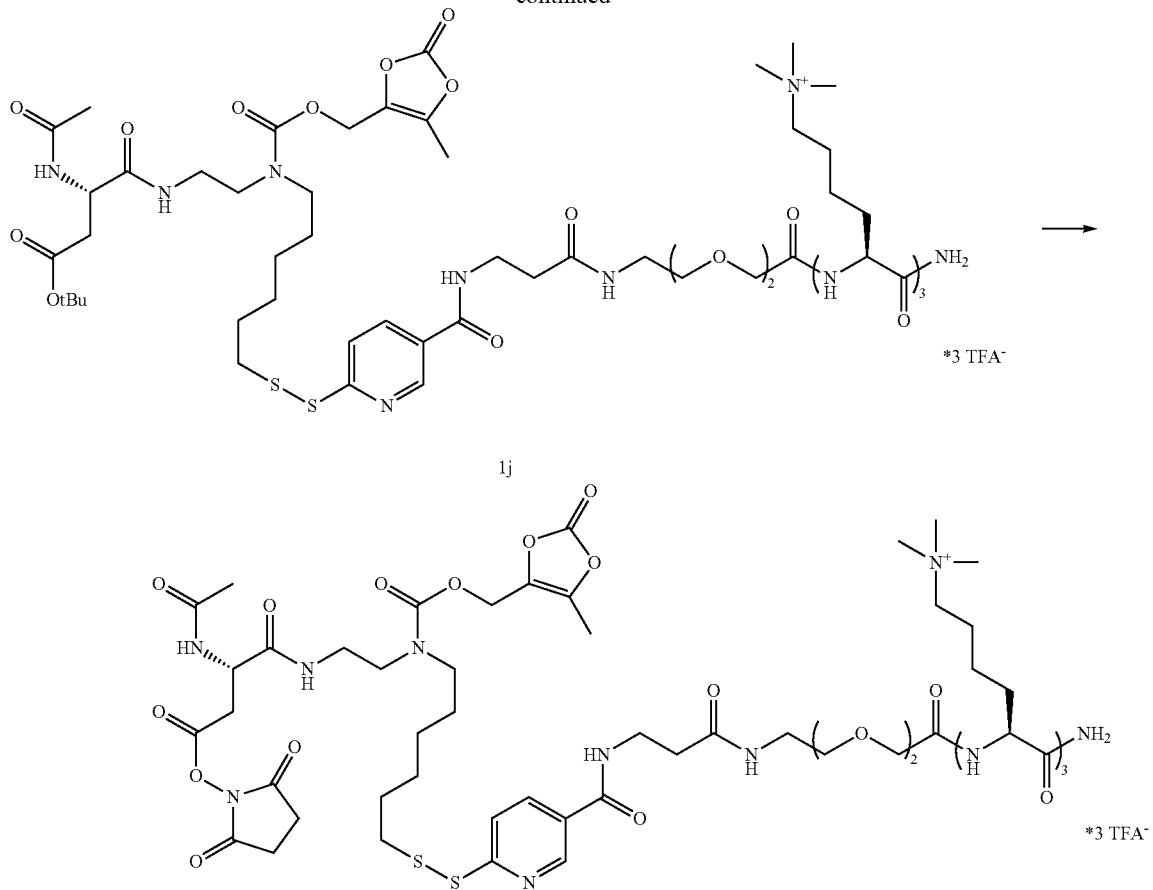

N-Boc-ethylenediamine (0.77 g, 4.8 mmol) was dissolved in DCM (15 mL) and 6-tritylmercaptohexanoic acid (2.25 g, 5.76 mmol) and PyBOP (3.0 g 5.76 mmol) were added with stirring. DIPEA (2.52 ml, 14.4 mmol) was added and the reaction stirred for 1 h. The reaction was diluted with diethyl ether (150 mL) and washed with slightly basic brine (3×30 mL, prepared from 100 mL brine and 3 mL 0.1 M aq. NaOH). The organic phase was washed once more with brine (30 mL), dried over $Na_2SO_4$ and concentrated in vacuo and purified using flash chromatography to give 1a as a white foam. Yield: 2.55 g (4.79 mmol, 99%) MS: m/z 555.24=$[M+Na]^+$, (calculated=555.27).

1a (2.55 g, 4.79 mmol) was dissolved in THF (26 mL) and transferred into an oven-dried argon filled round-bottom flask. Borane-THF complex in THF (1 M, 17.7 mL, 17.71 mmol) was added and the reaction stirred for 15 h. MeOH (5.4 mL) was added slowly and N,N'-dimethyl ethylenediamine (3.11 mL, 28.8 mmol) was added and the reaction refluxed for 2.5 h. After cooling the reaction was diluted with ethyl acetate and washed with sat. sodium bicarbonate solution (2×125 mL) and brine (1×125 mL). The organic phase was dried over $Na_2SO_4$, concentrated in vacuo to give 1b which was used without further purification in the next step. Yield: 2.38 g (4.59 mmol, 96%) MS: m/z 519.27=$[M+H]^+$, (calculated=519.31).

1b (1.19 g 2.29 mmol) was dissolved in DCM and (5-methyl-2-oxo-1,3-dioxol-4-yl)-methyl 4-nitrophenyl carbonate (1.02 g, 3.44 mmol) and 2,4,6-collidine (1.36 mL, 10.32 mmol) were added and the reaction stirred for 23 h. The reaction was concentrated in vacuo and purified using flash chromatography to give 1c. Yield: 1.19 g (1.77 mmol, 79%) MS: m/z 697.18=$[M+Na]^+$, (calculated=697.29).

1c (0.5 g, 0.74 mmol) was dissolved in DCM (2.5 mL) and triphenylmethanol (0.19 g, 0.74 mmol) and TFA (2.5 mL) were added. The reaction was stirred for 40 min, concentrated in a stream of argon and dried in vacuo (<0.1 mbar). The residue was dissolved in ACN/water (7:3 v/v, 10 mL) and purified by RP-HPLC to give 1d (0.50 g, 0.84 mmol, 114%). MS: m/z 575.33=$[M+H]^+$, (calculated=575.26).

2-Chlorotritylchloride resin (1.22 mmol/g, 0.87 g, 1 mmol) was weighted into a 10 ml syringe with frit. The resin was swollen with 5 mL DCM and washed with DCM (5×4 mL). N-Fmoc-L-Asp(OtBu)-OH (1.1 g, 2.7 mmol) was dissolved in DCM (5 mL) and DIPEA (0.66 mL, 3.78 mmol) was added and the solution drawn into the syringe. The syringe was agitated for 1 h. MeOH (0.5 mL) was drawn into the syringe and the syringe agitated for 15 min. The resin was washed 5 times with DCM (4 mL) and 5 times with DMF (5 mL). The resin was agitated 3 times for 5 min with DMF:DBU:piperidine (96:2:2 v/v/v 4 mL). The resin was washed 5 times with DMF (4 mL). Acetic anhydride (0.51 mL, 5.4 mmol) and DIPEA (1.9 mL, 10.8 mmol) were dissolved in DMF (6 mL) and the solution was drawn into the syringe and the syringe agitated for 15 min. The resin was washed 5 times with DMF (4 mL), 5 times with DCM (4 mL). A solution of HFIP/DCM (1/4 v/v, 5 mL each) were drawn into the syringe and the syringe agitated 3 times for 10 min. The collected filtrates were concentrated in vacuo. Crude 1e (0.29 g, 1.23 mmol, 114%) was used without further purification in the next step. MS: m/z 254.38=[M+Na]$^+$, (calculated=254.12).

1e (65 mg, 0.28 mmol) was dissolved in DCM (3 mL) and PyBOP (0.18 g, 0.34 mmol) and DIPEA (0.15 mL, 0.84 mmol) were added. 1d (0.18 g, 0.31 mmol) was dissolved in DCM (3 mL) and added to the reaction. The reaction was stirred for 1h and concentrated in vacuo. The residue was purified by RP-HPLC to give 1f (97 mg, 0.12 mmol, 44%). MS: m/z 810.02=[M+Na]$^+$, (calculated=810.34).

1f (200 mg, 0.25 mmol) were dissolved in HFIP (5 mL) and TES (0.3 mL) and AcOH (0.3 mL) were added and the reaction stirred for 75 min. The solvents were removed in a stream of argon and the residue dissolved in ACN/water (9:1 v/v) and purified by RP-HPLC to give 1g (95 mg, 0.17 mmol, 68%). MS: m/z 568.28=[M+Na]$^+$, (calculated=568.23).

1g (95 mg, 0.17 mmol) was dissolved in ACN/water (1:1 v/v, 3 mL) and 6, 6'-dithiodinicotinic acid (107 mg, 0.35 mmol) was added. ACN (1 mL) was added to improve solubility and pH 7.4 sodium phosphate buffer (0.5 M, 1.5 mL) was added to adjust the pH. The reaction was stirred for 45 min and the reaction mixture directly purified by RP-HPLC to give 1h (103 mg, 0.15 mmol, 85%). MS: m/z 699.14=[M+H]$^+$, (calculated=699.22).

Fmoc protected Sieber amide resin (0.74 mg, 0.45 mmol, 0.61 mmol/g) was weighed into a 20 mL syringe equipped with a filter frit. The resin was swollen with DMF (2×10 mL, 2×15 min) and the Fmoc protecting group was afterwards removed by shaking the resin with DMF/piperidine/DBU (98:1:1, v/v/v, 2×8 mL, 1×5 min, 1×10 min). After intensive washing with DMF (10×8 mL) the first coupling was accomplished by incubating the resin for 1 h with a solution of Fmoc-L-Lys(Me$_3$Cl)—OH (0.5 g, 1.12 mmol), HOBt (0.17 g, 1.12 mmol), HATU (0.43 g, 1.12 mmol) and DIPEA (0.78 mL, 4.5 mmol) in DMF (4 mL). After intense washing with DMF (10×8 mL) the terminal Fmoc protecting group was removed by treating the resin with DMF/piperidine/DBU (98:1:1, v/v/v, 2×8 mL, 1×5 min, 1×10 min). The resin was washed with DMF (10×8 mL) and the second amino acid was attached by incubating the resin for 1 h with a solution of Fmoc-L-Lys(Me$_3$Cl)—OH (0.5 g, 1.12 mmol), HOBt (0.17 g, 1.12 mmol), TBTU (0.36 g, 1.12 mmol) and DIPEA (0.78 mL, 4.5 mmol) in DMF (4 mL). After washing with DMF (10×8 mL) the Fmoc protecting group was removed by incubation with DMF/piperidine/DBU (98:1:1, v/v/v, 2×8 mL, 1×5 min, 1×10 min). After washing with DMF (10×8 mL) the amount of resin was halved and one part of the resin was kept aside. The next coupling was accomplished by incubating the resin for 1 h with a solution of Fmoc-L-Lys(Me$_3$Cl)—OH (0.25 g, 0.56 mmol), HOBt (86 mg, 0.56 mmol), TBTU (0.18 g, 0.56 mmol) and DIPEA (0.39 mL, 2.25 mmol) in DMF (2 ml). After washing with DMF (10×4 mL) and subsequent deprotection with DMF/piperidine/DBU (98:1:1, v/v/v, 2×4 mL, 1×5 min, 1×10 min) and washing with DMF (10×4 mL) the resin was treated with a coupling solution of Fmoc-Ado-OH (0.22 g, 0.56 mmol), HOBt (86 mg, 0.56 mmol), TBTU (0.18 g, 0.56 mmol) and DIPEA (0.39 mL, 2.25 mmol) in DMF (2 mL). The resin was washed with DMF (10×4 mL) and deprotected with DMF/piperidine (4:1 v/v, 2×4 mL, 1×15 min, 1×10 min). After washing with DMF (10×4 mL) the last coupling was accomplished by shaking the resin for 90 min with a solution of Boc-β-Ala-OH (85 mg, 0.44 mmol), HATU (0.17 g, 0.44 mmol), HOAt (0.9 ml, 0.5 M in DMF) and DIPEA (0.25 mL, 1.43 mmol) in DMF (1 mL). After washing with DMF (10×4 mL) and DCM (10×4 mL) the peptide was cleaved off the resin by treating with TFA/HFIP/TIPS/H$_2$O (1:94:2.5:2.5, v/v/v/v, 2×5 mL, 2×40 min). The resulting solutions were combined and the volume was reduced to a total of 5 mL by a stream of N$_2$. To the concentrated solution was added ice-cold diethyl ether. The formed suspension was centrifuged at 5000×G at 0° C. for ten minutes and the supernatant was discarded, The residue was dissolved in 5 mL ACN/H$_2$O/TFA (1:1:0.002 v/v/v) and it was purified by RP-HPLC to give ii as a colorless, glassy solid after lyophilization. Yield: 80 mg, 67 μmol (1×TFA 3×TFA$^-$ salt), 30%. MS: m/z=972.56=[M+2×TFA$^-$]$^+$, (calculated 972.56).

1h (32 mg, 46 μmol) was dissolved in DMF (1.14 mL) and 1i (47 mg, 53 μmol) was added. To this mixture HATU (18 mg, 48 μmol) and DIPEA (67 μL, 0.38 mmol) were added and it was stirred for 90 min. The reaction was quenched by addition of AcOH (67 μL) and water was added to a total volume of 5 mL. The resulting solution was purified by RP-HPLC to give 1j as colorless oil. Yield: 41 mg, 22 μmol (1×TFA 3×TFA$^-$ salt), 48%. MS: m/z=769.97=[M+TFA$^-$]$^{2+}$, (calculated 769.89).

1j (41 mg, 22 μmol) was dissolved in TFA (1 mL) and stirred for 30 min before TFA was removed by a stream of N$_2$. The residue was dissolved in H$_2$O/ACN/TFA 1:1:0.002 (1.5 mL), frozen and lyophilized to give the free acid as colorless oil containing additional amounts of TFA. Yield: 63 mg, max. 22 μmol (3×TFA$^-$ salt), quant. MS: m/z=685.03=[M–H]$^{2+}$ (calculated 684.86). To a solution of the free acid (21 mg, 12 μmol) in DMF (0.5 mL) was added Boc-1-tert-butoxy-1,2-dihydroisoquinoline (36 mg, 0.12 mmol). The mixture was stirred for 5 h before NHS (21 mg, 0.18 mmol) was added. The reaction was quenched by addition of AcOH (7 μL) after 20 min. The mixture was cooled to 0° C. and was afterwards diluted with H$_2$O/ACN/TFA 1:1:0.002 to a total volume of 2.5 mL. This solution was purified by RP-HPLC to give 1k as colorless oil. Yield: 11 mg, 5.2 μmol (1×TFA 3×TFA$^-$ salt), 43%. MS: m/z=790.37=[M+TFA$^-$]$^{2+}$, (calculated 790.37).

Example 2
Synthesis of Purification Tag 2e
Purification tag 2e was synthesized according to the following scheme:
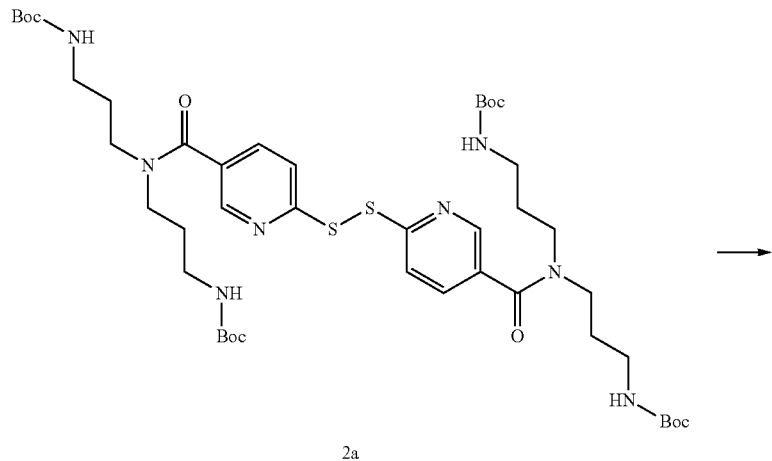
2a
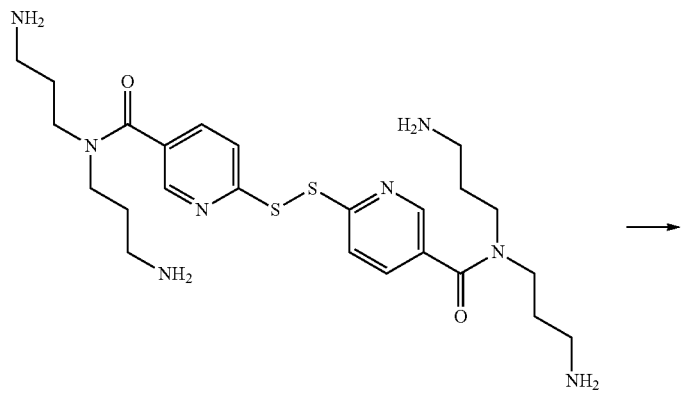
2b
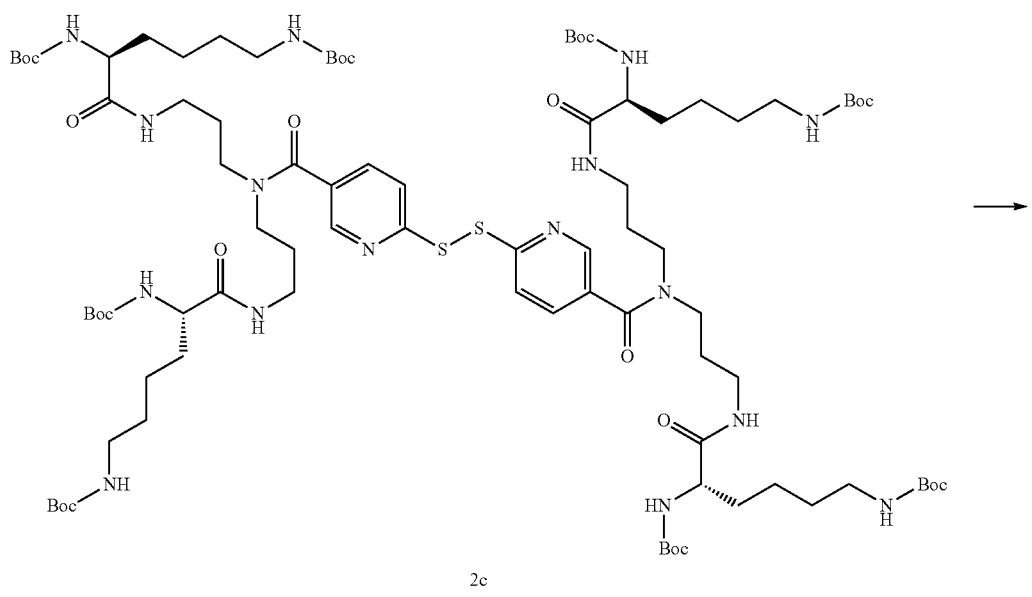
2c

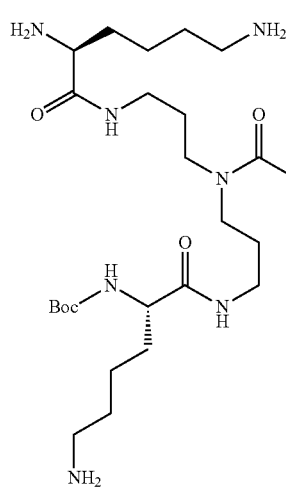

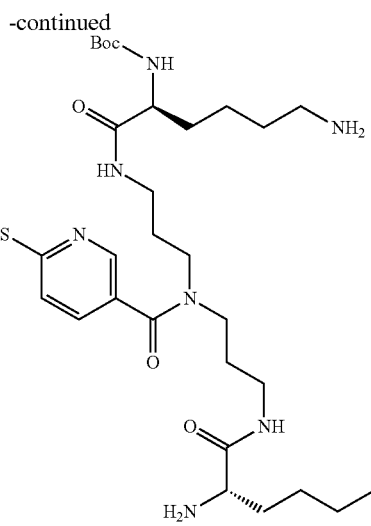

2d

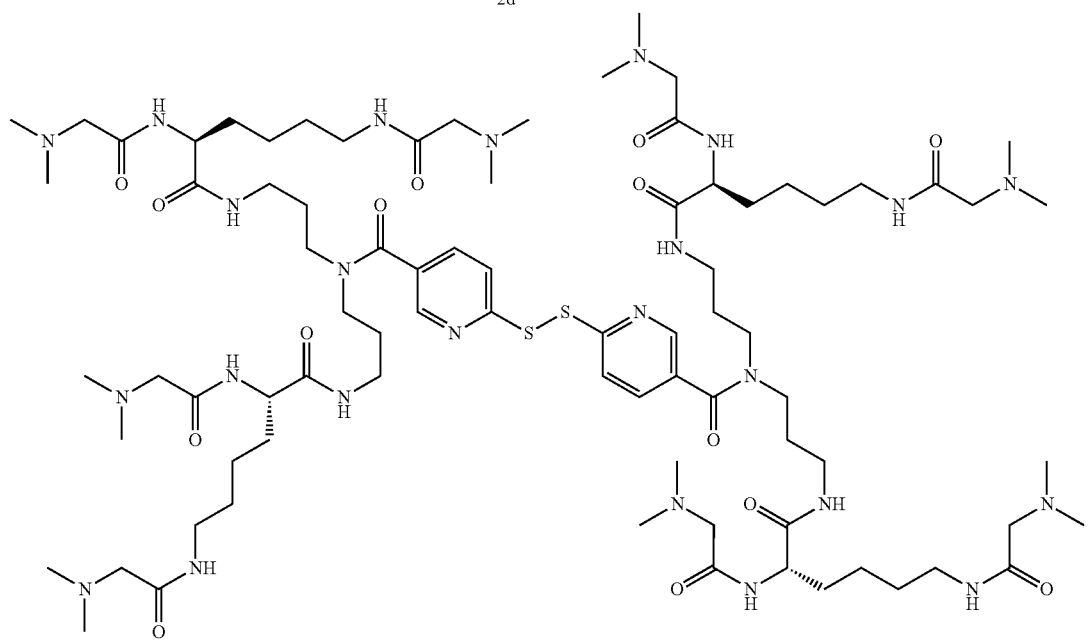

2e

To a suspension of 6,6'-dithiodinicotinic acid (0.62 g, 2 mmol) in ACN (20 mL) were added PyBOP (2.08 g, 4 mmol) and DIPEA (1.29 g, 1.74 mL, 10 mmol) and the mixture was stirred for 1 min. The obtained brown solution was added to a solution of 1,9-bis-Boc-1,5,9-triazanonane (1.99 g, 6 mmol) in a mixture of ACN (20 mL) and DMF (5 mL) and stirred for 2 h. The reaction mixture was diluted with EtOAc (150 mL) and the organic layer was washed with aq. HCl (10 mM, 5×100 mL), saturated NaHCO$_3$ solution (3×100 mL) and brine (100 mL), subsequently. After drying over MgSO$_4$ and filtration, the solvent was removed in vacuo and the crude residue was purified by flash chromatography to give 2a (1.92 g, max. 2 mmol) as a light yellow foam. The product contains a small, non-separable amount of tripyrrolidine phosphoramide, which is removed in the next step. MS: m/z=935.47=[M+H]$^+$, (calculated 935.47).

2a (1.92 g, max. 2 mmol) was dissolved in TFA (10 mL) and the solution was stirred for 10 min. The reaction mixture was added dropwise to ice-cold diethyl ether (160 mL) to precipitate the product. The resulting suspension was centrifuged at 7000×G and 2° C. for 3 min. The supernatant was discarded and the precipitate was dissolved in methanol (10 mL). This solution was added drop-wise to ice-cold diethyl ether (160 mL) and the formed suspension was centrifuged at 7000×G and 2° C. for 3 min. After discarding the supernatant the precipitation procedure was accomplished two more times like described above. The remaining oily precipitate was dried in vacuo to give 2b (1.77 g, 1.45 mmol (6×TFA salt), 73%) as a light brown, very hygroscopic powder. MS: m/z=535.26=[M+H]$^+$, (calculated 535.26).

To a solution of 2b (3.30 g, 2.7 mmol) in DMF (90 mL) were added DIPEA (5.4 mL, 31 mmol) and Boc-L-Lys (Boc)-OSu (5.62 g, 12.7 mmol). The mixture was stirred for 14 h before it was diluted with ethyl acetate (600 mL). The organic layer was washed with aq. HCl (10 mM, 5×300 mL), sat. NaHCO$_3$ solution (3×300 mL) and brine (300 mL) and was dried over MgSO$_4$. After filtration the solvent was removed in vacuo and the crude residue was purified by flash chromatography to give 2c (5.52 g, max. 2.7 mmol) as light yellow foam with 90% purity. MS: m/z=924.54=[M+2H]$^{2+}$, (calculated 924.53).

2c (5.52 g, max. 2.7 mmol) was dissolved in TFA (20 mL). After stirring for 15 min the product was precipitated by adding the reaction mixture dropwise to ice-cold diethyl ether (160 mL). The resulting suspension was centrifuged at 7000×G and 2° C. for 3 min. The supernatant was discarded and the precipitate was dissolved in methanol (10 mL). This solution was added dropwise to ice-cold diethyl ether (160 mL) and the formed suspension was centrifuged at 7000×G and 2° C. for 3 min. After discarding the supernatant the precipitation procedure was accomplished two more times like described above. The remaining oily precipitate was dried in vacuo to give 2d (4.96 g, 2.27 mmol (10×TFA salt), 84%) as a light brown, hygroscopic powder. MS: m/z=1046.64=[M+H]$^+$, (calculated 1046.64).

To a solution of 2d (1.53 g, 0.7 mmol) in dry DMF (20 mL) was added a solution of N,N-diemethylglycine (1.16 g, 11.2 mmol), PyBOP (5.83 g, 11.2 mmol) and DIPEA (3.23 g, 4.36 mL, 25 mmol) in DMF (35 mL) and stirred for 1 h. The mixture was then concentrated in vacuo to an approximate volume of 10 mL. To this residue water was added to a total volume of 100 mL and the solution was acidified to pH 1-2 by adding TFA. The turbid mixture was centrifuged at 5000×G and 2° C. for 3 minutes. The oily precipitate was discarded and the supernatant was purified by RP-HPLC to give 2e (1.05 g, 0.37 mmol (10×TFA salt), 53%) as a colorless oil. MS: m/z=864.54=[M+2H]$^{2+}$, (calculated 864.54).

Example 3

Synthesis of Linker Reagent 3g

Linker reagent 3g was synthesized according to the following scheme:

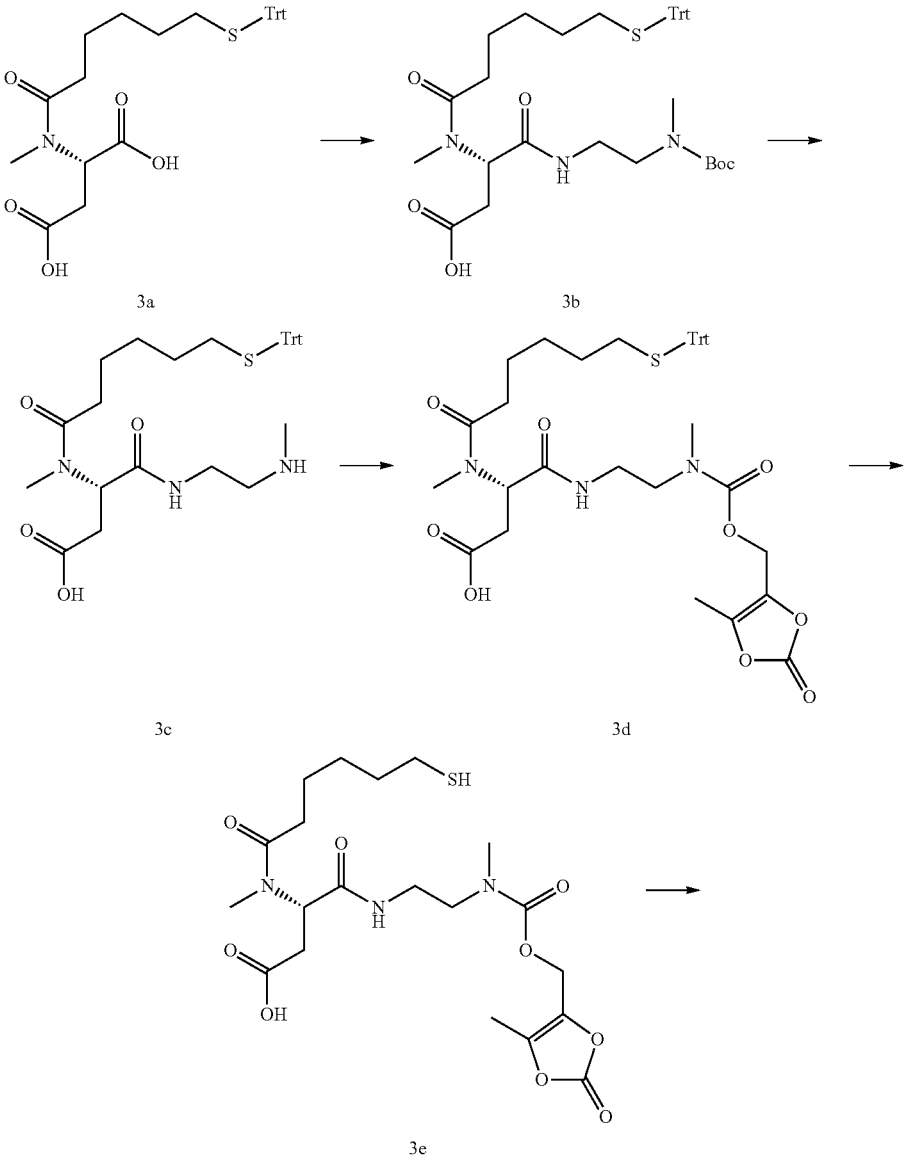

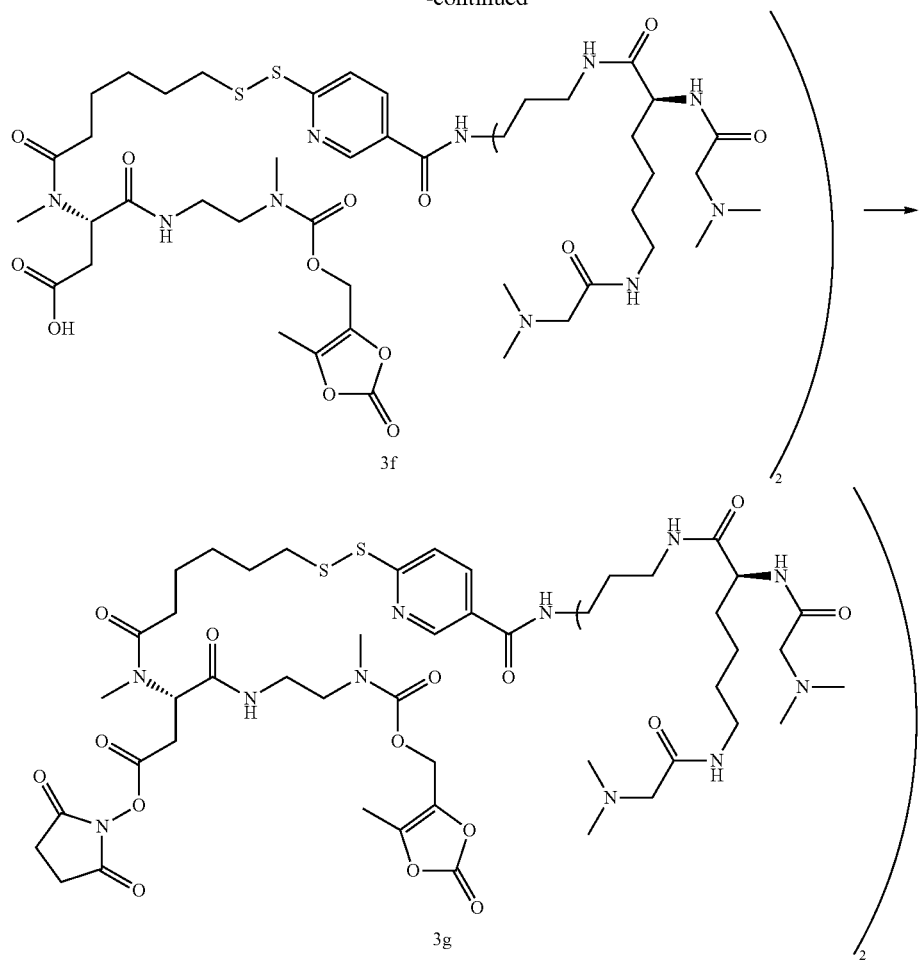

3f

3g

2-Chlorotritylchloride resin (1.4 mmol/g, 1.43 g, 2 mmol) was weighted into a 20 ml syringe with frit. The resin was swollen twice with 10 mL DCM. N-Fmoc-N-methyl-L-Asp (OtBu)-OH (1.06 g, 2.5 mmol) was dissolved in DCM (6 mL) and drawn into the syringe. DIPEA (436 µL, 2.5 mmol) was dissolved in DCM (1 mL) and drawn into the syringe. The syringe was agitated for 5 min. DIPEA (654 µL, 3.75 mmol) was dissolved in DCM (1 mL) and drawn into the syringe. The syringe was agitated for 1 h. MeOH (2 mL) was drawn into the syringe and the syringe agitated for 30 min. The resin was washed 5 times with DMF (10 mL). The resin was agitated 3 times for 5 min with DMF:DBU:piperidine (96:2:2 v/v/v 7 mL). The resin was washed 5 times with DMF (5 mL). 6-Tritylmercaptohexanoic acid (1.95 g, 5 mmol) and PyBOP (2.6 g, 5 mmol) were dissolved in DMF (6 mL) and DIPEA (3.5 mL, 20 mmol) added. After 1 min preincubation the solution was drawn into the syringe and the syringe agitated for 3 h. The resin was washed 5 times with DMF (7 mL), 5 times with DCM (7 mL). A solution of HFIP/DCM (1/4 v/v, 8 mL each) were drawn into the syringe and the syringe agitated 3 times for 30 min. The collected filtrates were concentrated in vacuo. Crude 3a (0.84 g, 1.45 mmol, 73%) was used without further purification in the next step. MS: m/z 598.18=[M+Na]+, (calculated=598.26).

3a (1.67 g, 2.9 mmol) was dissolved in DCM (20 mL) and N-Boc-N-methylethylenediamine (0.62 mL, 3.48 mmol) and PyBOP (1.81 g, 3.48 mmol) were added. DIPEA (2.02 mL, 11.6 mmol) was added and the reaction stirred for 1 h. AcOH (2 mL) was added, the mixture diluted with DCM (40 mL) and washed with water (2×20 mL). The organic layer was dried over $MgSO_4$ and concentrated in vacuo and the crude residue was purified by flash chromatography to give 3b (1.74 g, 2.38 mmol, 82%). MS: m/z=754.19=[M+Na]+, (calculated 754.39).

3b (1.74 g, 2.38 mmol) and triphenylmethanol (0.62 g, 2.38 mmol) were dissolved in DCM (7.2 mL) and TFA (7.2 mL) was added with stirring. The reaction was stirred for 90 min and the solvents were removed in a stream of nitrogen over 45 min. The residue was co-evaporated with DCM. The residue was suspended in ACN/water/TFA (2:1:0.003 v/v/v, 14 mL) and filtered. The filtrate was purified by RP-HPLC to give 3c (0.9 g, 1.3 mmol TFA salt, 55%). MS: m/z 576.20=[M+H]+, (calculated=576.29).

3c (0.9 g, 1.3 mmol) was dissolved in DCM (20 mL) and (5-methyl-2-oxo-1,3-dioxol-4-yl)-methyl 4-nitrophenyl carbonate (0.46 g, 1.56 mmol) was added. DIPEA (0.45 mL, 2.6 mmol) was slowly added and the reaction stirred for 30 min. DIPEA (0.11 mL, 0.65 mmol) was added and the reaction stirred for 30 min. Again, DIPEA (0.11 mL, 0.65 mmol) was added and the reaction stirred for 60 min. AcOH (0.68 mL) was added and the mixture concentrated in vacuo and the crude residue was purified by flash chromatography to give 3d (1.04 g, max. 1.3 mmol). MS: m/z=754.28=[M+Na]+, (calculated 754.28).

3d (1.04 g, max. 1.3 mmol) was dissolved in HFIP/TES/ water (39:1:1 v/v/v, 8.2 mL) and TFA (0.66 mL) was added. After stirring for 15 min the reaction was concentrated in vacuo, the residue suspended in ACN/water/TFA (1:1:0.002 v/v/v 12 mL) and filtered. The filtrate was purified by RP-HPLC to give 3e (0.32 g, 0.65 mmol, 50%). MS: m/z 490.19=[M+H]$^+$, (calculated=490.19).

3e (0.18 g, 0.37 mmol) was dissolved in ACN/water/TFA (1:1:0.002 v/v/v, 3 mL). 2e (1.05 g, 0.37 mmol (10×TFA salt) was dissolved in ACN/water (1:1 v/v, 20 mL). Both solutions were combined and pH 7.4 sodium phosphate (0.5 M, 4 mL) was added and the mixture stirred for 30 min. The pH of the solution was adjusted to ca. pH 2 by addition of ACN/water/TFA (1:1:0.22 v/v/v) and ACN was removed in vacuo. The residue was purified by RP-HPLC to give 3f (0.47 g, 0.24 mmol 5×TFA salt, 65%). MS: m/z 676.86=[M+2H]$^{2+}$, (calculated=676.86).

3f (0.18 g, 94 µmol) was dissolved in ACN (6 mL) and NHS (92 mg, 0.8 mmol) and DCC (166 mg, 0.8 mmol) were added and the reaction stirred for 1h. The solvent was removed in vacuo and the residue suspended in ACN/water/TFA (0.15:0.85:0.001 v/v/v, 6 mL) and filtered. The filtrate was purified by RP-HPLC to give 3g (129 mg, 64 µmol 5×TFA salt, 68%). MS: m/z 725.37=[M+H]$^+$, (calculated=725.37).

Example 4

Synthesis and Purification of Transient Tagged Lucentis-Linker-Monoconjugate 4b 120 mg Lucentis (depicted in the scheme below as Lucentis-NH$_2$) (3 mL of 40 mg/mL Lucentis in 10 mM histidine, 10 wt % α,α-trehalose, 0.01% Tween20, pH 5.5) was buffer exchanged to 60 mM sodium phosphate, 100 mM sodium chloride, pH 7.4 and the concentration of Lucentis was adjusted to 19 mg/mL. Linker reagent 1k was dissolved in DMSO to yield a concentration of 50 mM. 4 molar equivalents of linker reagent 1k relative to the amount of Lucentis were added to the Lucentis solution in 1 molar equivalent steps. The reaction mixture was mixed carefully after each linker reagent addition and incubated for 5 min at room temperature yielding a mixture of unmodified Lucentis, the protected, tagged Lucentis-linker monoconjugate 4a as well as protected, tagged Lucentis-linker bisconjugate.

The mixture of unmodified Lucentis, protected, tagged Lucentis-linker monoconjugate 4a and protected, tagged Lucentis-linker bisconjugate was buffer exchanged to 20 mM boric acid, pH 9.0 and incubated for 2 h at room temperature to remove the (5-methyl-2-oxo-1,3-dioxol-yl)-methyl oxocarbonyl protecting group of 4a yielding the tagged Lucentis-linker monoconjugate 4b.

4b was purified from the reaction mixture by cationic ion exchange chromatography using an Aekta Purifier system equipped with a Source 15S 4.6/100 column. After loading of the reaction mixture (5-fold prediluted in mobile phase A) the following gradient of mobile phase A (20 mM MES, pH 5.7) and mobile phase B (20 mM MES, 500 mM NaCl, pH 5.7) was applied: linear increase from 3.2% B to 50% B in 20 column volumes leading to a separation of 4b from Lucentis and tagged Lucentis-linker bisconjugate (FIG. 1).

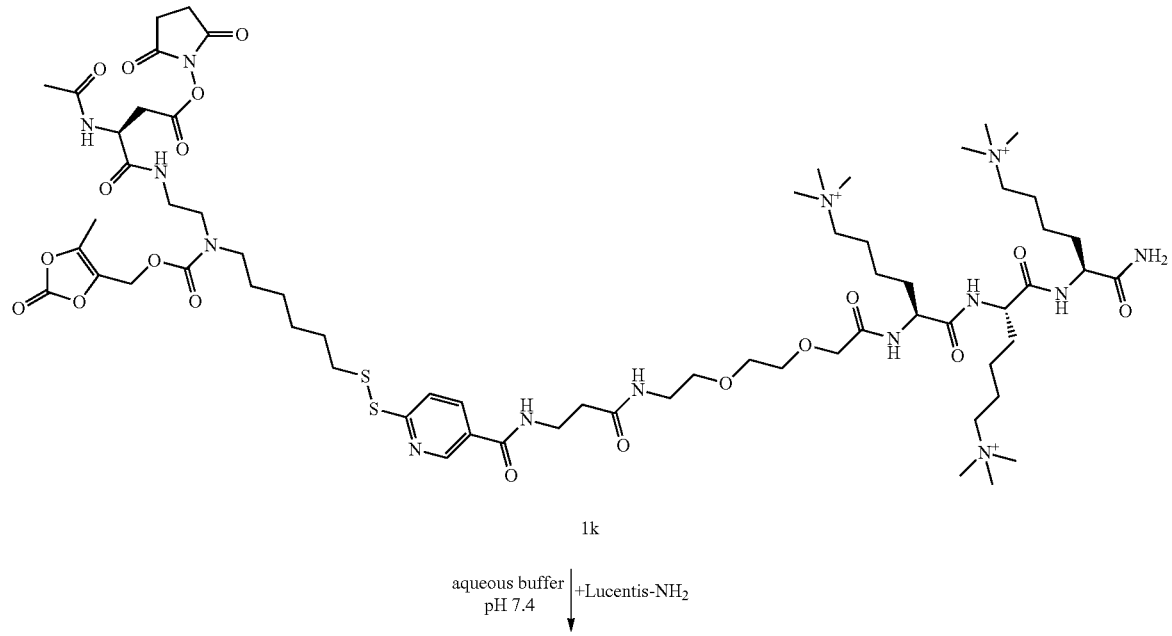

1k aqueous buffer pH 7.4 | +Lucentis-NH$_2$

-continued
4a
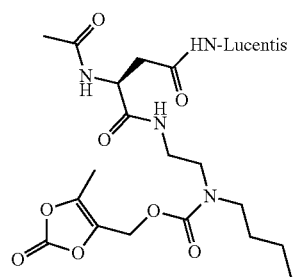 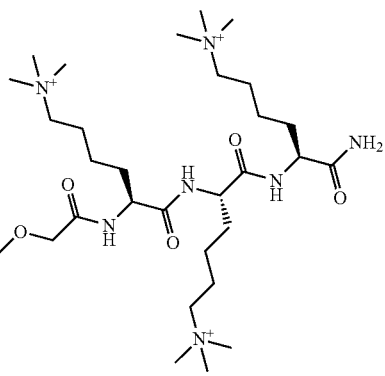
4a
aqueous buffer
pH 9.0
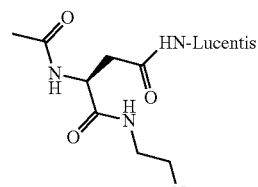 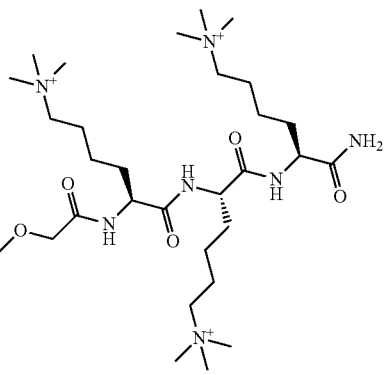
4b

Example 5

Deprotection of Transient Tagged Lucentis-Linker-Monoconjugate 4b Yielding Lucentis-Linker Monoconjugate 5a Purified transient tagged Lucentis-linker-monoconjugate 4b was buffer exchanged to 15 mM succinic acid, 100 mM sodium chloride, 5 mM $Na_2EDTA$, pH 4.0 and the protein concentration was adjusted to 1 mg/mL. The protein solution was cooled to 4° C. and 2 molar equivalents of 25 mM DTT in 15 mM succinic acid, 100 mM sodium chloride, 5 mM $Na_2EDTA$, pH 4.0 were added and incubated overnight at 4° C. yielding the Lucentis-linker monoconjugate 5a.

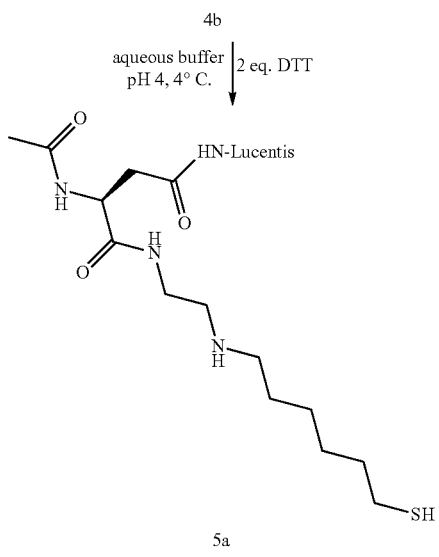

Example 6

Synthesis and Purification of Transient Tagged Lucentis-Linker Monoconjugate 6b 400 mg Lucentis (depicted in the scheme below as Lucentis-$NH_2$) (10 mL of 40 mg/mL Lucentis in 10 mM histidine, 10 wt % α,α-trehalose, 0.01% Tween20, pH 5.5) was buffer buffer exchanged to 60 mM sodium phosphate, 100 mM sodium chloride, pH 7.4 and the concentration of Lucentis was adjusted to 20.8 mg/mL. Linker reagent 3g was dissolved in DMSO to yield a concentration of 100 mM. 4.5 molar equivalents of linker reagent 3g relative to the amount of Lucentis were added to the Lucentis solution. The reaction mixture was mixed carefully and incubated for 5 min at room temperature yielding a mixture of unmodified Lucentis, the protected, tagged Lucentis-linker monoconjugate 6a and protected, tagged Lucentis-linker bisconjugate.

The mixture of Lucentis, protected, tagged Lucentis-linker monoconjugate 6a and protected, tagged Lucentis-linker bisconjugate was buffer exchanged to 60 mM sodium phosphate, 100 mM sodium chloride, pH 6.5. To remove the (5-methyl-2-oxo-1,3-dioxol-yl)-methyl oxocarbonyl protecting group of 6a 0.5 M $NH_2OH$ (dissolved in 10 mM sodium citrate, 140 mM sodium chloride, 5 mM $Na_2EDTA$, pH 6.5) was added to a final concentration of 45 mM and the deprotection reaction was incubated at room temperature for 2.5 h yielding the tagged Lucentis-linker monoconjugate 6b.

6b was purified from the reaction mixture by cationic ion exchange chromatography using an Aekta Purifier system equipped with a Source 15S 6 mL column (FIG. 2). After loading of the reaction mixture (5-fold prediluted in mobile phase A) the following gradient of mobile phase A (20 mM MES, pH 5.7) and mobile phase B (20 mM MES, 500 mM NaCl, pH 5.7) was applied: linear increase from 0% B to 50% B in 20 column volumes leading to a separation of 6b from Lucentis and tagged Lucentis-linker bisconjugate.

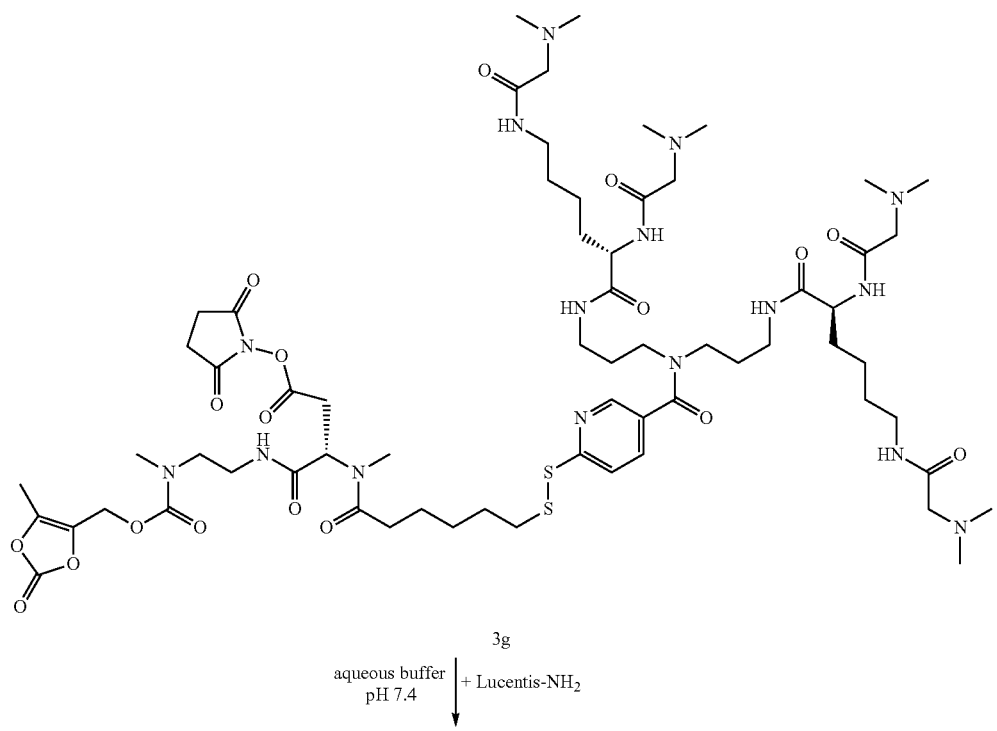

-continued
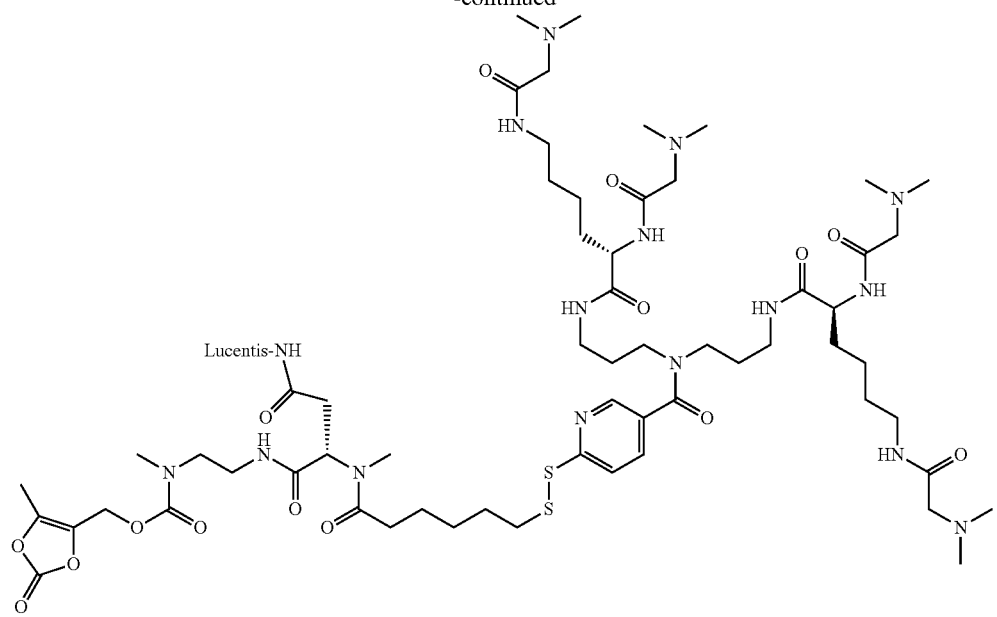
6a
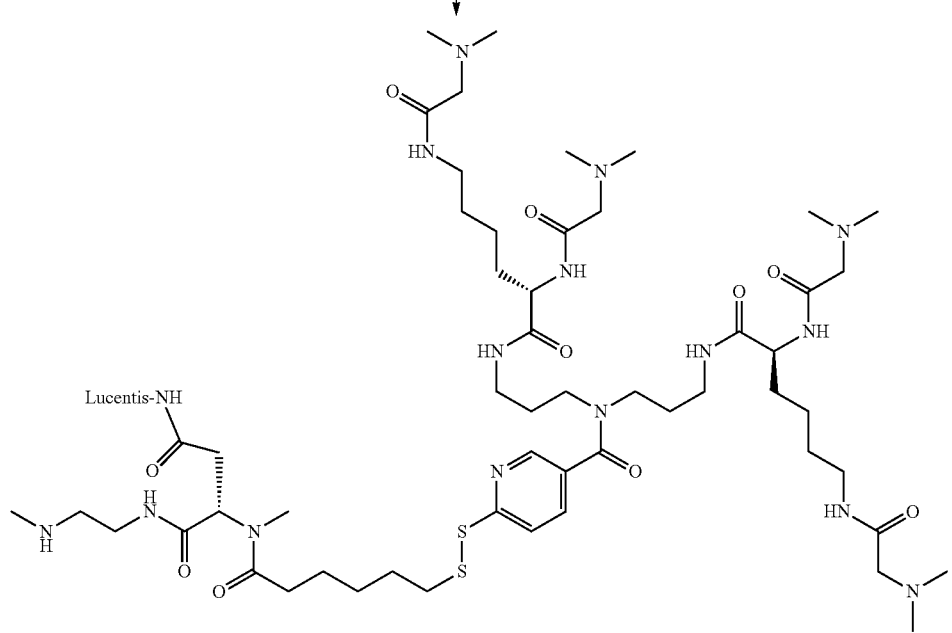
6b

Example 7

Deprotection of Transient Tagged Lucentis-Linker-Monoconjugate 6b Yielding Lucentis-Linker Monoconjugate 7a Purified transient tagged Lucentis-linker-monoconjugate 6b was buffer exchanged to 15 mM succinic acid, 100 mM sodium chloride, 5 mM $Na_2EDTA$, pH 4.0 and the protein concentration was adjusted to 10 mg/mL. The protein solution was cooled to 4° C. and 5 molar equivalents of 25 mM DTT in 15 mM succinic acid, 100 mM sodium chloride, 5 mM $Na_2EDTA$, pH 4.0 were added and incubated overnight at 4° C. yielding the Lucentis-linker monoconjugate 7a.

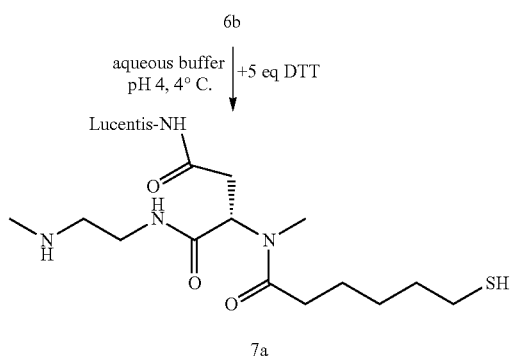

Abbreviations

ACN acetonitrile
AcOH acetic acid
Ado 8-amino-3,6-dioxaoctanoic acid
aq. aqueous
Asp aspartate
β-Ala beta-alanine
Boc tert-butyloxycarbonyl
CIEC cationic ion exchange chromatography
cv column volume
DBU 1,8-diazabicyclo (5.4.0)undec-7-ene
DCC dicyclohexylcarbodiimide
DCM dichloromethane
DIPEA diisopropylethylamine
DMF dimethylformamide
DTT dithiothreitol
EDTA ethylendiaminetetraacetic acid
Fmoc fluorenylmethyloxycarbonyl
HATU 1-[Bis(dimethylamino)methylene]-1H-1,2,3-triazolo[4,5-b]pyridinium 3-oxid hexafluorophosphate
HFIP hexafluoroisopropanol
HOAt 1-hydroxy-7-azabenzotriazole
HOBt 1-hydroxybenzotriazole
HPLC high performance liquid chromatography
Lys lysine
max. maximal
Me methyl
MeOH methanol
MES 2-(N-morpholino)ethanesulfonic acid
MS mass spectrometry
NHS N-hydroxysuccinimide
PyBOP benzotriazol-1-yl-oxytripyrrolidinophosphonium hexafluorophosphate
RP-HPLC reversed phase-high performance liquid chromatography
sat. saturated
Su N-hydroxysuccinimidyl
tBu and t-Bu tert.-butyl
TES triethylsilane
TFA trifluoroacetic acid
THF tetrahydrofurane
TLC thin layer chromatography
Trt trityl
TBTU N,N,N'N'-tetramethyl-O-(benzotriazol-1-yl)uronium tetrafluoroborate

The invention claimed is:

1. A compound having a moiety of formula (I):

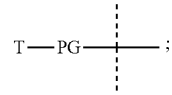

wherein:
  the dashed line indicates attachment to the rest of the compound;
  T is a tag moiety; and
  PG is a protecting group moiety that is utilized for the reversible protection of a thiol functional group;
wherein T is a moiety of formula (a):

(a)

wherein:
  the dashed line indicates attachment to the rest of the compound;
  $R^1$, $R^{1a}$, $R^{1b}$, $R^2$, $R^{2a}$, $R^{2b}$, $R^3$, $R^{3a}$, $R^{3b}$, $R^4$, $R^{4a}$, and $R^{4b}$ are independently of each other H or methyl;
  each m is independently of each other 1-8;
  each n is independently of each other 1-8;
  each x is independently of each other 1-8;
  each y is independently of each other 0-8; and
  SP is a spacer moiety selected from the group consisting of:
    wherein spacer moiety SP is a chemical bond, $C_{1-50}$ alkyl, $C_{2-50}$ alkenyl, or $C_{2-50}$ alkynyl, which $C_{1-50}$ alkyl, $C_{2-50}$ alkenyl or $C_{2-50}$ alkynyl is optionally interrupted by one or more groups selected from Q, —C(O)O—, —O—, —C(O)—, —C(O)N($R^{11}$)—, —S(O)$_2$N ($R^{11}$)—, —S(O)N($R^{11}$)—, —S(O)$_2$—, —S(O)—, —N($R^{11}$)S(O)$_2$N($R^{11a}$)—, —S—, —N($R^{11}$)—, —OC(O)$R^{11}$, —N($R^{11}$)C(O)—, —N($R^{11}$)S(O)—, —N($R^{11}$)S(O)—, —N($R^{11}$)C(O)O—, —N($R^{11}$)C(O)N($R^{11a}$)—, and —OC(O)N($R^{11}R^{11a}$)—, wherein:

Q is selected from the group consisting of phenyl, naphthyl, indenyl, indanyl, tetralinyl, $C_{3-10}$ cycloalkyl, 4- to 7-membered heterocyclyl, and 8- to 11-membered heterobicyclyl, wherein Q is optionally substituted with one or more $R^{10}$, which are the same or different; and $R^{10}$, $R^{11}$, and $R^{11a}$ are independently selected from the group consisting of H and $C_{1-6}$ alkyl, wherein $C_{1-6}$ alkyl is optionally substituted with one or more halogen, which are the same or different;

wherein, when the spacer moiety SP is $C_{1-50}$ alkyl, $C_{2-50}$ alkenyl, or $C_{2-50}$ alkynyl, the spacer moiety SP is optionally substituted by one or more substituents selected from the group consisting of halogen, —CN, —COO$R^9$, —O$R^9$, —C(O)$R^9$, —C(O)N($R^9R^{9a}$), —S(O)$_2$N($R^9R^{9a}$), —S(O)N($R^9R^{9a}$), —S(O)$_2R^9$, —S(O)$R^9$, —N($R^9$)S(O)$_2$N($R^{9a}R^{9b}$), —S$R^9$, —N($R^9R^{9a}$), —NO$_2$, —OC(O)$R^9$, —N($R^9$)C(O)$R^{9a}$, —N($R^9$)S(O)$_2R^{9a}$, —N($R^9$)S(O)$R^{9a}$, —N($R^9$)C(O)O$R^{9a}$, —N($R^9$)C(O)N($R^{9a}R^{9b}$), —OC(O)N($R^9R^{9a}$), Q, $C_{1-50}$ alkyl, $C_{2-50}$ alkenyl, and $C_{2-50}$ alkynyl, wherein Q, $C_{1-50}$ alkyl, $C_{2-50}$ alkenyl, $C_{2-50}$ alkynyl are optionally substituted with one or more $R^{10}$, which are the same or different, and wherein $C_{1-50}$ alkyl, $C_{2-50}$ alkenyl, and $C_{2-50}$ alkynyl are optionally interrupted by one or more group(s) selected from the group consisting of Q, —C(O)O—, —O—, —C(O)—, —C(O)N($R^{11}$)—, —S(O)$_2$N($R^{11}$)—, —S(O)N($R^{11}$)—, —S(O)$_2$—, —S(O)—, —N($R^{11}$)S(O)$_2$N($R^{11a}$)—, —S—, —N($R^{11}$)—, —OC(O)$R^{11}$, —N($R^{11}$)C(O)—, —N($R^{11}$)S(O)$_2$—, —N($R^{11}$)S(O)—, —N($R^{11}$)C(O)O—, —N($R^{11}$)C(O)N($R^{11a}$)—, and —OC(O)N($R^{11}R^{11a}$), wherein:

$R^9$, $R^{9a}$, and $R^{9b}$ are independently selected from the group consisting of H, Q, $C_{1-50}$ alkyl, $C_{2-50}$ alkenyl, and $C_{2-50}$ alkynyl, wherein Q, $C_{1-50}$ alkyl, $C_{2-50}$ alkenyl, and $C_{2-50}$ alkynyl are optionally substituted with one or more $R^{10}$, which are the same or different, and wherein $C_{1-50}$ alkyl, $C_{2-50}$ alkenyl, and $C_{2-50}$ alkynyl are optionally interrupted by one or more group(s) selected from the group consisting of Q, —C(O)O—, —O—, —C(O)—, —C(O)N($R^{11}$)—, —S(O)$_2$N($R^{11}$)—, —S(O)N($R^{11}$)—, —S(O)$_2$—, —S(O)—, —N($R^{11}$)S(O)$_2$N($R^{11a}$)—, —S—, —N($R^{11}$)—, —OC(O)$R^{11}$, —N($R^{11}$)C(O)—, —N($R^{11}$)S(O)$_2$—, —N($R^{11}$)S(O)—, —N($R^{11}$)C(O)O—, —N($R^{11}$)C(O)N($R^{11a}$)—, and —OC(O)N($R^{11}R^{11a}$);

Q is as defined above;

$R^{10}$ is halogen, —CN, oxo (=O), —COO$R^{12}$, —O$R^{12}$, —C(O)$R^{12}$, —C(O)N($R^{12}R^{12a}$), —S(O)$_2$N($R^{12}R^{12a}$), —S(O)N($R^{12}R^{12a}$), —S(O)$_2R^{12}$, —S(O)$R^{12}$, —N($R^{12}$)S(O)$_2$N($R^{12a}R^{12b}$), —S$R^{12}$, —N($R^{12}R^{12a}$), —NO$_2$, —OC(O)$R^{12}$, —N($R^{12}$)C(O)$R^{12a}$, —N($R^{12}$)S(O)$_2R^{12a}$, —N($R^{12}$)S(O)$R^{12a}$, —N($R^{12}$)C(O)O$R^{12a}$, —N($R^{12}$)C(O)N($R^{12a}R^{12b}$), —OC(O)N($R^{12}R^{12a}$), or $C_{1-6}$ alkyl, wherein $C_{1-6}$ alkyl is optionally substituted with one or more halogen, which are the same or different, and $R^{11}$, $R^{11a}$, $R^{12}$, $R^{12a}$, and $R^{12b}$ are independently selected from the group consisting of H and $C_{1-6}$ alkyl, wherein $C_{1-6}$ alkyl is optionally substituted with one or more halogen, which are the same or different; and wherein PG is selected from the group consisting of:

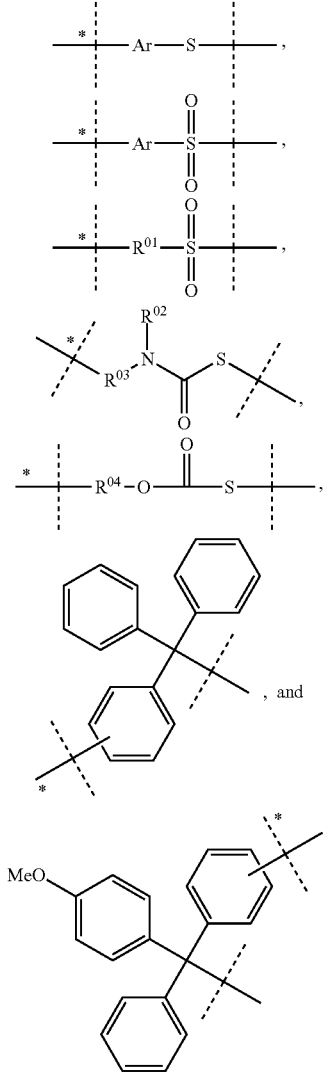

wherein:
the dashed line marked with an asterisk indicates attachment to T and the unmarked dashed line indicates attachment to the rest of the compound;

Ar is an aromatic moiety which is optionally further substituted;

$R^{01}$, $R^{03}$, and $R^{04}$ are independently of each other a chemical bond or is $C_{1-50}$ alkyl, $C_{2-50}$ alkenyl, or $C_{2-50}$ alkynyl, wherein:
$C_{1-50}$ alkyl, $C_{2-50}$ alkenyl, and $C_{2-50}$ alkynyl are optionally substituted with one or more $R^3$, which are the same or different; and C<sub>1-50</sub> alkyl, C<sub>1-50</sub> alkenyl, and C<sub>1-50</sub> alkynyl are optionally interrupted by one or more groups selected from the group consisting of -Q-, —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O)$R^4$, —N($R^4$)C(O)—, —N($R^4$)S(O)$_2$—, —N($R^4$)S(O)—, —N($R^4$)C(O)O—, —N($R^4$)C(O)N($R^{4a}$)—, and —OC(O)N($R^4R^{4a}$);

$R^{02}$ is —H, $C_{1-50}$alkyl, $C_{2-5}$ alkenyl, or $C_{2-50}$ alkynyl, wherein:

$C_{1-50}$ alkyl, $C_{2-50}$ alkenyl, and $C_{2-50}$ alkynyl are optionally substituted with one or more $R^3$, which are the same or different; and $C_{1-50}$ alkyl, $C_{2-50}$ alkenyl, and $C_{2-50}$ alkynyl are optionally interrupted by one or more groups selected from the group consisting of -Q-, —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O)$R^4$, —N($R^4$)C(O)—, —N($R^4$)S(O)$_2$—, —N($R^4$)S(O)—, —N($R^4$)C(O)O—, —N($R^4$)C(O)N($R^{4a}$)—, and —OC(O)N($R^4R^{4a}$);

Q is selected from the group consisting of phenyl, naphthyl, indenyl, indanyl, tetralinyl, $C_{3-10}$ cycloalkyl, 4-membered to 7-membered heterocyclyl, and 8 membered to 11-membered heterobicyclyl, wherein T is optionally substituted with one or more $R^3$, which are the same or different;

$R^3$ is halogen, —CN, oxo (═O), —COO$R^5$, —O$R^5$, —C(O)$R^5$, —C(O)N($R^5R^{5a}$), —S(O)$_2$N($R^5R^{5a}$), —S(O)N($R^5R^{5a}$), —S(O)$_2R^5$, —S(O)$R^5$, —N($R^5$)S(O)$_2$N($R^{5a}R^{5b}$), —S$R^5$, —N($R^5R^{5a}$), —NO$_2$, —OC(O)$R^5$, —N($R^5$)C(O)$R^{5a}$, —N($R^5$)S(O)$_2R^{5a}$, —N($R^5$)S(O)$R^{5a}$, —N($R^5$)C(O)O$R^{5a}$, —N($R^5$)C(O)N($R^{5a}R^{5b}$), —OC(O)N($R^5R^{5a}$), or $C_{1-6}$ alkyl, wherein:

$C_{1-6}$ alkyl is optionally substituted with one or more halogen, which are the same or different; and $R^4$, $R^{4a}$, $R^5$, $R^{5a}$, and $R^{5b}$ are independently selected from the group consisting of —H or $C_{1-6}$ alkyl, wherein:

$C_{1-6}$ alkyl is optionally substituted with one or more halogen, which are the same or different.

2. The compound of claim 1;
wherein Ar is selected from the group consisting of:

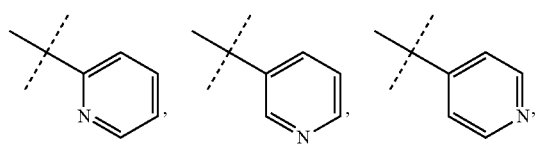

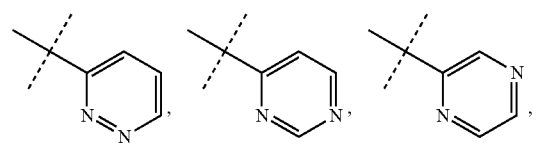

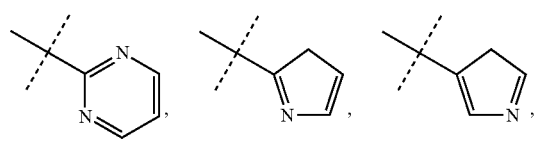

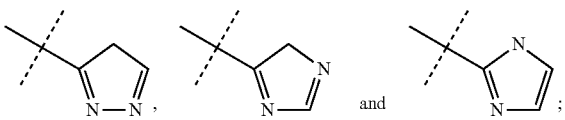

wherein:
dashed lines marked with an asterisk indicate attachment to T of formula (I) and the unmarked dashed lines indicate attachment to the rest of PG;
W is independently of each other O, S, or N; and
W' is N; and
wherein Ar is optionally substituted with one or more substituent(s) independently selected from the group consisting of NO$_2$, Cl, and F.

3. The compound of claim 1;
wherein PG is:

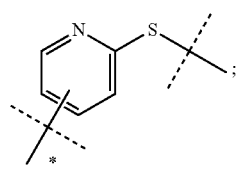

wherein:
the dashed line marked with an asterisk indicates attachment to T; and
the unmarked dashed line indicates attachment to the rest of the compound.

4. The compound of claim 1;
wherein T is a moiety of formula (b):

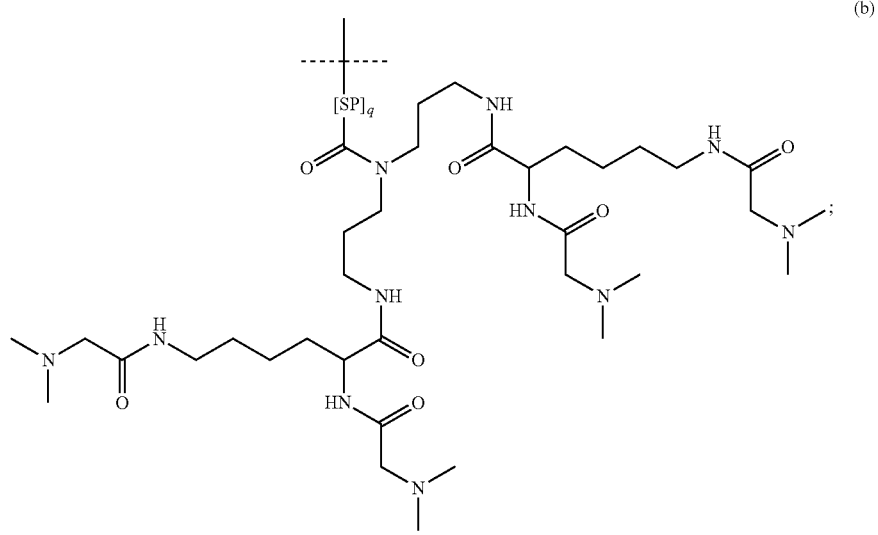

wherein:
the dashed line indicates attachment to PG of formula (I);
q is 0 or 1; and
SP is a spacer moiety.

5. The compound of claim 1, further having:
a moiety —$L^2$—$L^1$—;
wherein $L^2$ and $L^1$ are attached to formula (I) as shown in formula (IIa):

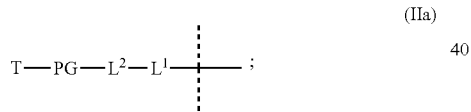

wherein:
the dashed line indicates attachment to the rest of the compound;
T and PG are as defined in claim 1;
$L^2$ is a chemical bond or a spacer moiety; and
$L^1$ is a reversible prodrug linker moiety;
wherein the spacer moiety for $L^2$ is selected from the group consisting of —T—, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl, wherein:
—T—, $C_{1-20}$ alkyl, $C_{2-20}$ alkenyl, and $C_{2-20}$ alkynyl are optionally substituted with one or more $R^{y2}$, which are the same or different; and
$C_{1-20}$ alkyl, $C_{2-20}$ alkenyl, and $C_{2-20}$ alkynyl are optionally interrupted by one or more groups selected from the group consisting of —T—, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

wherein:
$R^{y1}$ and $R^{y1a}$ are independently of each other selected from the group consisting of —H, —T, $C_{1-10}$ alkyl, $C_{2-10}$ alkenyl, and $C_{2-10}$ alkynyl, wherein
—T, $C_{1-10}$ alkyl, $C_{2-10}$ alkenyl, and $C_{2-10}$ alkynyl are optionally substituted with one or more $R^{y2}$, which are the same or different; and
$C_{1-10}$ alkyl, $C_{2-10}$ alkenyl, and $C_{2-10}$ alkynyl are optionally interrupted by one or more groups selected from the group consisting of —T—, —C(O)O—, —O—, —C(O)—, —C(O)N($R^{y4}$)—, —S(O)$_2$N($R^{y4}$)—, —S(O)N($R^{4y}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;
each T is independently selected from the group consisting of phenyl, naphthyl, indenyl, indanyl, tetralinyl, $C_{3-10}$ cycloalkyl, 3-membered to 10-membered heterocyclyl, 8-membered to 11-membered heterobicyclyl, 8-membered to 30-membered carbopolycyclyl, and 8-membered to 30-membered heteropolycyclyl, wherein:
each T is independently optionally substituted with one or more $R^{y2}$, which are the same or different;
$R^{y2}$ is selected from the group consisting of halogen, —CN, oxo (=O), —COO$R^{y5}$, —O$R^{y5}$, —C(O)$R^{y5}$, —C(O)N($R^{y5}R^{y5}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl, wherein:
$C_{1-6}$ alkyl is optionally substituted with one or more halogen, which are the same or different; and
each $R^{y3}$, $R^{y3a}$, $R^{y4}$, $R^{y4a}$, $R^{y5}$, $R^{y5a}$, and $R^{y5b}$ is, independently of each other, selected from the group consisting of —H, and $C_{1-6}$ alkyl; wherein:
$C_{1-6}$ alkyl is optionally substituted with one or more halogen, which are the same or different; and wherein the reversible prodrug linker moiety $L^1$ is a moiety of formula (b-iii):

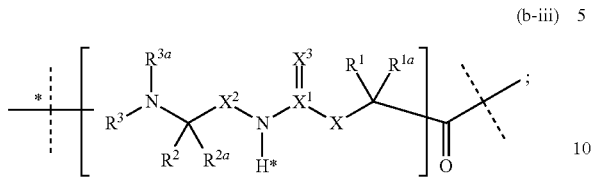

wherein:

the dashed line with marked with the asterisk indicates attachment to $L^2$ of formula (IIa);

the unmarked dashed line corresponds to the dashed line in formula (IIa); and the moiety of formula (b-iii) is attached to the rest of the compound through an amine functional;

wherein:
X of formula (b-iii) is $C(R^4R^{4a})$, $N(R^4)$, O, $C(R^4R^{4a})$—$C(R^5R^{5a})$, $C(R^5R^{5a})$—$C(R^4R^{4a})$, $C(R^4R^{4a})$—$N(R^6)$, $N(R^6)$—$C(R^4R^{4a})$, $C(R^4R^{4a})$—O, or O—$C(R^4R^{4a})$;

$X^1$ of formula (b-iii) is C or S(O);

$X^2$ of formula (b-iii) is $C(R^7, R^{7a})$ or $C(R^7, R^{7a})$—$C(R^8, R^{8a})$;

$X^3$ of formula (b-iii) is O, S, or N—CN;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, and $R^{8a}$ of formula (b-iii) are independent of each other selected from the group consisting of H and $C_{1-4}$ alkyl;

optionally, one or more of the pairs $R^{1a}/R^{4a}$, $R^{1a}/R^{5a}$, $R^{4a}/R^{5a}$, and $R^{7a}/R^{8a}$ of formula (b-iii) form a chemical bond;

optionally, one or more of the pairs $R^1/R^{1a}$, $R^2/R^{2a}$, $R^4/R^{4a}$, $R^5/R^{5a}$, $R^7/R^{7a}$, and $R^8/R^{8a}$ of formula (b-iii) are joined together with the atom to which they are attached to form a $C_{3-10}$ cycloalkyl or a 4- to 7-membered heterocyclyl;

optionally, one or more of the pairs $R^1/R^4$, $R^1/R^5$, $R^1/R^6$, $R^4/R^5$, $R^4/R^6$, $R^7/R^8$, and $R^2/R^3$ of formula (b-iii) are joined together with the atoms to which they are attached to form a ring A;

optionally, $R^3/R^{3a}$ of formula (b-iii) are joined together with the nitrogen atom to which they are attached to form a 4- to 7-membered heterocycle;

A of formula (b-iii) is selected from the group consisting of phenyl, naphthyl, indenyl, indanyl, tetralinyl, $C_{3-10}$ cycloalkyl, 4- to 7-membered heterocyclyl, and 8- to 11-membered heterobicyclyl; and wherein the moiety of formula (b-iii) is:
substituted with $L^2$ of formula (IIa); and
optionally further substituted;
provided that:
the hydrogen marked with the asterisk in formula (b-iii) is not replaced; and
$R^3$ and $R^{3a}$ of formula (b-iii) are, independently of each other, H or are connected to N through an $SP^3$-hybridized carbon atom.

6. The compound of claim 5;
wherein $L^2$ is the spacer moiety.

7. The compound of claim 5;
wherein the compound is of formula (IIIa):

$(T-PG-L^2-L^1)_x$-PM     (IIIa);

wherein:
x is 1-20; and
PM is a protein having a molecular weight of 1 kDa to 1000 kDa.

8. The compound of claim 7;
wherein PM comprises and antibody or antibody fragment.

9. A method of purification, comprising the steps of:
(i) providing a mixture comprising a multitude of conjugates selected from the group consisting of formula (II) and formula (IIIa) which differ by their value for x, where the formulas (III) and (IIIa) are:

$(T-PG-X^1-L-X^2)_x$-PM     (III); and

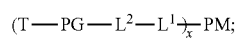     (IIIa)

wherein:

each T is, independently of each other, a charged tag moiety; and each PG is, independently of each other, a protecting group moiety that is utilized for the reversible protection of a thiol functional group;

$X^1$ and $X^2$ are each, independently of each other, a linkage;

L and $L^2$ are each, independently of each other, a chemical bond or a spacer moiety;

$L^1$ is a reversible prodrug linker moiety;

each x is, independently of each other, an integer from 1-20; and each PM is, independently from each other, a protein having a molecular weight of 1 kDa to 1000 kDa;

wherein T is a moiety of formula (a):

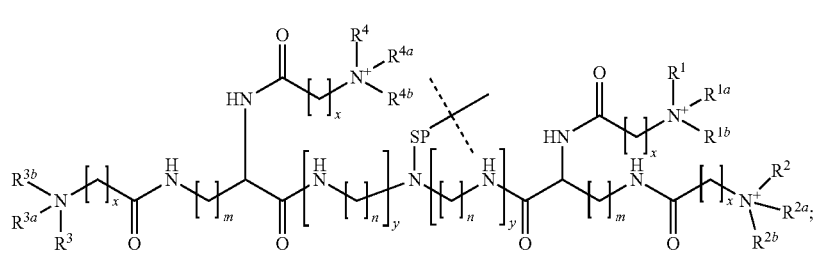

(a)

wherein:

the dashed line indicates attachment to the rest of the compound;

$R^1$, $R^{1a}$, $R^{1b}$, $R^2$, $R^{2a}$, $R^{2b}$, $R^3$, $R^{3a}$, $R^{3b}$, $R^4$, $R^{4a}$, and $R^{4b}$ are independently of each other H or methyl;

each m is independently of each other 1-8;

each n is independently of each other 1-8;

each y is independently of each other 0-8; and

SP is a spacer moiety;

wherein PG is selected from the group consisting of:

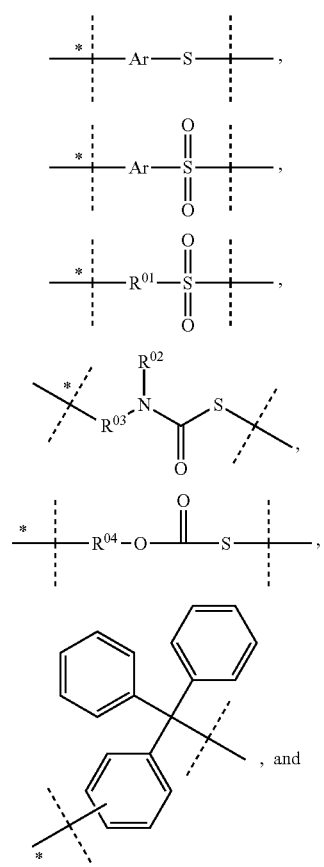

, and

-continued

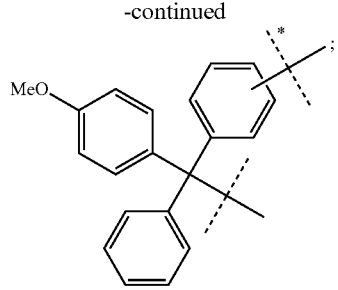

wherein:

the dashed line marked with an asterisk indicates attachment to T and the unmarked dashed line indicates attachment to the rest of the compound;

Ar is an aromatic moiety which is optionally further substituted;

$R^{01}$, $R^{03}$, and $R^{04}$ are independently of each other a chemical bond or is $C_{1-50}$ alkyl, $C_{2-50}$ alkenyl, or $C_{2-50}$ alkynyl, wherein:

$C_{1-50}$ alkyl, $C_{2-50}$ alkenyl, and $C_{2-50}$ alkynyl are optionally substituted with one or more $R^3$, which are the same or different; and $C_{1-50}$ alkyl, $C_{2-50}$ alkenyl, and $C_{2-50}$ alkynyl are optionally interrupted by one or more groups selected from the group consisting of —Q—, —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O)$R^4$, —N($R^4$)C(O)—, —N($R^4$)S(O)$_2$—, —N($R^4$)S(O)—, —N($R^4$)C(O)O—, —N($R^4$)C(O)N($R^{4a}$)—, and —OC(O)N($R^4R^{4a}$);

$R^{02}$ is —H, $C_{1-50}$ alkyl, $C_{2-50}$ alkenyl, or $C_{2-50}$ alkynyl, wherein:

$C_{1-50}$ alkyl, $C_{2-50}$ alkenyl, and $C_{2-50}$ alkynyl are optionally substituted with one or more $R^3$, which are the same or different; and $C_{1-50}$ alkyl, $C_{2-50}$ alkenyl, and $C_{2-50}$ alkynyl are optionally interrupted by one or more groups selected from the group consisting of —Q—, —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N($R^{4a}$)—, —S—, —N($R^4$)—, —OC(O)$R^4$, —N($R^4$)C(O)—, —N($R^4$)(O)$_2$—, —N($R^4$)S(O)—, —N($R^4$)C(O)O—, —N($R^4$)C(O)N($R^{4a}$)—, and —OC(O)N($R^4R^{4a}$);

Q is selected from the group consisting of phenyl, naphthyl, indenyl, indanyl, tetralinyl, $C_{3-10}$ cycloalkyl, 4-membered to 7-membered heterocyclyl, and 8 membered to 11-membered heterobicyclyl, wherein T is optionally substituted with one or more $R^3$, which are the same or different;

$R^3$ is halogen, —CN, oxo (=O), —COOR$^5$, —OR$^5$, —C(O)R$^5$, —C(O)N(R$^5$R$^{5a}$), —S(O)$_2$N(R$^5$R$^{5a}$), —S(O)N(R$^5$R$^{5a}$), —S(O)$_2$R$^5$, —S(O)R$^5$, —N(R$^5$)S(O)$_2$N(R$^{5a}$R$^{5b}$), —SR$^5$, —N(R$^5$R$^{5a}$), —NO$_2$, —OC(O)R$^5$, —N(R$^5$)C(O)R$^{5a}$, —N(R$^5$)S(O)$_2$R$^{5a}$, —N(R$^5$)S(O)R$^{5a}$, —N(R$^5$)C(O)OR$^{5a}$, —N(R$^5$)C(O)N(R$^{5a}$R$^{5b}$), —OC(O)N(R$^5$R$^{5a}$), or $C_{1-6}$ alkyl, wherein:

$C_{1-6}$ alkyl is optionally substituted with one or more halogen, which are the same or different; and $R^4$, $R^{4a}$, $R^5$, $R^{5a}$, and $R^{5b}$ are independently selected from the group consisting of —H or $C_{1-6}$ alkyl, wherein:

$C_{1-6}$ alkyl is optionally substituted with one or more halogen, which are the same or different;

wherein the spacer moiety for $L^2$ is selected from the group consisting of —T—, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, $C_{1-50}$ alkyl, $C_{2-50}$ alkenyl, and $C_{2-50}$ alkynyl, wherein:

—T—, $C_{1-20}$ alkyl, $C_{2-20}$ alkenyl, and $C_{2-20}$ alkynyl are optionally substituted with one or more $R^{y2}$, which are the same or different; and $C_{1-20}$ alkyl, $C_{2-20}$ alkenyl, and $C_{2-20}$ alkynyl are optionally interrupted by one or more groups selected from the group consisting of —T—, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

wherein:

$R^{y1}$ and $R^{y1a}$ are independently of each other selected from the group consisting of —H, —T, $C_{1-10}$ alkyl, $C_{2-10}$ alkenyl, and $C_{2-10}$ alkynyl, wherein —T, $C_{1-10}$ alkyl, $C_{2-10}$ alkenyl, and $C_{2-10}$ alkynyl are optionally substituted with one or more $R^{y2}$, which are the same or different; and $C_{1-10}$ alkyl, $C_{2-10}$ alkenyl, and $C_{2-10}$ alkynyl are optionally interrupted by one or more groups selected from the group consisting of —T—, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, $C_{3-10}$ cycloalkyl, 3-membered to 10-membered heterocyclyl, 8-membered to 11-membered heterobicyclyl, 8-membered to 30-membered carbopolycyclyl, and 8-membered to 30-membered heteropolycyclyl, wherein:

each T is independently optionally substituted with one or more $R^{y2}$, which are the same or different;

$R^{y2}$ is selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)$_2$R$^{y5}$, —N(R$^{y3}$)S(O)$_2$N(R$^{y5}$R$^{y5a}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and $C_{1-6}$ alkyl, wherein:

$C_{1-6}$ alkyl is optionally substituted with one or more halogen, which are the same or different; and each $R^{y3}$, $R^{y3a}$, $R^{y4}$, $R^{y4a}$, $R^{y5}$, $R^{y5a}$, and $R^{y5b}$ is, independently of each other, selected from the group consisting of —H, and $C_{1-6}$ alkyl; wherein:

$C_{1-6}$ alkyl is optionally substituted with one or more halogen, which are the same or different; and wherein the reversible prodrug linker moiety $L^1$ is a moiety of formula (b-iii):

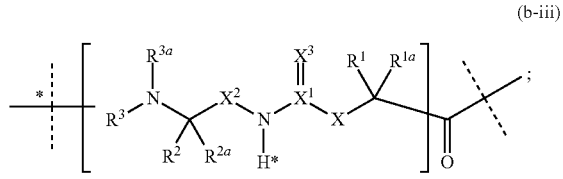

(b-iii)

wherein:
the dashed line with marked with the asterisk indicates attachment to $L^2$;
the unmarked dashed line indicates attachment to PM; and
the moiety of formula (b-iii) is attached to PM through an amine functional group;

wherein:
X of formula (b-iii) is C(R$^4$R$^{4a}$), N(R$^4$), O, C(R$^4$R$^{4a}$)—C(R$^5$R$^{5a}$), C(R$^5$R$^{5a}$)—C(R$^4$R$^{4a}$), C(R$^4$R$^{4a}$)—N(R$^6$), N(R$^6$)—C(R$^4$R$^{4a}$), C(R$^4$R$^{4a}$)—O, or O—C(R$^4$R$^{4a}$);

$X^1$ of formula (b-iii) is C or S(O);
$X^2$ of formula (b-iii) is C(R$^7$, R$^{7a}$) or C(R$^7$, R$^{7a}$)—C(R$^8$, R$^{8a}$);
$X^3$ of formula (b-iii) is O, S, or N—CN;
$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, and $R^{8a}$ of formula (b-iii) are independent of each other selected from the group consisting of H and $C_{1-4}$ alkyl;
optionally, one or more of the pairs $R^{1a}/R^{4a}$, $R^{1a}/R^{5a}$, $R^{4a}/R^{5a}$, and $R^{7a}/R^{8a}$ of formula (b-iii) form a chemical bond;
optionally, one or more of the pairs $R^1/R^{1a}$, $R^2/R^{2a}$, $R^4/R^{4a}$, $R^5/R^{5a}$, $R^7/R^{7a}$, and $R^8/R^{8a}$ of formula (b-iii) are joined together with the atom to which they are attached to form a $C_{3-10}$ cycloalkyl or a 4-membered to 7-membered heterocyclyl;
optionally, one or more of the pairs $R^1/R^4$, $R^1/R^5$, $R^1/R^6$, $R^4/R^5$, $R^4/R^6$, $R^7/R^8$, and $R^2/R^3$ of formula (b-iii) are joined together with the atoms to which they are attached to form a ring A;

optionally, $R^3/R^{3a}$ of formula (b-iii) are joined together with the nitrogen atom to which they are attached to form a 4-membered to 7-membered heterocycle;

A of formula (b-iii) is selected from the group consisting of phenyl, naphthyl, indenyl, indanyl, tetralinyl, $C_{3-10}$ cycloalkyl, 4-membered to 7-membered heterocyclyl, and 8-membered to 11-membered heterobicyclyl; and wherein the moiety of formula (b-iii) is:

substituted with $L^2$ of formula (IIa); and optionally further substituted;

provided that:

the hydrogen marked with the asterisk in formula (b-iii) is not replaced; and $R^3$ and $R^{3a}$ of formula (b-iii) are, independently of each other, H or are connected to N through an $SP^3$-hybridized carbon atom;

(ii) subjecting the mixture of step (i) to ion exchange chromatography; and (iii) isolating a fraction that comprises compounds of formula (III) or (IIIa) in which at least 80% of all compounds of formula (III) or (IIIa) have the same value for x.

10. The compound of claim 1;
wherein $R^{01}$ is $C_{1-6}$ alkyl.

11. The compound of claim 10;
wherein $R^{01}$ is selected from the group consisting of —$CH_2$—, —$CH_2$—$CH_2$—, and —$CH_2$—$CH_2$—$CH_2$—.

12. The compound of claim 1;
wherein $R^{02}$ is selected from the group consisting of H and $C_{1-6}$ alkyl.

13. The compound of claim 1;
wherein $R^{03}$ is $C_{1-6}$ alkyl.

14. The compound of claim 1;
wherein $R^{04}$ is $C_{1-6}$ alkyl.

* * * * *

UNITED STATES PATENT AND TRADEMARK OFFICE
CERTIFICATE OF CORRECTION

PATENT NO. : 10,040,850 B2
APPLICATION NO. : 15/027976
DATED : August 7, 2018
INVENTOR(S) : Harald Rau et al.

It is certified that error appears in the above-identified patent and that said Letters Patent is hereby corrected as shown below:

In the Specification

Column 11, Line 50, Please replace the second chemical structure 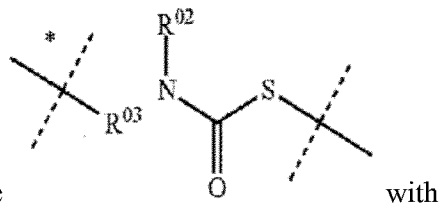 with the following structure:

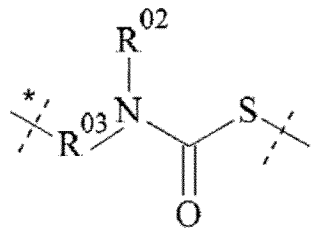

Column 13, Lines 40 to 45, Please replace the second chemical structure 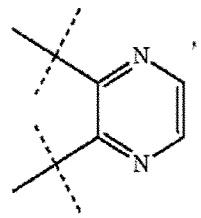 with structure:

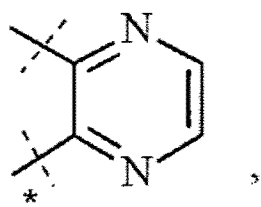

Signed and Sealed this
Fourteenth Day of May, 2019

Andrei Iancu
*Director of the United States Patent and Trademark Office*

Column 14, Lines 55 to 65, Please replace these four chemical structures with the following structures:
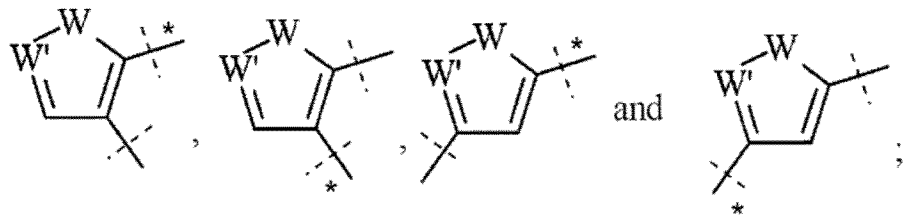
Column 15, Lines 29-34, Please replace the chemical structure 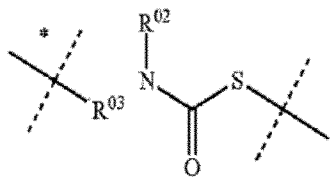 with the following structure:
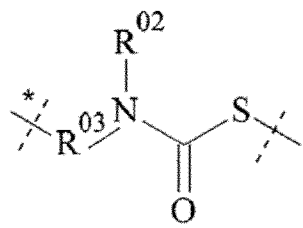
Column 25, Line 30, Please replace the first chemical structure 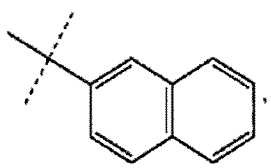 with the structure:
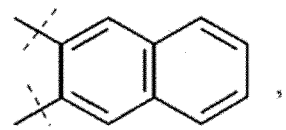
In the Claims
Column 70, Claim 1, Line 30-45, formula (a) Please replace with structure below:
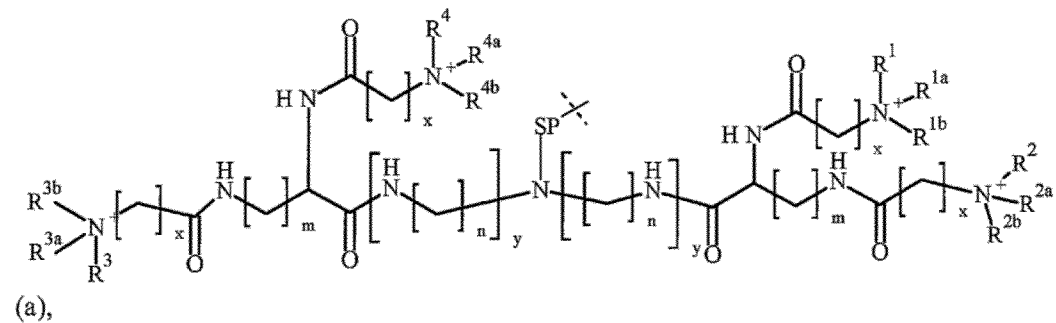
(a),

CERTIFICATE OF CORRECTION (continued)

Column 71, Claim 1, Line 4:
The entity $-N(R^{11})S(O)-$ should be corrected to read $-N(R^{11})S(O)_2-$ Column 71, Claim 1, Line 24:
The entity $-S(O)R^9-$ should be corrected to read $-S(O)_2R^9-$ Column 74, Claim 2, the entire set of chemical structure is wrong. Please replace with the correct set of structure below:

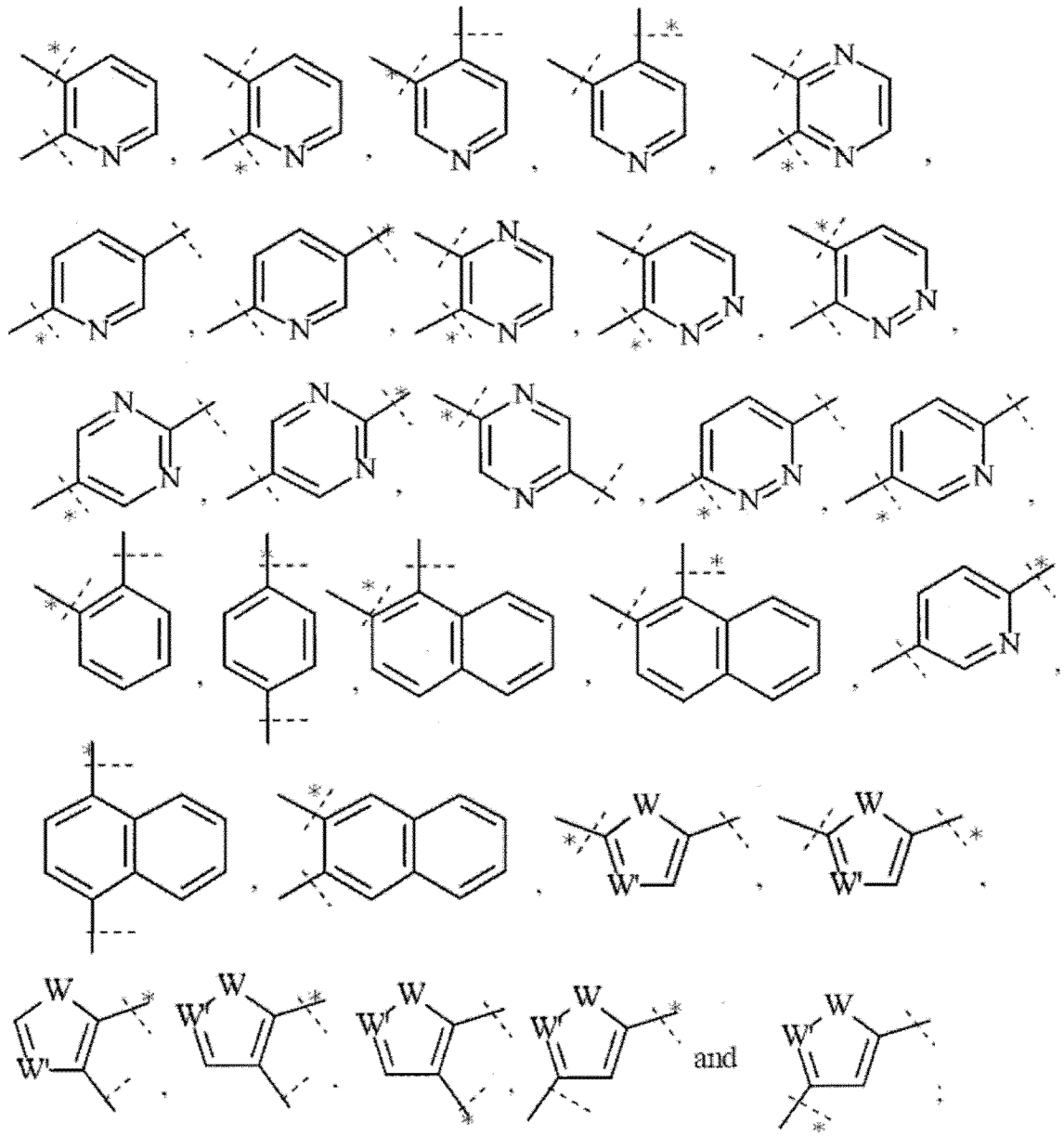

Column 78, Claim 9, Line 31:
formula (II) should be corrected to read formula (III)

CERTIFICATE OF CORRECTION (continued)
U.S. Pat. No. 10,040,850 B2

Page 4 of 4

Column 79, Claim 9, Please replace with formula (a) below:

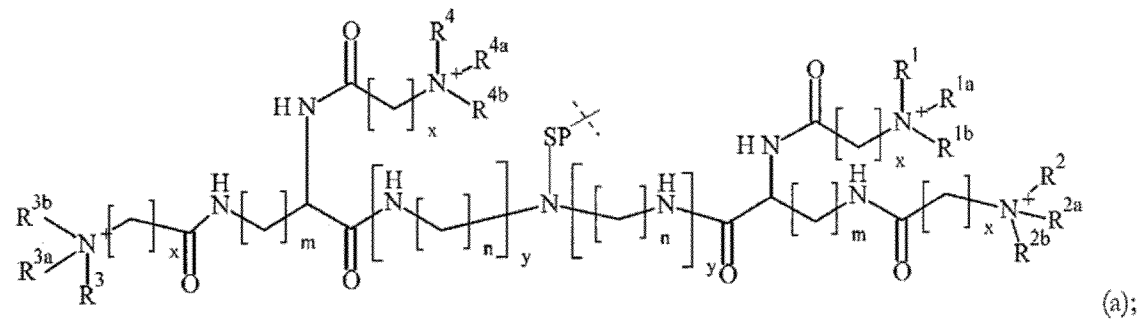

(a);